(12) United States Patent
Chivukula et al.

(10) Patent No.: US 10,369,232 B2
(45) Date of Patent: Aug. 6, 2019

(54) ALLELE SELECTIVE GENE EDITING AND USES THEREOF

(71) Applicant: Arcturus Therapeutics, Inc., San Diego, CA (US)

(72) Inventors: Padmanabh Chivukula, San Diego, CA (US); Rachel Wilkie-Grantham, San Diego, CA (US); Kiyoshi Tachikawa, San Diego, CA (US)

(73) Assignee: Arcturus Therapeutics, Inc., San Diego, CA (US)

( * ) Notice: Subject to any disclaimer, the term of this patent is extended or adjusted under 35 U.S.C. 154(b) by 0 days.

(21) Appl. No.: 15/272,107

(22) Filed: Sep. 21, 2016

(65) Prior Publication Data

US 2017/0080107 A1    Mar. 23, 2017

Related U.S. Application Data

(60) Provisional application No. 62/221,407, filed on Sep. 21, 2015, provisional application No. 62/330,827, filed on May 2, 2016.

(51) Int. Cl.
*A61K 48/00* (2006.01)
*C12N 15/113* (2010.01)
*C12N 15/90* (2006.01)

(52) U.S. Cl.
CPC .......... *A61K 48/005* (2013.01); *C12N 15/113* (2013.01); *C12N 15/907* (2013.01); *C12N 2310/20* (2017.05); *C12N 2310/323* (2013.01); *C12N 2320/34* (2013.01)

(58) Field of Classification Search
None
See application file for complete search history.

(56) References Cited

U.S. PATENT DOCUMENTS 9,957,515 B2 *   5/2018   Beetham .................. C12N 9/22
2015/0232851 A1   8/2015   Wengel

FOREIGN PATENT DOCUMENTS

WO    2014018423 A2    1/2014
WO    2014204724 A1    12/2014

OTHER PUBLICATIONS

Hsu, et al. (Jun. 5, 2014) "Development and Applications of CRISPR-Cas9 for Genome Editing", Cell, 157: 1262-78. (Year: 2014).*
Kurosawa, et al. (Oct. 3, 2005) "Selective silencing of a mutant transthyretin allele by small interfering RNAs", Biochemical and Biophysical Research Communications, 337: 1012-18. (Year: 2005).*
"How to design sgRNA sequences", https://www.takarabio.com/learning-centers/gene-function/gene-editing/gene-editing-overview/how-to-design-sgrna-sequences, Jul. 2, 2014, Author unknown, Published by Takara Bio, USA, Mountain View, CA, 2 pages as printed. (Year: 2014).*
Karvelis, et al. (2013) crRNA and tracrRNA guide Cas9-mediated DNA interference in *Streptococcus thermophiles*, RNA biology, 10(5): 841-51. (Year: 2013).*
Dai, et al. (2016) "CRISP-Cas9 for in vivo Gene Therapy: Promise and Hurdles", Molecular Therapy—Nucleic Acids, 5: e349, 4 pages.*
Brinkman, Easy quantitative assessment of genome editing by sequence trace decomposition, Nucleic Acids Research, 2014, vol. 42, No. 22, e168, pp. 1-8.
Cho, Targeted genome engineering in human cells with the Cas9 RNA-guided endonuclease, Nature Biotechnology, vol. 31, No. 3, Mar. 2013, pp. 230-232 and Supplemental pp. 1-11.
Cong, Multiplex Genome Engineering Using CRISPR/Cas Systems, Science vol. 339 Feb. 15, 2013, pp. 819-823.
Cradick, CRISPR/Cas9 systems targeting b-globin and CCR5 genes have substantial off-target activity, Nucleic Acids Research, 2013, vol. 41, No. 20, pp. 9584-9592.
Fu, High frequency off-target mutagenesis induced by CRISPR-Cas nucleases in human cells, Nat Biotechnol. Sep. 2013; 31(9): pp. 822-826.
Fu, Improving CRISPR-Cas nuclease specificity using truncated guide RNAs, Nature Biotechnology vol. 32 No. 3 Mar. 2014, pp. 279-284 and Supplemental pp. 1-25.
Gasiunas, Cas9-crRNA ribonucleoprotein complex mediates specific DNA cleavage for adaptive immunity in bacteria, PNAS, Sep. 4, 2012, pp. E2579-E2586.
Hendel, Chemically modified guide RNAs enhance CRISPR-Cas genome editing in human primary cells, nature biotechnology vol. 33 No. 9 Sep. 2015, pp. 985-989 and Supplemental 1-29.
Kleinstiver, High-Fidelity CRISPR-Cas9 Nucleases with No Detectable Genome-Wide Off-Target Effects, Molecular Therapy vol. 24, Supplement 1, May 2016, No. 731, pp. S288.
Mail, RNA-Guided Human Genome Engineering via Cas9, Science vol. 339 Feb. 15, 2013. pp. 823-826.
Mali, Cas9 as a versatile tool for engineering biology, nature methods, vol. 10 No. 10, Oct. 2013, pp. 957-963.

(Continued)

*Primary Examiner* — Robert M Kelly
(74) *Attorney, Agent, or Firm* — Mintz, Levin, Cohn, Ferris, Glovsky and Popeo, P.C.

(57) ABSTRACT

This invention encompasses compounds, structures, compositions and methods for therapeutic guide molecules that direct CRISPR gene editing. A guide molecule for directing gene editing can be allele selective, or disease allele selective, and can exhibit reduced off target activity. A guide molecule can be composed of monomers, including UNA monomers, nucleic acid monomers, and modified nucleotides, wherein the compound is targeted to a genomic DNA. The guide molecules of this invention can be used as active ingredients for editing or disrupting a gene in vitro, ex vivo, or in vivo.

25 Claims, 15 Drawing Sheets
Specification includes a Sequence Listing.

(56) References Cited

OTHER PUBLICATIONS

Randar, Synthetic CRISPR RNA-Cas9—guided genome editing in human cells, PNAS, Nov. 16, 2015, pp. E7110-E7117.
Ran, Genome engineering using the CRISPR-Cas9 system, Nature Protocols, 2013, vol. 8 No. 11, pp. 2281-2308.
Ran, In vivo genome editing using *Staphylococcus aureus* Cas9, Nature, vol. 520, Apr. 9, 2015, pp. 186-191 and Supplemental 1-12.
Sander, CRI SPR-Cas systems for editing, regulating and targeting genomes, Nature Biotechnology vol. 32 No. 4 Apr. 2014, pp. 347-355 and Supplemental 1-4.
Sapranauskas, The *Streptococcus thermophilus* CRISPR/Cas system provides immunity in *Escherichia coli*, Nucleic Acids Research, 2011, vol. 39, No. 21, pp. 9275-9282.
Slaymaker, Rationally engineered Cas9 nucleases with improved specificity, Science, Jan. 1, 2016, vol. 351 Issue 6268, pp. 84-88.
Sternberg, DNA interrogation by the CRISPR RNA-guided endonuclease Cas9, Nature, Mar. 6, 2014; 507(7490): pp. 62-67.
Yin, Genome editing with Cas9 in adult mice corrects a disease mutation and phenotype, Nature Biotechnology vol. 32 No. 6 Jun. 2014, pp. 551-553 and Supplemental 1-16.
Yin, Therapeutic genome editing by combined viral and non-viral delivery of CRISPR system components in vivo, Nat Biotechnol. Mar. 2016; 34(3): pp. 328-333.
Yu, Improved delivery of Cas9 protein/gRNA complexes using lipofectamine CRISPRMAX, Biotechnol Lett (2016) 38: pp. 919-929.

\* cited by examiner

```
                              SEQUENCE LISTING

<160> NUMBER OF SEQ ID NOS: 641

<210> SEQ ID NO 1
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
ugcacggcca cauugauggc guuuuagagc uaugcugucc uu                          42

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctggtgcaca gcagtgcatc t                                                 21

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cctctctctg agccctctag ctggta                                            26

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctggtgcaca gcagtgcatc t                                                 21

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cctctctctg agccctctag ctggta                                            26

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 6
tttacagcca cgtctacagc agg                                              23

<210> SEQ ID NO 7
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
uuuacagcca cgucuacagc guuuuagagc uaugcu                                36

<210> SEQ ID NO 8
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
uuuacagcca cgucuacagc guuuuagagc uaugcu                                36

<210> SEQ ID NO 9
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
uuuacagcca cgucuacagc guuuuagagc uaugcu                                36

<210> SEQ ID NO 10
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
uuuacagcca cgucuacagc guuuuagagc uaugcu                                36

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgtcttctct acacccaggg cac                                              23

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
```

```
gcaaaccaca gctagaggag agga                                              24
```

<210> SEQ ID NO 13
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13

```
ugcauggcca cauugauggc                                                   20
```

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14

```
cctgccatca atgtggccat gca                                               23
```

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15

```
tgcatggcca cattgatggc agg                                               23
```

<210> SEQ ID NO 16
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16

```
ugcauggcca cauugauggc guuuuagagc uaugcu                                 36
```

<210> SEQ ID NO 17
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17

```
ugcauggcca cauugauggc guuuuagagc uaugcu                                 36
```

<210> SEQ ID NO 18
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
ugcauggcca cauugauggc guuuuagagc uaugcu                                    36

<210> SEQ ID NO 19
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
ugcauggcca cauugauggc guuuuagagc uaugcu                                    36

<210> SEQ ID NO 20
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
ugcauggcca cauugauggc guuuuagagc uaugcu                                    36

<210> SEQ ID NO 21
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
ugcauggcca cauugauggc guuuuagagc uaugcu                                    36

<210> SEQ ID NO 22
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
ugcauggcca cauugauggc guuuuagagc uaugcu                                    36

<210> SEQ ID NO 23
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
ugcauggcca cauugauggc guuuuagagc uaugcu                                    36

<210> SEQ ID NO 24
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
ugcauggcca cauugauggc guuuuagagc uaugcu                                    36

```
<210> SEQ ID NO 25
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
ugcauggcca cauugauggc guuuuagagc uaugcu                                    36

<210> SEQ ID NO 26
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
ugcauggcca cauugauggc guuuuagagc uaugcu                                    36

<210> SEQ ID NO 27
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
ugcauggcca cauugauggc guuuuagagc uaugcu                                    36

<210> SEQ ID NO 28
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
ugcauggcca cauugauggc guuuuagagc uaugcu                                    36

<210> SEQ ID NO 29
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
ugcauggcca cauugauggc guuuuagagc uaugcu                                    36

<210> SEQ ID NO 30
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
ugcauggcca cauugauggc guuuuagagc uaugcu                                    36
```

```
<210> SEQ ID NO 31
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
ugcauggcca cauugauggc guuuuagagc uaugcu                                 36

<210> SEQ ID NO 32
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
ugcauggcca cauugauggc guuuuagagc uaugcu                                 36

<210> SEQ ID NO 33
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
ugcauggcca cauugauggc guuuuagagc uaugcu                                 36

<210> SEQ ID NO 34
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
ugcauggcca cauugauggc guuuuagagc uaugcu                                 36

<210> SEQ ID NO 35
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
ugcauggcca cauugauggc guuuuagagc uaugcu                                 36

<210> SEQ ID NO 36
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
ugcauggcca cauugauggc guuuuagagc uaugcu                                 36
```

```
<210> SEQ ID NO 37
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
ugcauggcca cauugauggc guuuuagagc uaugcu                              36

<210> SEQ ID NO 38
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ugcauggcca cauugauggc guuuuagagc uaugcu                              36

<210> SEQ ID NO 39
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
ugcauggcca cauugauggc guuuuagagc uaugcu                              36

<210> SEQ ID NO 40
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
cacaugcaug gccacauuga                                                20

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ccatcaatgt ggccatgcat gtg                                            23

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
cacatgcatg gccacattga tgg                                            23

<210> SEQ ID NO 43
```

```
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
cacaugcaug gccacauuga guuuuagagc uaugcu                                  36

<210> SEQ ID NO 44
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
cacaugcaug gccacauuga guuuuagagc uaugcu                                  36

<210> SEQ ID NO 45
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
cacaugcaug gccacauuga guuuuagagc uaugcu                                  36

<210> SEQ ID NO 46
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
cacaugcaug gccacauuga guuuuagagc uaugcu                                  36

<210> SEQ ID NO 47
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
cacaugcaug gccacauuga guuuuagagc uaugcu                                  36

<210> SEQ ID NO 48
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
cacaugcaug gccacauuga guuuuagagc uaugcu                                  36

<210> SEQ ID NO 49
<211> LENGTH: 36
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
cacaugcaug gccacauuga guuuuagagc uaugcu                                 36

<210> SEQ ID NO 50
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
cacaugcaug gccacauuga guuuuagagc uaugcu                                 36

<210> SEQ ID NO 51
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
cacaugcaug gccacauuga guuuuagagc uaugcu                                 36

<210> SEQ ID NO 52
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
cacaugcaug gccacauuga guuuuagagc uaugcu                                 36

<210> SEQ ID NO 53
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
cacaugcaug gccacauuga guuuuagagc uaugcu                                 36

<210> SEQ ID NO 54
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
cacaugcaug gccacauuga guuuuagagc uaugcu                                 36

<210> SEQ ID NO 55
<211> LENGTH: 36
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 55
cacaugcaug gccacauuga guuuagagc uaugcu                                    36

<210> SEQ ID NO 56
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
cacaugcaug gccacauuga guuuagagc uaugcu                                    36

<210> SEQ ID NO 57
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
cacaugcaug gccacauuga guuuagagc uaugcu                                    36

<210> SEQ ID NO 58
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
cacaugcaug gccacauuga guuuagagc uaugcu                                    36

<210> SEQ ID NO 59
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
cacaugcaug gccacauuga guuuagagc uaugcu                                    36

<210> SEQ ID NO 60
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
cacaugcaug gccacauuga guuuagagc uaugcu                                    36

<210> SEQ ID NO 61
<211> LENGTH: 36
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 61
cacaugcaug gccacauuga guuuuagagc uaugcu                                  36

<210> SEQ ID NO 62
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
cacaugcaug gccacauuga guuuuagagc uaugcu                                  36

<210> SEQ ID NO 63
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
cacaugcaug gccacauuga guuuuagagc uaugcu                                  36

<210> SEQ ID NO 64
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
cacaugcaug gccacauuga guuuuagagc uaugcu                                  36

<210> SEQ ID NO 65
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
cacaugcaug gccacauuga guuuuagagc uaugcu                                  36

<210> SEQ ID NO 66
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
cacaugcaug gccacauuga guuuuagagc uaugcu                                  36

<210> SEQ ID NO 67
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 67
gaugcggugg uccuugagaa                                               20

<210> SEQ ID NO 68
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
caagaacugg cccuucuugg                                               20

<210> SEQ ID NO 69
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
gcaggcgcag cccuccaaga                                               20

<210> SEQ ID NO 70
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
uucugcuuca aggagcugga                                               20

<210> SEQ ID NO 71
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
ccaguuucaa aaauucacca                                               20

<210> SEQ ID NO 72
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
caauaagaag aaagaauuug                                               20

<210> SEQ ID NO 73
<211> LENGTH: 42
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 73
gaugcggugg uccuugagaa guuuuagagc uaugcuguccuu    42

<210> SEQ ID NO 74
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
ugaugcggug guccuugaga aguuuuagag cuaugcuguc cuu    43

<210> SEQ ID NO 75
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
ugaugcggug guccuugaga aguuuuagag cuaugcuguc cuu    43

<210> SEQ ID NO 76
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
ugaugcggug guccuugaga aguuuuagag cuaugcuguc cuu    43

<210> SEQ ID NO 77
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
uuugaugcgg ugguccuuga gaaguuuuag agcuaugcug uccuuuu    47

<210> SEQ ID NO 78
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
uuugaugcgg ugguccuuga gaaguuuuag agcuaugcug uccuuuu    47

<210> SEQ ID NO 79
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
uuugaugcgg ugguccuuga gaaguuuuag agcuaugcug uccuuuu            47

<210> SEQ ID NO 80
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
uuugaugcgg ugguccuuga gaaguuuuag agcuaugcug uccuuuu            47

<210> SEQ ID NO 81
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
uuugaugcgg ugguccuuga gaaguuuuag agcuaugcug uccuuuu            47

<210> SEQ ID NO 82
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
uuugaugcgg ugguccuuga gaaguuuuag agcuaugcug uccuuuu            47

<210> SEQ ID NO 83
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
uuugaugcgg ugguccuuga gaaguuuuag agcuaugcug uccuuuu            47

<210> SEQ ID NO 84
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
caagaacugg cccuucuugg guuuuagagc uaugcugucc uu                 42

<210> SEQ ID NO 85
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 85
ucaagaacug gcccuucuug gguuuuagag cuaugcuguc cuu          43

<210> SEQ ID NO 86
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
ucaagaacug gcccuucuug gguuuuagag cuaugcuguc cuu          43

<210> SEQ ID NO 87
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
ucaagaacug gcccuucuug gguuuuagag cuaugcuguc cuu          43

<210> SEQ ID NO 88
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
uucaagaacu ggcccuucuu ggguuuuaga gcuaugcugu ccuuuu       46

<210> SEQ ID NO 89
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
uucaagaacu ggcccuucuu ggguuuuaga gcuaugcugu ccuuuu       46

<210> SEQ ID NO 90
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
uucaagaacu ggcccuucuu ggguuuuaga gcuaugcugu ccuuuu       46

<210> SEQ ID NO 91
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
```
uuucaagaac uggcccuucu uggguuuuag agcuaugcug uccuuuu     47

<210> SEQ ID NO 92
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
uuucaagaac uggcccuucu uggguuuuag agcuaugcug uccuuuu     47

<210> SEQ ID NO 93
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
uuucaagaac uggcccuucu uggguuuuag agcuaugcug uccuuuu     47

<210> SEQ ID NO 94
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
uuucaagaac uggcccuucu uggguuuuag agcuaugcug uccuuuu     47

<210> SEQ ID NO 95
<211> LENGTH: 42
<212> TYPE: RNA
<213> ORGANISM: Artificial Sequence
<220> FEATURE:
<223> OTHER INFORMATION: Description of Artificial Sequence: Synthetic
      oligoneotide

<400> SEQUENCE: 95
gcaggcgcag cccuccaaga guuuuagagc uaugcugucc uu     42

<210> SEQ ID NO 96
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
ugcaggcgca gcccuccaag aguuuuagag cuaugcuguc cuu     43

<210> SEQ ID NO 97
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
ugcaggcgca gcccuccaag aguuuuagag cuaugcuguc cuu        43

<210> SEQ ID NO 98
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
ugcaggcgca gcccuccaag aguuuuagag cuaugcuguc cuu        43

<210> SEQ ID NO 99
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
uugcaggcgc agcccuccaa gaguuuuaga gcuaugcugu ccuuuu        46

<210> SEQ ID NO 100
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
uugcaggcgc agcccuccaa gaguuuuaga gcuaugcugu ccuuuu        46

<210> SEQ ID NO 101
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
uugcaggcgc agcccuccaa gaguuuuaga gcuaugcugu ccuuuu        46

<210> SEQ ID NO 102
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
uuugcaggcg cagcccucca agaguuuuag agcuaugcug uccuuuu        47

<210> SEQ ID NO 103
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
uuugcaggcg cagcccucca agaguuuuag agcuaugcug uccuuuu        47

<210> SEQ ID NO 104
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
uuugcaggcg cagcccucca agaguuuuag agcuaugcug uccuuuu                    47

<210> SEQ ID NO 105
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
uuugcaggcg cagcccucca agaguuuuag agcuaugcug uccuuuu                    47

<210> SEQ ID NO 106
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
uucugcuuca aggagcugga guuuuagagc uaugcugucc uu                         42

<210> SEQ ID NO 107
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
uuucugcuuc aaggagcugg aguuuuagag cuaugcuguc cuu                        43

<210> SEQ ID NO 108
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
uuucugcuuc aaggagcugg aguuuuagag cuaugcuguc cuu                        43

<210> SEQ ID NO 109
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
uuucugcuuc aaggagcugg aguuuuagag cuaugcuguc cuu                        43

<210> SEQ ID NO 110
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
uuuucugcuu caaggagcug gaguuuuaga gcuaugcugu ccuuuu                46

<210> SEQ ID NO 111
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
uuuucugcuu caaggagcug gaguuuuaga gcuaugcugu ccuuuu                46

<210> SEQ ID NO 112
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
uuuucugcuu caaggagcug gaguuuuaga gcuaugcugu ccuuuu                46

<210> SEQ ID NO 113
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
uuuuucugcu ucaaggagcu ggaguuuuag agcuaugcug uccuuuu                47

<210> SEQ ID NO 114
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
uuuuucugcu ucaaggagcu ggaguuuuag agcuaugcug uccuuuu                47

<210> SEQ ID NO 115
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
uuuuucugcu ucaaggagcu ggaguuuuag agcuaugcug uccuuuu                47

```
<210> SEQ ID NO 116
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
uuuuucugcu ucaaggagcu ggaguuuuag agcuaugcug uccuuuu                 47

<210> SEQ ID NO 117
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
ccaguuucaa aaauucacca guuuuagagc uaugcugucc uu                      42

<210> SEQ ID NO 118
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
uccaguuuca aaaauucacc aguuuuagag cuaugcuguc cuu                     43

<210> SEQ ID NO 119
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
uccaguuuca aaaauucacc aguuuuagag cuaugcuguc cuu                     43

<210> SEQ ID NO 120
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
uccaguuuca aaaauucacc aguuuuagag cuaugcuguc cuu                     43

<210> SEQ ID NO 121
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
uuccaguuuc aaaaauucac caguuuuaga gcuaugcugu ccuuuu                  46

<210> SEQ ID NO 122
```

```
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
uuccaguuuc aaaaauucac caguuuuaga gcuaugcugu ccuuuu          46

<210> SEQ ID NO 123
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
uuccaguuuc aaaaauucac caguuuuaga gcuaugcugu ccuuuu          46

<210> SEQ ID NO 124
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
uuuccaguuu caaaaauuca ccaguuuuag agcuaugcug uccuuuu         47

<210> SEQ ID NO 125
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
uuuccaguuu caaaaauuca ccaguuuuag agcuaugcug uccuuuu         47

<210> SEQ ID NO 126
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
uuuccaguuu caaaaauuca ccaguuuuag agcuaugcug uccuuuu         47

<210> SEQ ID NO 127
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
uuuccaguuu caaaaauuca ccaguuuuag agcuaugcug uccuuuu         47

<210> SEQ ID NO 128
<211> LENGTH: 42
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
caauaagaag aaagaauuug guuuuagagc uaugcuguc cuu                              42

<210> SEQ ID NO 129
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
ucaauaagaa gaaagaauuu gguuuuagag cuaugcuguc cuu                             43

<210> SEQ ID NO 130
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
ucaauaagaa gaaagaauuu gguuuuagag cuaugcuguc cuu                             43

<210> SEQ ID NO 131
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
ucaauaagaa gaaagaauuu gguuuuagag cuaugcuguc cuu                             43

<210> SEQ ID NO 132
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
uucaauaaga agaaagaauu ugguuuuaga gcuaugcugu ccuuuu                          46

<210> SEQ ID NO 133
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
uucaauaaga agaaagaauu ugguuuuaga gcuaugcugu ccuuuu                          46

<210> SEQ ID NO 134
<211> LENGTH: 46
<212> TYPE: RNA
```

<213> ORGANISM: Artificial Sequence
<220> FEATURE:
<223> OTHER INFORMATION: Description of Artificial Sequence: Synthetic
oligonucleotide

<400> SEQUENCE: 134
uucaauaaga agaaagaauu ugguuuuaga gcuaugcugu ccuuuu            46

<210> SEQ ID NO 135
<211> LENGTH: 47
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 135
uuucaauaag aagaaagaau uugguuuuag agcuaugcug uccuuuu           47

<210> SEQ ID NO 136
<211> LENGTH: 47
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 136
uuucaauaag aagaaagaau uugguuuuag agcuaugcug uccuuuu           47

<210> SEQ ID NO 137
<211> LENGTH: 47
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 137
uuucaauaag aagaaagaau uugguuuuag agcuaugcug uccuuuu           47

<210> SEQ ID NO 138
<211> LENGTH: 47
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 138
uuucaauaag aagaaagaau uugguuuuag agcuaugcug uccuuuu           47

<210> SEQ ID NO 139
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 139
cgugcagaac gaaguucccc                                         20

<210> SEQ ID NO 140
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
uggagacugc accucauccg                                               20

<210> SEQ ID NO 141
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
ugaucuccuu gagugccaca                                               20

<210> SEQ ID NO 142
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
ugauguuccc acagucaucc                                               20

<210> SEQ ID NO 143
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
aguaguccgu ggacccaagc                                               20

<210> SEQ ID NO 144
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
cuaccccaag uaccgagccg                                               20

<210> SEQ ID NO 145
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
cgugcagaac gaaguucccc guuuuagagc uaugcugucc uu                      42

<210> SEQ ID NO 146
<211> LENGTH: 43
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 146
ucgugcagaa cgaaguuccc cguuuuagag cuaugcuguc cuu          43

<210> SEQ ID NO 147
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
ucgugcagaa cgaaguuccc cguuuuagag cuaugcuguc cuu          43

<210> SEQ ID NO 148
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
ucgugcagaa cgaaguuccc cguuuuagag cuaugcuguc cuu          43

<210> SEQ ID NO 149
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
uucgugcaga acgaaguucc ccguuuuaga gcuaugcugu ccuuuu       46

<210> SEQ ID NO 150
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
uucgugcaga acgaaguucc ccguuuuaga gcuaugcugu ccuuuu       46

<210> SEQ ID NO 151
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
uucgugcaga acgaaguucc ccguuuuaga gcuaugcugu ccuuuu       46

<210> SEQ ID NO 152
<211> LENGTH: 47
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 152
uuucgugcag aacgaaguuc cccguuuuag agcuaugcug uccuuuu       47

<210> SEQ ID NO 153
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
uuucgugcag aacgaaguuc cccguuuuag agcuaugcug uccuuuu       47

<210> SEQ ID NO 154
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
uuucgugcag aacgaaguuc cccguuuuag agcuaugcug uccuuuu       47

<210> SEQ ID NO 155
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
uuucgugcag aacgaaguuc cccguuuuag agcuaugcug uccuuuu       47

<210> SEQ ID NO 156
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
uggagacugc accucauccg guuuuagagc uaugcugucc uu       42

<210> SEQ ID NO 157
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
uuggagacug caccucaucc gguuuuagag cuaugcuguc cuu       43

<210> SEQ ID NO 158
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
uuggagacug caccucaucc gguuuuagag cuaugcuguc cuu        43

<210> SEQ ID NO 159
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
uuggagacug caccucaucc gguuuuagag cuaugcuguc cuu        43

<210> SEQ ID NO 160
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
uuuggagacu gcaccucauc cgguuuuaga gcuaugcugu ccuuuu        46

<210> SEQ ID NO 161
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
uuuggagacu gcaccucauc cgguuuuaga gcuaugcugu ccuuuu        46

<210> SEQ ID NO 162
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
uuuggagacu gcaccucauc cgguuuuaga gcuaugcugu ccuuuu        46

<210> SEQ ID NO 163
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
uuuuggagac ugcaccucau ccgguuuuag agcuaugcug uccuuuu        47

<210> SEQ ID NO 164
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
uuuuggagac ugcaccucau ccgguuuuag agcuaugcug uccuuuu     47

<210> SEQ ID NO 165
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
uuuuggagac ugcaccucau ccgguuuuag agcuaugcug uccuuuu     47

<210> SEQ ID NO 166
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
uuuuggagac ugcaccucau ccgguuuuag agcuaugcug uccuuuu     47

<210> SEQ ID NO 167
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
ugaucuccuu gagugccaca guuuuagagc uaugcugucc uu     42

<210> SEQ ID NO 168
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
uugaucuccu ugagugccac aguuuuagag cuaugcuguc cuu     43

<210> SEQ ID NO 169
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
uugaucuccu ugagugccac aguuuuagag cuaugcuguc cuu     43

<210> SEQ ID NO 170
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
uugaucuccu ugagugccac aguuuuagag cuaugcuguc cuu          43

<210> SEQ ID NO 171
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
uuugaucucc uugagugcca caguuuuaga gcuaugcugu ccuuuu          46

<210> SEQ ID NO 172
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
uuugaucucc uugagugcca caguuuuaga gcuaugcugu ccuuuu          46

<210> SEQ ID NO 173
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
uuugaucucc uugagugcca caguuuuaga gcuaugcugu ccuuuu          46

<210> SEQ ID NO 174
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
uuuugaucuc cuugagugcc acaguuuuag agcuaugcug uccuuuu          47

<210> SEQ ID NO 175
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
uuuugaucuc cuugagugcc acaguuuuag agcuaugcug uccuuuu          47

<210> SEQ ID NO 176
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176

```
uuuugaucuc cuugagugcc acaguuuuag agcuaugcug uccuuuu                    47
```

<210> SEQ ID NO 177
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177

```
uuuugaucuc cuugagugcc acaguuuuag agcuaugcug uccuuuu                    47
```

<210> SEQ ID NO 178
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178

```
ugauguuccc acagucaucc guuuuagagc uaugcugucc uu                         42
```

<210> SEQ ID NO 179
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179

```
uugauguucc cacagucauc cguuuuagag cuaugcuguc cuu                        43
```

<210> SEQ ID NO 180
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180

```
uugauguucc cacagucauc cguuuuagag cuaugcuguc cuu                        43
```

<210> SEQ ID NO 181
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181

```
uugauguucc cacagucauc cguuuuagag cuaugcuguc cuu                        43
```

<210> SEQ ID NO 182
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182

```
uuugauguuc ccacagucau ccguuuuaga gcuaugcugu ccuuuu                     46
```

```
<210> SEQ ID NO 183
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
uuugauguuc ccacagucau ccguuuuaga gcuaugcugu ccuuuu              46

<210> SEQ ID NO 184
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
uuugauguuc ccacagucau ccguuuuaga gcuaugcugu ccuuuu              46

<210> SEQ ID NO 185
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
uuuugauguu cccacaguca uccguuuuag agcuaugcug uccuuuu             47

<210> SEQ ID NO 186
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
uuuugauguu cccacaguca uccguuuuag agcuaugcug uccuuuu             47

<210> SEQ ID NO 187
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
uuuugauguu cccacaguca uccguuuuag agcuaugcug uccuuuu             47

<210> SEQ ID NO 188
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
uuuugauguu cccacaguca uccguuuuag agcuaugcug uccuuuu             47
```

<210> SEQ ID NO 189
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
aguaguccgu ggacccaagc guuuuagagc uaugcugucc uu                        42

<210> SEQ ID NO 190
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
uaguaguccg uggacccaag cguuuuagag cuaugcuguc cuu                       43

<210> SEQ ID NO 191
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
uaguaguccg uggacccaag cguuuuagag cuaugcuguc cuu                       43

<210> SEQ ID NO 192
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
uaguaguccg uggacccaag cguuuuagag cuaugcuguc cuu                       43

<210> SEQ ID NO 193
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
uuaguagucc guggacccaa gcguuuuaga gcuaugcugu ccuuuu                    46

<210> SEQ ID NO 194
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
uuaguagucc guggacccaa gcguuuuaga gcuaugcugu ccuuuu                    46

<210> SEQ ID NO 195
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
uuaguagucc guggacccaa gcguuuuaga gcuaugcugu ccuuuu       46

<210> SEQ ID NO 196
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
uuuaguaguc cguggaccca agcguuuuag agcuaugcug uccuuuu      47

<210> SEQ ID NO 197
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
uuuaguaguc cguggaccca agcguuuuag agcuaugcug uccuuuu      47

<210> SEQ ID NO 198
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
uuuaguaguc cguggaccca agcguuuuag agcuaugcug uccuuuu      47

<210> SEQ ID NO 199
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
uuuaguaguc cguggaccca agcguuuuag agcuaugcug uccuuuu      47

<210> SEQ ID NO 200
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
cuaccccaag uaccgagccg guuuuagagc uaugcugucc uu           42

<210> SEQ ID NO 201

```
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
ucuaccccaa guaccgagcc gguuuuagag cuaugcuguc cuu                43

<210> SEQ ID NO 202
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
ucuaccccaa guaccgagcc gguuuuagag cuaugcuguc cuu                43

<210> SEQ ID NO 203
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
ucuaccccaa guaccgagcc gguuuuagag cuaugcuguc cuu                43

<210> SEQ ID NO 204
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
uucuacccca aguaccgagc cgguuuuaga gcuaugcugu ccuuuu             46

<210> SEQ ID NO 205
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
uucuacccca aguaccgagc cgguuuuaga gcuaugcugu ccuuuu             46

<210> SEQ ID NO 206
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
uucuacccca aguaccgagc cgguuuuaga gcuaugcugu ccuuuu             46

<210> SEQ ID NO 207
<211> LENGTH: 47
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
uuucuacccc aaguaccgag ccgguuuuag agcuaugcug uccuuuu          47

<210> SEQ ID NO 208
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
uuucuacccc aaguaccgag ccgguuuuag agcuaugcug uccuuuu          47

<210> SEQ ID NO 209
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
uuucuacccc aaguaccgag ccgguuuuag agcuaugcug uccuuuu          47

<210> SEQ ID NO 210
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210
uuucuacccc aaguaccgag ccgguuuuag agcuaugcug uccuuuu          47

<210> SEQ ID NO 211
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
agagcugaug gagcugcucc                                        20

<210> SEQ ID NO 212
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
acugcugguc aaucucuccc                                        20

<210> SEQ ID NO 213
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 213
cucucuuccg gacauccuga                                                      20

<210> SEQ ID NO 214
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
gagaccgagg uguaucacca                                                      20

<210> SEQ ID NO 215
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
aaccugggau caaguggccg                                                      20

<210> SEQ ID NO 216
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216
gaaggugcug aacccucagc                                                      20

<210> SEQ ID NO 217
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
agagcugaug gagcugcucc guuuuagagc uaugcugucc uu                             42

<210> SEQ ID NO 218
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
uagagcugau ggagcugcuc cguuuuagag cuaugcuguc cuu                            43

<210> SEQ ID NO 219
<211> LENGTH: 43
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 219
uagagcugau ggagcugcuc cguuuuagag cuaugcuguc cuu                    43

<210> SEQ ID NO 220
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
uagagcugau ggagcugcuc cguuuuagag cuaugcuguc cuu                    43

<210> SEQ ID NO 221
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
uuagagcuga uggagcugcu ccguuuuaga gcuaugcugu ccuuuu                 46

<210> SEQ ID NO 222
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
uuagagcuga uggagcugcu ccguuuuaga gcuaugcugu ccuuuu                 46

<210> SEQ ID NO 223
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
uuagagcuga uggagcugcu ccguuuuaga gcuaugcugu ccuuuu                 46

<210> SEQ ID NO 224
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
uuuagagcug auggagcugc uccguuuuag agcuaugcug uccuuuu                47

<210> SEQ ID NO 225
<211> LENGTH: 47
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 225
uuuagagcug auggagcugc uccguuuuag agcuaugcug uccuuuu            47

<210> SEQ ID NO 226
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
uuuagagcug auggagcugc uccguuuuag agcuaugcug uccuuuu            47

<210> SEQ ID NO 227
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
uuuagagcug auggagcugc uccguuuuag agcuaugcug uccuuuu            47

<210> SEQ ID NO 228
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
acugcugguc aaucucuccc guuuuagagc uaugcugucc uu                 42

<210> SEQ ID NO 229
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
uacugcuggu caaucucucc cguuuuagag cuaugcuguc cuu                43

<210> SEQ ID NO 230
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
uacugcuggu caaucucucc cguuuuagag cuaugcuguc cuu                43

<210> SEQ ID NO 231
<211> LENGTH: 43
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 231
uacugcuggu caaucucucc cguuuuagag cuaugcuguc cuu         43

<210> SEQ ID NO 232
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
uuacugcugg ucaaucucuc ccguuuuaga gcuaugcugu ccuuuu        46

<210> SEQ ID NO 233
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
uuacugcugg ucaaucucuc ccguuuuaga gcuaugcugu ccuuuu        46

<210> SEQ ID NO 234
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
uuacugcugg ucaaucucuc ccguuuuaga gcuaugcugu ccuuuu        46

<210> SEQ ID NO 235
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
uuuacugcug gucaaucucu cccguuuuag agcuaugcug uccuuuu       47

<210> SEQ ID NO 236
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
uuuacugcug gucaaucucu cccguuuuag agcuaugcug uccuuuu       47

<210> SEQ ID NO 237
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 237
uuuacugcug gucaaucucu cccguuuuag agcuaugcug uccuuuu          47

<210> SEQ ID NO 238
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
uuuacugcug gucaaucucu cccguuuuag agcuaugcug uccuuuu          47

<210> SEQ ID NO 239
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
cucucuuccg gacauccuga guuuuagagc uaugcuguCC uu               42

<210> SEQ ID NO 240
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
ucucucuucc ggacauccug aguuuuagag cuaugcuguc cuu              43

<210> SEQ ID NO 241
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
ucucucuucc ggacauccug aguuuuagag cuaugcuguc cuu              43

<210> SEQ ID NO 242
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
ucucucuucc ggacauccug aguuuuagag cuaugcuguc cuu              43

<210> SEQ ID NO 243
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 243
uucucucuuc cggacauccu gaguuuuaga gcuaugcugu ccuuuu            46

<210> SEQ ID NO 244
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
uucucucuuc cggacauccu gaguuuuaga gcuaugcugu ccuuuu            46

<210> SEQ ID NO 245
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
uucucucuuc cggacauccu gaguuuuaga gcuaugcugu ccuuuu            46

<210> SEQ ID NO 246
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246
uuucucucuu ccggacaucc ugaguuuuag agcuaugcug uccuuuu           47

<210> SEQ ID NO 247
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
uuucucucuu ccggacaucc ugaguuuuag agcuaugcug uccuuuu           47

<210> SEQ ID NO 248
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
uuucucucuu ccggacaucc ugaguuuuag agcuaugcug uccuuuu           47

<210> SEQ ID NO 249
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
uuucucucuu ccggacaucc ugaguuuuag agcuaugcug uccuuuu                47

<210> SEQ ID NO 250
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
gagaccgagg uguaucacca guuuuagagc uaugcugucc uu                    42

<210> SEQ ID NO 251
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
ugagaccgag guguaucacc aguuuuagag cuaugcuguc cuu                   43

<210> SEQ ID NO 252
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252
ugagaccgag guguaucacc aguuuuagag cuaugcuguc cuu                   43

<210> SEQ ID NO 253
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
ugagaccgag guguaucacc aguuuuagag cuaugcuguc cuu                   43

<210> SEQ ID NO 254
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
uugagaccga gguguaucac caguuuuaga gcuaugcugu ccuuuu                46

<210> SEQ ID NO 255
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
uugagaccga gguguaucac caguuuuaga gcuaugcugu ccuuuu         46

<210> SEQ ID NO 256
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 256
uuugagaccg agguguauca ccaguuuuag agcuaugcug uccuuuu         47

<210> SEQ ID NO 257
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 257
uuugagaccg agguguauca ccaguuuuag agcuaugcug uccuuuu         47

<210> SEQ ID NO 258
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
uuugagaccg agguguauca ccaguuuuag agcuaugcug uccuuuu         47

<210> SEQ ID NO 259
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259
uuugagaccg agguguauca ccaguuuuag agcuaugcug uccuuuu         47

<210> SEQ ID NO 260
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260
uuugagaccg agguguauca ccaguuuuag agcuaugcug uccuuuu         47

<210> SEQ ID NO 261
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
aaccugggau caaguggccg guuuuagagc uaugcugucc uu         42

```
<210> SEQ ID NO 262
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 262
uaaccuggga ucaaguggcc gguuuuagag cuaugcuguc cuu                   43

<210> SEQ ID NO 263
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 263
uaaccuggga ucaaguggcc gguuuuagag cuaugcuguc cuu                   43

<210> SEQ ID NO 264
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 264
uaaccuggga ucaaguggcc gguuuuagag cuaugcuguc cuu                   43

<210> SEQ ID NO 265
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 265
uuaaccuggg aucaaguggc cgguuuuaga gcuaugcugu ccuuuu                46

<210> SEQ ID NO 266
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 266
uuaaccuggg aucaaguggc cgguuuuaga gcuaugcugu ccuuuu                46

<210> SEQ ID NO 267
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 267
uuaaccuggg aucaaguggc cgguuuuaga gcuaugcugu ccuuuu                46
```

<210> SEQ ID NO 268
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 268
uuuaaccugg gaucaagugg ccgguuuuag agcuaugcug uccuuuu                    47

<210> SEQ ID NO 269
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 269
uuuaaccugg gaucaagugg ccgguuuuag agcuaugcug uccuuuu                    47

<210> SEQ ID NO 270
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
uuuaaccugg gaucaagugg ccgguuuuag agcuaugcug uccuuuu                    47

<210> SEQ ID NO 271
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 271
uuuaaccugg gaucaagugg ccgguuuuag agcuaugcug uccuuuu                    47

<210> SEQ ID NO 272
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 272
gaaggugcug aacccucagc guuuuagagc uaugcugucc uu                         42

<210> SEQ ID NO 273
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
ugaaggugcu gaacccucag caguuuuaga gcuaugcugu ccuu                       44

<210> SEQ ID NO 274
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 274
ugaaggugcu gaacccucag cguuuuagag cuaugcuguc cuu        43

<210> SEQ ID NO 275
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 275
ugaaggugcu gaacccucag cguuuuagag cuaugcuguc cuu        43

<210> SEQ ID NO 276
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 276
uugaaggugc ugaacccuca gcguuuuaga gcuaugcugu ccuuuu        46

<210> SEQ ID NO 277
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 277
uugaaggugc ugaacccuca gcguuuuaga gcuaugcugu ccuuuu        46

<210> SEQ ID NO 278
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278
uuugaaggug cugaacccuc agcguuuuag agcuaugcug uccuuuu        47

<210> SEQ ID NO 279
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
uuugaaggug cugaacccuc agcguuuuag agcuaugcug uccuuuu        47

<210> SEQ ID NO 280

```
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 280
uuugaaggug cugaacccuc agcguuuuag agcuaugcug uccuuuu                      47

<210> SEQ ID NO 281
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
uuugaaggug cugaacccuc agcguuuuag agcuaugcug uccuuuu                      47

<210> SEQ ID NO 282
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 282
uuugaaggug cugaacccuc agcguuuuag agcuaugcug uccuuuu                      47

<210> SEQ ID NO 283
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
gguauauguc ugacaauucc                                                    20

<210> SEQ ID NO 284
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
acucccagau uagccccaug                                                    20

<210> SEQ ID NO 285
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
aaggacagcc uucucucuaa                                                    20

<210> SEQ ID NO 286
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
ugcugaucac gcugaugcg                                                    19

<210> SEQ ID NO 287
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
cuauucccuu ugucuugaag                                                   20

<210> SEQ ID NO 288
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288
uucauugaca ugccaacaga                                                   20

<210> SEQ ID NO 289
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289
gguauauguc ugacaauucc guuuuagagc uaugcugucc uu                          42

<210> SEQ ID NO 290
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290
ugguauaugu cugacaauuc cguuuuagag cuaugcuguc cuu                         43

<210> SEQ ID NO 291
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
ugguauaugu cugacaauuc cguuuuagag cuaugcuguc cuu                         43

<210> SEQ ID NO 292
<211> LENGTH: 43
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 292
ugguauaugu cugacaauuc cguuuuagag cuaugcuguc cuu                43

<210> SEQ ID NO 293
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293
uugguauaug ucugacaauu ccguuuuaga gcuaugcugu ccuuuu           46

<210> SEQ ID NO 294
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294
uugguauaug ucugacaauu ccguuuuaga gcuaugcugu ccuuuu           46

<210> SEQ ID NO 295
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 295
uugguauaug ucugacaauu ccguuuuaga gcuaugcugu ccuuuu           46

<210> SEQ ID NO 296
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296
uuugguauau gucugacaau uccguuuuag agcuaugcug uccuuuu          47

<210> SEQ ID NO 297
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
uuugguauau gucugacaau uccguuuuag agcuaugcug uccuuuu          47

<210> SEQ ID NO 298
<211> LENGTH: 47
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 298
uuugguauau gucugacaau uccguuuuag agcuaugcug uccuuuu                47

<210> SEQ ID NO 299
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299
uuugguauau gucugacaau uccguuuuag agcuaugcug uccuuuu                47

<210> SEQ ID NO 300
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 300
acucccagau uagccccaug guuuuagagc uaugcuglucc uu                    42

<210> SEQ ID NO 301
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 301
uacucccaga uuagccccau gguuuuagag cuaugcuguc cuu                    43

<210> SEQ ID NO 302
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
uacucccaga uuagccccau gguuuuagag cuaugcuguc cuu                    43

<210> SEQ ID NO 303
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
uacucccaga uuagccccau gguuuuagag cuaugcuguc cuu                    43

<210> SEQ ID NO 304
<211> LENGTH: 46
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 304
uuacucccag auuagcccca ugguuuuaga gcuaugcugu ccuuuu         46

<210> SEQ ID NO 305
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 305
uuacucccag auuagcccca ugguuuuaga gcuaugcugu ccuuuu         46

<210> SEQ ID NO 306
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
uuacucccag auuagcccca ugguuuuaga gcuaugcugu ccuuuu         46

<210> SEQ ID NO 307
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
uuuacuccca gauuagcccc augguuuuag agcuaugcug uccuuuu        47

<210> SEQ ID NO 308
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
uuuacuccca gauuagcccc augguuuuag agcuaugcug uccuuuu        47

<210> SEQ ID NO 309
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
uuuacuccca gauuagcccc augguuuuag agcuaugcug uccuuuu        47

<210> SEQ ID NO 310
<211> LENGTH: 47
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 310
uuuacuccca gauuagcccc augguuuuag agcuaugcug uccuuuu        47

<210> SEQ ID NO 311
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
aaggacagcc uucucucuaa guuuuagagc uaugcugucc uu        42

<210> SEQ ID NO 312
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 312
uaaggacagc cuucucucua aguuuuagag cuaugcuguc cuu        43

<210> SEQ ID NO 313
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 313
uaaggacagc cuucucucua aguuuuagag cuaugcuguc cuu        43

<210> SEQ ID NO 314
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 314
uaaggacagc cuucucucua aguuuuagag cuaugcuguc cuu        43

<210> SEQ ID NO 315
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
uuaaggacag ccuucucucu aaguuuuaga gcuaugcugu ccuuuu        46

<210> SEQ ID NO 316
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
uuaaggacag ccuucucucu aaguuuuaga gcuaugcugu ccuuuu     46

<210> SEQ ID NO 317
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 317
uuaaggacag ccuucucucu aaguuuuaga gcuaugcugu ccuuuu     46

<210> SEQ ID NO 318
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 318
uuuaaggaca gccuucucuc uaaguuuuag agcuaugcug uccuuuu     47

<210> SEQ ID NO 319
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 319
uuuaaggaca gccuucucuc uaaguuuuag agcuaugcug uccuuuu     47

<210> SEQ ID NO 320
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
uuuaaggaca gccuucucuc uaaguuuuag agcuaugcug uccuuuu     47

<210> SEQ ID NO 321
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 321
uuuaaggaca gccuucucuc uaaguuuuag agcuaugcug uccuuuu     47

<210> SEQ ID NO 322
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 322
ugcugaucac gcugaugcgg uuuuagagcu augcuguccu u              41

<210> SEQ ID NO 323
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 323
uugcugauca cgcugaugcg guuuuagagc uaugcugucc uu             42

<210> SEQ ID NO 324
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 324
uugcugauca cgcugaugcg guuuuagagc uaugcugucc uu             42

<210> SEQ ID NO 325
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 325
uugcugauca cgcugaugcg guuuuagagc uaugcugucc uu             42

<210> SEQ ID NO 326
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 326
uuugcugauc acgcugaugc gguuuuagag cuaugcuguc cuuuu          45

<210> SEQ ID NO 327
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 327
uuugcugauc acgcugaugc gguuuuagag cuaugcuguc cuuuu          45

<210> SEQ ID NO 328
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 328
```
uuugcugauc acgcugaugc gguuuuagag cuaugcuguc cuuuu 45

<210> SEQ ID NO 329
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 329
uuuugcugau cacgcugaug cgguuuuaga gcuaugcugu ccuuuu 46

<210> SEQ ID NO 330
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 330
uuuugcugau cacgcugaug cgguuuuaga gcuaugcugu ccuuuu 46

<210> SEQ ID NO 331
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 331
uuuugcugau cacgcugaug cgguuuuaga gcuaugcugu ccuuuu 46

<210> SEQ ID NO 332
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 332
uuuugcugau cacgcugaug cgguuuuaga gcuaugcugu ccuuuu 46

<210> SEQ ID NO 333
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 333
cuauucccuu ugucuugaag guuuuagagc uaugcugucc uu 42

<210> SEQ ID NO 334
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 334
ucuauucccu uugucuugaa gguuuuagag cuaugcuguc cuu            43

<210> SEQ ID NO 335
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 335
ucuauucccu uugucuugaa gguuuuagag cuaugcuguc cuu            43

<210> SEQ ID NO 336
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 336
ucuauucccu uugucuugaa gguuuuagag cuaugcuguc cuu            43

<210> SEQ ID NO 337
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 337
uucuauuccc uuugucuuga agguuuuaga gcuaugcugu ccuuuu         46

<210> SEQ ID NO 338
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 338
uucuauuccc uuugucuuga agguuuuaga gcuaugcugu ccuuuu         46

<210> SEQ ID NO 339
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 339
uucuauuccc uuugucuuga agguuuuaga gcuaugcugu ccuuuu         46

<210> SEQ ID NO 340
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 340
uuucuauucc cuuugucuug aagguuuuag agcuaugcug uccuuuu        47

<210> SEQ ID NO 341
<211> LENGTH: 47
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 341
uuucuauucc cuuugucuug aagguuuuag agcuaugcug uccuuuu                47

<210> SEQ ID NO 342
<211> LENGTH: 47
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 342
uuucuauucc cuuugucuug aagguuuuag agcuaugcug uccuuuu                47

<210> SEQ ID NO 343
<211> LENGTH: 47
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 343
uuucuauucc cuuugucuug aagguuuuag agcuaugcug uccuuuu                47

<210> SEQ ID NO 344
<211> LENGTH: 42
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 344
uucauugaca ugccaacaga guuuuagagc uaugcugucc uu                     42

<210> SEQ ID NO 345
<211> LENGTH: 43
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 345
uuucauugac augccaacag aguuuuagag cuaugcuguc cuu                    43

<210> SEQ ID NO 346
<211> LENGTH: 43
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 346
uuucauugac augccaacag aguuuuagag cuaugcuguc cuu                    43

```
<210> SEQ ID NO 347
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 347
uuucauugac augccaacag aguuuuagag cuaugcuguc cuu                      43

<210> SEQ ID NO 348
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 348
uuuucauuga caugccaaca gaguuuuaga gcuaugcugu ccuuuu                   46

<210> SEQ ID NO 349
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 349
uuuucauuga caugccaaca gaguuuuaga gcuaugcugu ccuuuu                   46

<210> SEQ ID NO 350
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 350
uuuucauuga caugccaaca gaguuuuaga gcuaugcugu ccuuuu                   46

<210> SEQ ID NO 351
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 351
uuuuucauug acaugccaac agaguuuuag agcuaugcug uccuuuu                  47

<210> SEQ ID NO 352
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 352
uuuuucauug acaugccaac agaguuuuag agcuaugcug uccuuuu                  47
```

```
<210> SEQ ID NO 353
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 353
uuuuucauug acaugccaac agaguuuuag agcuaugcug uccuuuu              47

<210> SEQ ID NO 354
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 354
uuuuucauug acaugccaac agaguuuuag agcuaugcug uccuuuu              47

<210> SEQ ID NO 355
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 355
cuaaaaggca gauggugaug                                            20

<210> SEQ ID NO 356
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 356
cuuccauaca uucucucuca                                            20

<210> SEQ ID NO 357
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 357
aaagggacac caacauucau                                            20

<210> SEQ ID NO 358
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 358
aagucgauau cccucaguac                                            20

<210> SEQ ID NO 359
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 359
gguggagaag augccaaacc                                                  20

<210> SEQ ID NO 360
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 360
uucugugcug gcuuccauga                                                  20

<210> SEQ ID NO 361
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 361
cuaaaaggca gauggugaug guuuuagagc uaugcugucc uu                         42

<210> SEQ ID NO 362
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 362
ucuaaaaggc agauggugau gguuuuagag cuaugcuguc cuu                        43

<210> SEQ ID NO 363
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 363
ucuaaaaggc agauggugau gguuuuagag cuaugcuguc cuu                        43

<210> SEQ ID NO 364
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 364
ucuaaaaggc agauggugau gguuuuagag cuaugcuguc cuu                        43

<210> SEQ ID NO 365
<211> LENGTH: 46
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 365
uucuaaaagg cagaugguga ugguuuuaga gcuaugcugu ccuuuu                    46

<210> SEQ ID NO 366
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 366
uucuaaaagg cagaugguga ugguuuuaga gcuaugcugu ccuuuu                    46

<210> SEQ ID NO 367
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 367
uucuaaaagg cagaugguga ugguuuuaga gcuaugcugu ccuuuu                    46

<210> SEQ ID NO 368
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 368
uuucuaaaag gcagauggug augguuuuag agcuaugcug uccuuuu                   47

<210> SEQ ID NO 369
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 369
uuucuaaaag gcagauggug augguuuuag agcuaugcug uccuuuu                   47

<210> SEQ ID NO 370
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 370
uuucuaaaag gcagauggug augguuuuag agcuaugcug uccuuuu                   47

<210> SEQ ID NO 371
<211> LENGTH: 47
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 371
uuucuaaaag gcagauggug augguuuuag agcuaugcug uccuuuu         47

<210> SEQ ID NO 372
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 372
cuuccauaca uucucucuca guuuuagagc uaugcugucc uu              42

<210> SEQ ID NO 373
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 373
ucuuccauac auucucucuc aguuuuagag cuaugcuguc cuu             43

<210> SEQ ID NO 374
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 374
ucuuccauac auucucucuc aguuuuagag cuaugcuguc cuu             43

<210> SEQ ID NO 375
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 375
ucuuccauac auucucucuc aguuuuagag cuaugcuguc cuu             43

<210> SEQ ID NO 376
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 376
uucuuccaua cauucucucu caguuuuaga gcuaugcugu ccuuuu          46

<210> SEQ ID NO 377
<211> LENGTH: 46
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 377
uucuuccaua cauucucucu caguuuuaga gcuaugcugu ccuuuu                    46

<210> SEQ ID NO 378
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 378
uucuuccaua cauucucucu caguuuuaga gcuaugcugu ccuuuu                    46

<210> SEQ ID NO 379
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 379
uuucuuccau acauucucuc ucaguuuuag agcuaugcug uccuuuu                   47

<210> SEQ ID NO 380
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 380
uuucuuccau acauucucuc ucaguuuuag agcuaugcug uccuuuu                   47

<210> SEQ ID NO 381
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 381
uuucuuccau acauucucuc ucaguuuuag agcuaugcug uccuuuu                   47

<210> SEQ ID NO 382
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 382
uuucuuccau acauucucuc ucaguuuuag agcuaugcug uccuuuu                   47

<210> SEQ ID NO 383
<211> LENGTH: 42
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 383
aaagggacac caacauucau guuuuagagc uaugcugucc uu                        42

<210> SEQ ID NO 384
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 384
uaaagggaca ccaacauuca uguuuuagag cuaugcuguc cuu                       43

<210> SEQ ID NO 385
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 385
uaaagggaca ccaacauuca uguuuuagag cuaugcuguc cuu                       43

<210> SEQ ID NO 386
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 386
uaaagggaca ccaacauuca uguuuuagag cuaugcuguc cuu                       43

<210> SEQ ID NO 387
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 387
uuaaagggac accaacauuc auguuuuaga gcuaugcugu ccuuuu                    46

<210> SEQ ID NO 388
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 388
uuaaagggac accaacauuc auguuuuaga gcuaugcugu ccuuuu                    46

<210> SEQ ID NO 389
<211> LENGTH: 46
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 389
uuaaagggac accaacauuc auguuuuaga gcuaugcugu ccuuuu          46

<210> SEQ ID NO 390
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 390
uuuaaaggga caccaacauu cauguuuuag agcuaugcug uccuuuu          47

<210> SEQ ID NO 391
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 391
uuuaaaggga caccaacauu cauguuuuag agcuaugcug uccuuuu          47

<210> SEQ ID NO 392
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 392
uuuaaaggga caccaacauu cauguuuuag agcuaugcug uccuuuu          47

<210> SEQ ID NO 393
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393
uuuaaaggga caccaacauu cauguuuuag agcuaugcug uccuuuu          47

<210> SEQ ID NO 394
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 394
aagucgauau cccucaguac guuuuagagc uaugcugucc uu              42

<210> SEQ ID NO 395
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 395
uaagucgaua ucccucagua cguuuuagag cuaugcuguc cuu              43

<210> SEQ ID NO 396
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 396
uaagucgaua ucccucagua cguuuuagag cuaugcuguc cuu              43

<210> SEQ ID NO 397
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 397
uaagucgaua ucccucagua cguuuuagag cuaugcuguc cuu              43

<210> SEQ ID NO 398
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 398
uuaagucgau aucccucagu acguuuuaga gcuaugcugu ccuuuu           46

<210> SEQ ID NO 399
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 399
uuaagucgau aucccucagu acguuuuaga gcuaugcugu ccuuuu           46

<210> SEQ ID NO 400
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 400
uuaagucgau aucccucagu acguuuuaga gcuaugcugu ccuuuu           46

<210> SEQ ID NO 401
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 401
uuuaagucga uaucccucag uacguuuuag agcuaugcug uccuuuu       47

<210> SEQ ID NO 402
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 402
uuuaagucga uaucccucag uacguuuuag agcuaugcug uccuuuu       47

<210> SEQ ID NO 403
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 403
uuuaagucga uaucccucag uacguuuuag agcuaugcug uccuuuu       47

<210> SEQ ID NO 404
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 404
uuuaagucga uaucccucag uacguuuuag agcuaugcug uccuuuu       47

<210> SEQ ID NO 405
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 405
gguggagaag augccaaacc guuuuagagc uaugcugucc uu       42

<210> SEQ ID NO 406
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 406
ugguggagaa gaugccaaac cguuuuagag cuaugcuguc cuu       43

<210> SEQ ID NO 407
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 407
ugguggagaa gaugccaaac cguuuuagag cuaugcuguc cuu    43

<210> SEQ ID NO 408
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 408
ugguggagaa gaugccaaac cguuuuagag cuaugcuguc cuu    43

<210> SEQ ID NO 409
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 409
uugguggaga agaugccaaa ccguuuuaga gcuaugcugu ccuuuu    46

<210> SEQ ID NO 410
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 410
uugguggaga agaugccaaa ccguuuuaga gcuaugcugu ccuuuu    46

<210> SEQ ID NO 411
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 411
uugguggaga agaugccaaa ccguuuuaga gcuaugcugu ccuuuu    46

<210> SEQ ID NO 412
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 412
uuugguggag aagaugccaa accguuuuag agcuaugcug uccuuuu    47

<210> SEQ ID NO 413
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 413
uuugguggag aagaugccaa accguuuuag agcuaugcug uccuuuu        47

<210> SEQ ID NO 414
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 414
uuugguggag aagaugccaa accguuuuag agcuaugcug uccuuuu        47

<210> SEQ ID NO 415
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 415
uuugguggag aagaugccaa accguuuuag agcuaugcug uccuuuu        47

<210> SEQ ID NO 416
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 416
uucugugcug gcuuccauga guuuuagagc uaugcugucc uu        42

<210> SEQ ID NO 417
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 417
uuucugugcu ggcuuccaug aguuuuagag cuaugcuguc cuu        43

<210> SEQ ID NO 418
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 418
uuucugugcu ggcuuccaug aguuuuagag cuaugcuguc cuu        43

<210> SEQ ID NO 419
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 419
uuucugugcu ggcuuccaug aguuuuagag cuaugcuguc cuu        43

<210> SEQ ID NO 420
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 420
uuuucugugc uggcuuccau gaguuuuaga gcuaugcugu ccuuuu        46

<210> SEQ ID NO 421
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 421
uuuucugugc uggcuuccau gaguuuuaga gcuaugcugu ccuuuu        46

<210> SEQ ID NO 422
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 422
uuuucugugc uggcuuccau gaguuuuaga gcuaugcugu ccuuuu        46

<210> SEQ ID NO 423
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 423
uuuuucugug cuggcuucca ugaguuuuag agcuaugcug uccuuuu        47

<210> SEQ ID NO 424
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 424
uuuuucugug cuggcuucca ugaguuuuag agcuaugcug uccuuuu        47

<210> SEQ ID NO 425
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 425
uuuuucugug cuggcuucca ugaguuuuag agcuaugcug uccuuuu        47

<210> SEQ ID NO 426
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 426
uuuuucugug cuggcuucca ugaguuuuag agcuaugcug uccuuuu                    47

<210> SEQ ID NO 427
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 427
cugaauuagc uguaucguca                                                 20

<210> SEQ ID NO 428
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 428
caaugaggga ccaguacaug                                                 20

<210> SEQ ID NO 429
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 429
agaacaaauu aaaagaguua                                                 20

<210> SEQ ID NO 430
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 430
aaucacauuu auuccuacu                                                  20

<210> SEQ ID NO 431
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 431
uucucgaacu aauguauaga                                                 20

<210> SEQ ID NO 432
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 432
gaauaugauc caacaauaga                                                  20

<210> SEQ ID NO 433
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 433
cugaauuagc uguaucguca guuuuagagc uaugcugucc uu                         42

<210> SEQ ID NO 434
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 434
ucugaauuag cuguaucguc aguuuuagag cuaugcuguc cuu                        43

<210> SEQ ID NO 435
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 435
ucugaauuag cuguaucguc aguuuuagag cuaugcuguc cuu                        43

<210> SEQ ID NO 436
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 436
ucugaauuag cuguaucguc aguuuuagag cuaugcuguc cuu                        43

<210> SEQ ID NO 437
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 437
uucugaauua gcuguaucgu caguuuuaga gcuaugcugu ccuuuu                     46

<210> SEQ ID NO 438

```
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 438
uucugaauua gcuguaucgu caguuuuaga gcuaugcugu ccuuuu          46

<210> SEQ ID NO 439
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 439
uucugaauua gcuguaucgu caguuuuaga gcuaugcugu ccuuuu          46

<210> SEQ ID NO 440
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 440
uuucugaauu agcuguaucg ucaguuuuag agcuaugcug uccuuuu         47

<210> SEQ ID NO 441
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 441
uuucugaauu agcuguaucg ucaguuuuag agcuaugcug uccuuuu         47

<210> SEQ ID NO 442
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 442
uuucugaauu agcuguaucg ucaguuuuag agcuaugcug uccuuuu         47

<210> SEQ ID NO 443
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 443
uuucugaauu agcuguaucg ucaguuuuag agcuaugcug uccuuuu         47

<210> SEQ ID NO 444
<211> LENGTH: 42
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 444
caaugaggga ccaguacaug guuuuagagc uaugcuqucc uu                          42

<210> SEQ ID NO 445
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 445
ucaaugaggg accaguacau gguuuuagag cuaugcuguc cuu                         43

<210> SEQ ID NO 446
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 446
ucaaugaggg accaguacau gguuuuagag cuaugcuguc cuu                         43

<210> SEQ ID NO 447
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 447
ucaaugaggg accaguacau gguuuuagag cuaugcuguc cuu                         43

<210> SEQ ID NO 448
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 448
uucaaugagg gaccaguaca ugguuuuaga gcuaugcugu ccuuuu                      46

<210> SEQ ID NO 449
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 449
uucaaugagg gaccaguaca ugguuuuaga gcuaugcugu ccuuuu                      46

<210> SEQ ID NO 450
<211> LENGTH: 46
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 450
uucaaugagg gaccaguaca ugguuuuaga gcuaugcugu ccuuuu        46

<210> SEQ ID NO 451
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 451
uuucaaugag ggaccaguac augguuuuag agcuaugcug uccuuuu        47

<210> SEQ ID NO 452
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 452
uuucaaugag ggaccaguac augguuuuag agcuaugcug uccuuuu        47

<210> SEQ ID NO 453
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 453
uuucaaugag ggaccaguac augguuuuag agcuaugcug uccuuuu        47

<210> SEQ ID NO 454
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 454
uuucaaugag ggaccaguac augguuuuag agcuaugcug uccuuuu        47

<210> SEQ ID NO 455
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 455
agaacaaauu aaaagaguua guuuuagagc uaugcugucc uu        42

<210> SEQ ID NO 456
<211> LENGTH: 43
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 456
uagaacaaau uaaaagaguu aguuuagag cuaugcuguc cuu                    43

<210> SEQ ID NO 457
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 457
uagaacaaau uaaaagaguu aguuuagag cuaugcuguc cuu                    43

<210> SEQ ID NO 458
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 458
uagaacaaau uaaaagaguu aguuuagag cuaugcuguc cuu                    43

<210> SEQ ID NO 459
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 459
uuagaacaaa uuaaaagagu uaguuuaga gcuaugcugu ccuuuu                 46

<210> SEQ ID NO 460
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 460
uuagaacaaa uuaaaagagu uaguuuaga gcuaugcugu ccuuuu                 46

<210> SEQ ID NO 461
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 461
uuagaacaaa uuaaaagagu uaguuuaga gcuaugcugu ccuuuu                 46

<210> SEQ ID NO 462
<211> LENGTH: 47
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 462
uuuagaacaa auuaaaagag uuaguuuuag agcuaugcug uccuuuu                   47

<210> SEQ ID NO 463
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 463
uuuagaacaa auuaaaagag uuaguuuuag agcuaugcug uccuuuu                   47

<210> SEQ ID NO 464
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 464
uuuagaacaa auuaaaagag uuaguuuuag agcuaugcug uccuuuu                   47

<210> SEQ ID NO 465
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 465
uuuagaacaa auuaaaagag uuaguuuuag agcuaugcug uccuuuu                   47

<210> SEQ ID NO 466
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 466
aaucacauuu auuccuacu guuuuagagc uaugcuguucc uu                        42

<210> SEQ ID NO 467
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 467
uaaucacauu uauuccuac uguuuuagag cuaugcuguc cuu                        43

<210> SEQ ID NO 468
<211> LENGTH: 43
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 468
uaaucacauu uauuccuac uguuuuagag cuaugcuguc cuu        43

<210> SEQ ID NO 469
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 469
uaaucacauu uauuccuac uguuuuagag cuaugcuguc cuu        43

<210> SEQ ID NO 470
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 470
uuaaucacau uuauuuccua cuguuuuaga gcuaugcugu ccuuuu        46

<210> SEQ ID NO 471
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 471
uuaaucacau uuauuuccua cuguuuuaga gcuaugcugu ccuuuu        46

<210> SEQ ID NO 472
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 472
uuaaucacau uuauuuccua cuguuuuaga gcuaugcugu ccuuuu        46

<210> SEQ ID NO 473
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 473
uuuaaucaca uuuauuuccu acuguuuuag agcuaugcug uccuuuu        47

<210> SEQ ID NO 474
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 474
uuuaaucaca uuuauuuccu acuguuuuag agcuaugcug uccuuuu          47

<210> SEQ ID NO 475
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 475
uuuaaucaca uuuauuuccu acuguuuuag agcuaugcug uccuuuu          47

<210> SEQ ID NO 476
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 476
uuuaaucaca uuuauuuccu acuguuuuag agcuaugcug uccuuuu          47

<210> SEQ ID NO 477
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 477
uucucgaacu aauguauaga guuuuagagc uaugcugucc uu               42

<210> SEQ ID NO 478
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 478
uuucucgaac uaauguauag aguuuuagag cuaugcuguc cuu              43

<210> SEQ ID NO 479
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 479
uuucucgaac uaauguauag aguuuuagag cuaugcuguc cuu              43

<210> SEQ ID NO 480
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 480
uuucucgaac uaauguauag aguuuuagag cuaugcuguc cuu        43

<210> SEQ ID NO 481
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 481
uuuucucgaa cuaauguaua gaguuuuaga gcuaugcugu ccuuuu        46

<210> SEQ ID NO 482
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 482
uuuucucgaa cuaauguaua gaguuuuaga gcuaugcugu ccuuuu        46

<210> SEQ ID NO 483
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 483
uuuucucgaa cuaauguaua gaguuuuaga gcuaugcugu ccuuuu        46

<210> SEQ ID NO 484
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 484
uuuuucucga acuaauguau agaguuuuag agcuaugcug uccuuuu        47

<210> SEQ ID NO 485
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 485
uuuuucucga acuaauguau agaguuuuag agcuaugcug uccuuuu        47

<210> SEQ ID NO 486
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 486
uuuuucucga acuaauguau agaguuuuag agcuaugcug uccuuuu    47

<210> SEQ ID NO 487
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 487
uuuuucucga acuaauguau agaguuuuag agcuaugcug uccuuuu    47

<210> SEQ ID NO 488
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 488
gaauaugauc caacaauaga guuuuagagc uaugcugucc uu    42

<210> SEQ ID NO 489
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 489
ugaauaugau ccaacaauag aguuuuagag cuaugcuguc cuu    43

<210> SEQ ID NO 490
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 490
ugaauaugau ccaacaauag aguuuuagag cuaugcuguc cuu    43

<210> SEQ ID NO 491
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 491
ugaauaugau ccaacaauag aguuuuagag cuaugcuguc cuu    43

<210> SEQ ID NO 492
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 492
uugaauauga uccaacaaua gaguuuuaga gcuaugcugu ccuuuu        46

<210> SEQ ID NO 493
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 493
uugaauauga uccaacaaua gaguuuuaga gcuaugcugu ccuuuu        46

<210> SEQ ID NO 494
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 494
uugaauauga uccaacaaua gaguuuuaga gcuaugcugu ccuuuu        46

<210> SEQ ID NO 495
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 495
uuugaauaug auccaacaau agaguuuuag agcuaugcug uccuuuu       47

<210> SEQ ID NO 496
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 496
uuugaauaug auccaacaau agaguuuuag agcuaugcug uccuuuu       47

<210> SEQ ID NO 497
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 497
uuugaauaug auccaacaau agaguuuuag agcuaugcug uccuuuu       47

<210> SEQ ID NO 498
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 498
uuugaauaug auccaacaau agaguuuuag agcuaugcug uccuuuu       47

<210> SEQ ID NO 499
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 499
uuuucugcug ccccaugggg                                              20

<210> SEQ ID NO 500
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 500
cctccccatg gggcagcaga aaa                                          23

<210> SEQ ID NO 501
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 501
ttttctgctg ccccatgggg agg                                          23

<210> SEQ ID NO 502
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 502
acacaaguuc accagcagaa                                              20

<210> SEQ ID NO 503
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 503
cctttctgct ggtgaacttg tgt                                          23

<210> SEQ ID NO 504
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 504
acacaagttc accagcagaa agg                                          23

<210> SEQ ID NO 505
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 505
gctgaactcg aggtctgggg                                              20

<210> SEQ ID NO 506
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 506
cctccccaga cctcgagttc agc                                          23

<210> SEQ ID NO 507
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 507
gctgaactcg aggtctgggg agg                                          23

<210> SEQ ID NO 508
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 508
uuucuaucuu uuuuaauuag                                              20

<210> SEQ ID NO 509
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 509
cctctaatta aaaagatag aaa                                           23

<210> SEQ ID NO 510
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 510
tttctatctt ttttaattag agg                                          23

```
<210> SEQ ID NO 511
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 511
uuuucugcug ccccaugggg                                                     20

<210> SEQ ID NO 512
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 512
acacaaguuc accagcagaa                                                     20

<210> SEQ ID NO 513
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 513
gctgaactcg aggtctgggg                                                     20

<210> SEQ ID NO 514
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 514
uuucuaucuu uuuuaauuag                                                     20

<210> SEQ ID NO 515
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 515
uuuucugcug ccccaugggg guuuuagagc uaugcugucc uu                            42

<210> SEQ ID NO 516
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 516
uuuuucugcu gccccauggg gguuuuagag cuaugcuguc cuu                           43

<210> SEQ ID NO 517
```

```
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 517
uuuuucugcu gccccauggg gguuuuagag cuaugcuguc cuu                        43

<210> SEQ ID NO 518
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 518
uuuuucugcu gccccauggg gguuuuagag cuaugcuguc cuu                        43

<210> SEQ ID NO 519
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 519
uuuuuucugc ugccccaugg ggguuuuaga gcuaugcugu ccuuuu                     46

<210> SEQ ID NO 520
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 520
uuuuuucugc ugccccaugg ggguuuuaga gcuaugcugu ccuuuu                     46

<210> SEQ ID NO 521
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 521
uuuuuucugc ugccccaugg ggguuuuaga gcuaugcugu ccuuuu                     46

<210> SEQ ID NO 522
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 522
uuuuuuucug cugccccaug ggggpuuuag agcuaugcug uccuuuu                    47

<210> SEQ ID NO 523
<211> LENGTH: 47
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 523
uuuuuuucug cugccccaug ggggutuuag agcuaugcug uccuuuu        47

<210> SEQ ID NO 524
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 524
uuuuuuucug cugccccaug ggggutuuag agcuaugcug uccuuuu        47

<210> SEQ ID NO 525
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 525
uuuuuuucug cugccccaug ggggutuuag agcuaugcug uccuuuu        47

<210> SEQ ID NO 526
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 526
acacaaguuc accagcagaa guuuuagagc uaugcugucc uu        42

<210> SEQ ID NO 527
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 527
uacacaaguu caccagcaga aguuuuagag cuaugcuguc cuu        43

<210> SEQ ID NO 528
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 528
uacacaaguu caccagcaga aguuuuagag cuaugcuguc cuu        43

<210> SEQ ID NO 529
<211> LENGTH: 43
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 529
uacacaaguu caccagcaga aguuuuagag cuaugcuguc cuu                     43

<210> SEQ ID NO 530
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 530
uuacacaagu ucaccagcag aaguuuuaga gcuaugcugu ccuuuu                  46

<210> SEQ ID NO 531
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 531
uuacacaagu ucaccagcag aaguuuuaga gcuaugcugu ccuuuu                  46

<210> SEQ ID NO 532
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 532
uuacacaagu ucaccagcag aaguuuuaga gcuaugcugu ccuuuu                  46

<210> SEQ ID NO 533
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 533
uuuacacaag uucaccagca gaaguuuuag agcuaugcug uccuuuu                 47

<210> SEQ ID NO 534
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 534
uuuacacaag uucaccagca gaaguuuuag agcuaugcug uccuuuu                 47

<210> SEQ ID NO 535
<211> LENGTH: 47
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 535
uuuacacaag uucaccagca gaaguuuuag agcuaugcug uccuuuu                    47

<210> SEQ ID NO 536
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 536
uuuacacaag uucaccagca gaaguuuuag agcuaugcug uccuuuu                    47

<210> SEQ ID NO 537
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 537
gctgaactcg aggtctgggg guuuuagagc uaugcugucc uu                         42

<210> SEQ ID NO 538
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 538
ugctgaactc gaggtctggg gguuuuagag cuaugcuguc cuu                        43

<210> SEQ ID NO 539
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 539
ugctgaactc gaggtctggg gguuuuagag cuaugcuguc cuu                        43

<210> SEQ ID NO 540
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 540
ugctgaactc gaggtctggg gguuuuagag cuaugcuguc cuu        43

<210> SEQ ID NO 541
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 541
uugcugaacu cgaggucugg ggguuuuaga gcuaugcugu ccuuuu        46

<210> SEQ ID NO 542
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 542
uugcugaacu cgaggucugg ggguuuuaga gcuaugcugu ccuuuu        46

<210> SEQ ID NO 543
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 543
uuugcugaac ucgaggucug ggggguuuag agcuaugcug uccuuuu        47

<210> SEQ ID NO 544
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 544
uuugcugaac ucgaggucug ggggguuuag agcuaugcug uccuuuu        47

<210> SEQ ID NO 545
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 545
uuugctgaac tcgaggtctg ggggguuuag agcuaugcug uccuuuu            47

<210> SEQ ID NO 546
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 546
uuugctgaac tcgaggtctg ggggguuuag agcuaugcug uccuuuu            47

<210> SEQ ID NO 547
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 547
uuugctgaac tcgaggtctg ggggguuuag agcuaugcug uccuuuu            47

<210> SEQ ID NO 548
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 548
uuucuaucuu uuuuaauuag guuuuagagc uaugcugucc uu                 42

<210> SEQ ID NO 549
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 549
uuuucuaucu uuuuuaauua gguuuuagag cuaugcuguc cuu                43

<210> SEQ ID NO 550
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 550
uuuucuaucu uuuuuaauua gguuuuagag cuaugcuguc cuu                43
```

```
<210> SEQ ID NO 551
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 551
uuuucuaucu uuuuuaauua gguuuuagag cuaugcuguc cuu                     43

<210> SEQ ID NO 552
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 552
uuuuucuauc uuuuuuaauu agguuuuaga gcuaugcugu ccuuuu                  46

<210> SEQ ID NO 553
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 553
uuuuucuauc uuuuuuaauu agguuuuaga gcuaugcugu ccuuuu                  46

<210> SEQ ID NO 554
<211> LENGTH: 46
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 554
uuuuucuauc uuuuuuaauu agguuuuaga gcuaugcugu ccuuuu                  46

<210> SEQ ID NO 555
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 555
uuuuuucuau cuuuuuuaau uagguuuuag agcuaugcug uccuuuu                 47

<210> SEQ ID NO 556
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 556
uuuuuucuau cuuuuuuaau uagguuuuag agcuaugcug uccuuuu                 47

<210> SEQ ID NO 557
```

```
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 557
uuuuuucuau cuuuuuuaau uagguuuuag agcuaugcug uccuuuu                47

<210> SEQ ID NO 558
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 558
uuuuuucuau cuuuuuuaau uagguuuuag agcuaugcug uccuuuu                47

<210> SEQ ID NO 559
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 559
acaactggta agaaggagtg ac                                          22

<210> SEQ ID NO 560
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 560
ccttgggttt tgggtgatcc                                             20

<210> SEQ ID NO 561
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 561
tcgacactta cgttcctgat                                             20

<210> SEQ ID NO 562
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 562
catacttgac ctctgcctac                                             20

<210> SEQ ID NO 563
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 563
gatgacagcc gtggtggaat                                              20

<210> SEQ ID NO 564
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 564
cctattccac cacggctgtc atc                                          23

<210> SEQ ID NO 565
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 565
gatgacagcc gtggtggaat agg                                          23

<210> SEQ ID NO 566
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 566
gccgcatggg ctcacaactg                                              20

<210> SEQ ID NO 567
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 567
cctcagttgt gagcccatgc ggc                                          23

<210> SEQ ID NO 568
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 568
gccgcatggg ctcacaactg agg                                          23

<210> SEQ ID NO 569
<211> LENGTH: 20
<212> TYPE: DNA
```

<213> ORGANISM: Artificial Sequence
<220> FEATURE:
<223> OTHER INFORMATION: Description of Artificial Sequence: Synthetic oligonucleotide

<400> SEQUENCE: 569
tggactggta tttgtgtctg                                          20

<210> SEQ ID NO 570
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 570
cctcagacac aaataccagt cca                                      23

<210> SEQ ID NO 571
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 571
tggactggta tttgtgtctg agg                                      23

<210> SEQ ID NO 572
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 572
gatgacagcc gugguggaau guuuuagagc uaugcugucc uu                 42

<210> SEQ ID NO 573
<211> LENGTH: 43
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 573
ugaugacagc cgugguggaa uguuuuagag cuaugcuguc cuu                43

<210> SEQ ID NO 574
<211> LENGTH: 43
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 574
ugaugacagc cgugguggaa uguuuuagag cuaugcuguc cuu                43

<210> SEQ ID NO 575

```
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 575
ugaugacagc cgugguggaa uguuuuagag cuaugcuguc cuu                          43

<210> SEQ ID NO 576
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 576
uuugaugaca gccguggugg aauguuuuag agcuaugcug uccuuuu                      47

<210> SEQ ID NO 577
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 577
uuugaugaca gccguggugg aauguuuuag agcuaugcug uccuuuu                      47

<210> SEQ ID NO 578
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 578
uuugaugaca gccguggugg aauguuuuag agcuaugcug uccuuuu                      47

<210> SEQ ID NO 579
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 579
uuugaugaca gccguggugg aauguuuuag agcuaugcug uccuuuu                      47

<210> SEQ ID NO 580
<211> LENGTH: 48
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 580
uuuggaugac agccguggug gaauguuuua gagcuaugcu guccuuuu                     48

<210> SEQ ID NO 581
<211> LENGTH: 47
```

```
<210> SEQ ID NO 581
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 581
uuugaugaca gccguggugg aauguuuuag agcuaugcug uccuuuu                   47

<210> SEQ ID NO 582
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 582
uuugaugaca gccguggugg aauguuuuag agcuaugcug uccuuuu                   47

<210> SEQ ID NO 583
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 583
gccgcauggg cucacaacug guuuuagagc uaugcugucc uu                        42

<210> SEQ ID NO 584
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 584
ugccgcaugg gcucacaacu gguuuuagag cuaugcuguc cuu                       43

<210> SEQ ID NO 585
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 585
ugccgcaugg gcucacaacu gguuuuagag cuaugcuguc cuu                       43

<210> SEQ ID NO 586
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 586
ugccgcaugg gcucacaacu gguuuuagag cuaugcuguc cuu                       43

<210> SEQ ID NO 587
<211> LENGTH: 47
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 587
uuugccgcau gggcucacaa cugguuuuag agcuaugcug uccuuuu                47

<210> SEQ ID NO 588
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 588
uuugccgcau gggcucacaa cugguuuuag agcuaugcug uccuuuu                47

<210> SEQ ID NO 589
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 589
uuugccgcau gggcucacaa cugguuuuag agcuaugcug uccuuuu                47

<210> SEQ ID NO 590
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 590
uuugccgcau gggcucacaa cugguuuuag agcuaugcug uccuuuu                47

<210> SEQ ID NO 591
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 591
uuugccgcau gggcucacaa cugguuuuag agcuaugcug uccuuuu                47

<210> SEQ ID NO 592
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 592
uuugccgcau gggcucacaa cugguuuuag agcuaugcug uccuuuu                47

<210> SEQ ID NO 593
<211> LENGTH: 47
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 593
uuugccgcau gggcucacaa cugguuuuag agcuaugcug uccuuuu         47

<210> SEQ ID NO 594
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 594
uggacuggua uuugugucug guuuuagagc uaugcugucc uu              42

<210> SEQ ID NO 595
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 595
uuggacuggu auuugugucu gguuuuagag cuaugcuguc cuu             43

<210> SEQ ID NO 596
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 596
uuggacuggu auuugugucu gguuuuagag cuaugcuguc cuu             43

<210> SEQ ID NO 597
<211> LENGTH: 43
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 597
uuggacuggu auuugugucu gguuuuagag cuaugcuguc cuu             43

<210> SEQ ID NO 598
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 598
uuuuggacug guauuugugu cugguuuuag agcuaugcug uccuuuu         47

<210> SEQ ID NO 599
<211> LENGTH: 47
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 599
uuuuggacug guauuugugu cugguuuuag agcuaugcug uccuuuu                    47

<210> SEQ ID NO 600
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 600
uuuuggacug guauuugugu cugguuuuag agcuaugcug uccuuuu                    47

<210> SEQ ID NO 601
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 601
uuuuggacug guauuugugu cugguuuuag agcuaugcug uccuuuu                    47

<210> SEQ ID NO 602
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 602
uuuuggacug guauuugugu cugguuuuag agcuaugcug uccuuuu                    47

<210> SEQ ID NO 603
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 603
uuuuggacug guauuugugu cugguuuuag agcuaugcug uccuuuu                    47

<210> SEQ ID NO 604
<211> LENGTH: 47
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 604
uuuuggacug guauuugugu cugguuuuag agcuaugcug uccuuuu                    47

<210> SEQ ID NO 605
<211> LENGTH: 16
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 605
guuuuagagc uaugcu                                                    16

<210> SEQ ID NO 606
<211> LENGTH: 67
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 606
agcauagcaa guuaaaauaa ggcuaguccg uuaucaacuu gaaaaagugg caccgagucg    60
gugcuuu                                                              67

<210> SEQ ID NO 607
<211> LENGTH: 23
<212> TYPE: DNA
<213> ORGANISM: Homo sapiens
<220> FEATURE:
<221> NAME/KEY: modified_base
<222> LOCATION: (21)..(21)
<223> OTHER INFORMATION: a, c, t, g, unknown or other

<400> SEQUENCE: 607
aagggagaag ccagagatcc ngg                                            23

<210> SEQ ID NO 608
<211> LENGTH: 23
<212> TYPE: DNA
<213> ORGANISM: Homo sapiens
<220> FEATURE:
<221> NAME/KEY: modified_base
<222> LOCATION: (21)..(21)
<223> OTHER INFORMATION: a, c, t, g, unknown or other

<400> SEQUENCE: 608
gccagagatc ctggaagacc ngg                                            23

<210> SEQ ID NO 609
<211> LENGTH: 23
<212> TYPE: DNA
<213> ORGANISM: Homo sapiens
<220> FEATURE:
<221> NAME/KEY: modified_base
<222> LOCATION: (21)..(21)
<223> OTHER INFORMATION: a, c, t, g, unknown or other

<400> SEQUENCE: 609
ccagagatcc tggaagaccc ngg                                            23

<210> SEQ ID NO 610
<211> LENGTH: 23
<212> TYPE: DNA
<213> ORGANISM: Homo sapiens
<220> FEATURE:
<221> NAME/KEY: modified_base
<222> LOCATION: (21)..(21)
<223> OTHER INFORMATION: a, c, t, g, unknown or other

<400> SEQUENCE: 610
cagagatcct ggaagacccg ngg                                            23

<210> SEQ ID NO 611

```
<211> LENGTH: 23
<212> TYPE: DNA
<213> ORGANISM: Homo sapiens
<220> FEATURE:
<221> NAME/KEY: modified_base
<222> LOCATION: (21)..(21)
<223> OTHER INFORMATION: a, c, t, g, unknown or other

<400> SEQUENCE: 611
ctggcttctc ccttctctcc ngg                                              23

<210> SEQ ID NO 612
<211> LENGTH: 28
<212> TYPE: DNA
<213> ORGANISM: Homo sapiens
<220> FEATURE:
<221> NAME/KEY: modified_base
<222> LOCATION: (21)..(24)
<223> OTHER INFORMATION: a, c, t, g, unknown or other

<400> SEQUENCE: 612
aaactatgca aaatcctaat nnnngatt                                         28

<210> SEQ ID NO 613
<211> LENGTH: 23
<212> TYPE: DNA
<213> ORGANISM: Homo sapiens
<220> FEATURE:
<221> NAME/KEY: modified_base
<222> LOCATION: (21)..(21)
<223> OTHER INFORMATION: a, c, t, g, unknown or other

<400> SEQUENCE: 613
tgatacatta gcttcctacc ngg                                              23

<210> SEQ ID NO 614
<211> LENGTH: 27
<212> TYPE: DNA
<213> ORGANISM: Homo sapiens
<220> FEATURE:
<221> NAME/KEY: modified_base
<222> LOCATION: (25)..(25)
<223> OTHER INFORMATION: a, c, t, g, unknown or other

<400> SEQUENCE: 614
gcgcaatgtg actgctgaca aagangg                                          27

<210> SEQ ID NO 615
<211> LENGTH: 25
<212> TYPE: DNA
<213> ORGANISM: Homo sapiens
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: misc_feature
<222> LOCATION: (24)..(25)
<223> OTHER INFORMATION: May or may not be present

<400> SEQUENCE: 615
gcaccagccg ggagtcggga nggng                                            25

<210> SEQ ID NO 616
<211> LENGTH: 23
```

<212> TYPE: DNA
<213> ORGANISM: Homo sapiens
<220> FEATURE:
<221> NAME/KEY: modified_base
<222> LOCATION: (21)..(21)
<223> OTHER INFORMATION: a, c, t, g, unknown or other

<400> SEQUENCE: 616
tgaagcacca gccgggagtc ngg                                              23

<210> SEQ ID NO 617
<211> LENGTH: 23
<212> TYPE: DNA
<213> ORGANISM: Homo sapiens
<220> FEATURE:
<221> NAME/KEY: modified_base
<222> LOCATION: (21)..(21)
<223> OTHER INFORMATION: a, c, t, g, unknown or other

<400> SEQUENCE: 617
ctgaagcacc agccgggagt ngg                                              23

<210> SEQ ID NO 618
<211> LENGTH: 23
<212> TYPE: DNA
<213> ORGANISM: Homo sapiens
<220> FEATURE:
<221> NAME/KEY: modified_base
<222> LOCATION: (21)..(21)
<223> OTHER INFORMATION: a, c, t, g, unknown or other

<400> SEQUENCE: 618
cgactcccgg ctggtgcttc ngg                                              23

<210> SEQ ID NO 619
<211> LENGTH: 25
<212> TYPE: DNA
<213> ORGANISM: Homo sapiens
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: misc_feature
<222> LOCATION: (24)..(25)
<223> OTHER INFORMATION: May or may not be present

<400> SEQUENCE: 619
gcaccttccc gactcccggc nggng                                            25

<210> SEQ ID NO 620
<211> LENGTH: 23
<212> TYPE: DNA
<213> ORGANISM: Homo sapiens
<220> FEATURE:
<221> NAME/KEY: modified_base
<222> LOCATION: (21)..(21)
<223> OTHER INFORMATION: a, c, t, g, unknown or other

<400> SEQUENCE: 620
atctgcacct tcccgactcc ngg                                              23

<210> SEQ ID NO 621
<211> LENGTH: 25
<212> TYPE: DNA

```
<213> ORGANISM: Homo sapiens
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: misc_feature
<222> LOCATION: (24)..(25)
<223> OTHER INFORMATION: May or may not be present

<400> SEQUENCE: 621
gataatatca aacacgtcct nggng                                      25

<210> SEQ ID NO 622
<211> LENGTH: 23
<212> TYPE: DNA
<213> ORGANISM: Homo sapiens
<220> FEATURE:
<221> NAME/KEY: modified_base
<222> LOCATION: (21)..(21)
<223> OTHER INFORMATION: a, c, t, g, unknown or other

<400> SEQUENCE: 622
aatatcaaac acgtcctggg ngg                                        23

<210> SEQ ID NO 623
<211> LENGTH: 23
<212> TYPE: DNA
<213> ORGANISM: Homo sapiens
<220> FEATURE:
<221> NAME/KEY: modified_base
<222> LOCATION: (21)..(21)
<223> OTHER INFORMATION: a, c, t, g, unknown or other

<400> SEQUENCE: 623
acttccatct ggccacctcc ngg                                        23

<210> SEQ ID NO 624
<211> LENGTH: 23
<212> TYPE: DNA
<213> ORGANISM: Homo sapiens
<220> FEATURE:
<221> NAME/KEY: modified_base
<222> LOCATION: (21)..(21)
<223> OTHER INFORMATION: a, c, t, g, unknown or other

<400> SEQUENCE: 624
tctcagattt tacttccatc ngg                                        23

<210> SEQ ID NO 625
<211> LENGTH: 29
<212> TYPE: DNA
<213> ORGANISM: Homo sapiens
<220> FEATURE:
<221> NAME/KEY: modified_base
<222> LOCATION: (25)..(26)
<223> OTHER INFORMATION: a, c, t, g, unknown or other

<400> SEQUENCE: 625
catctggcca cctcctggtt tatgnngrr                                  29

<210> SEQ ID NO 626
<211> LENGTH: 25
<212> TYPE: DNA
<213> ORGANISM: Homo sapiens
```

```
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: misc_feature
<222> LOCATION: (24)..(25)
<223> OTHER INFORMATION: May or may not be present

<400> SEQUENCE: 626
gagacattgc tgagatgcca nggng                                 25

<210> SEQ ID NO 627
<211> LENGTH: 23
<212> TYPE: DNA
<213> ORGANISM: Homo sapiens
<220> FEATURE:
<221> NAME/KEY: modified_base
<222> LOCATION: (21)..(21)
<223> OTHER INFORMATION: a, c, t, g, unknown or other

<400> SEQUENCE: 627
tggtctaccc ttggacctag ngg                                   23

<210> SEQ ID NO 628
<211> LENGTH: 24
<212> TYPE: DNA
<213> ORGANISM: Homo sapiens
<220> FEATURE:
<221> NAME/KEY: modified_base
<222> LOCATION: (22)..(22)
<223> OTHER INFORMATION: a, c, t, g, unknown or other

<400> SEQUENCE: 628
tcagaggttc tttgagtcct tngg                                  24

<210> SEQ ID NO 629
<211> LENGTH: 25
<212> TYPE: DNA
<213> ORGANISM: Homo sapiens
<220> FEATURE:
<221> NAME/KEY: modified_base
<222> LOCATION: (21)..(22)
<223> OTHER INFORMATION: a, c, t, g, unknown or other

<400> SEQUENCE: 629
cccttggacc tagaggttct nngrr                                 25

<210> SEQ ID NO 630
<211> LENGTH: 23
<212> TYPE: DNA
<213> ORGANISM: Homo sapiens
<220> FEATURE:
<221> NAME/KEY: modified_base
<222> LOCATION: (21)..(21)
<223> OTHER INFORMATION: a, c, t, g, unknown or other

<400> SEQUENCE: 630
tcaaagaacc tcttggtcca ngg                                   23

<210> SEQ ID NO 631
<211> LENGTH: 23
<212> TYPE: DNA
<213> ORGANISM: Homo sapiens
<220> FEATURE:
```

```
<221> NAME/KEY: modified_base
<222> LOCATION: (21)..(21)
<223> OTHER INFORMATION: a, c, t, g, unknown or other

<400> SEQUENCE: 631
caaagaacct cttggtccaa ngg                                        23

<210> SEQ ID NO 632
<211> LENGTH: 25
<212> TYPE: DNA
<213> ORGANISM: Homo sapiens
<220> FEATURE:
<221> NAME/KEY: modified_base
<222> LOCATION: (21)..(22)
<223> OTHER INFORMATION: a, c, t, g, unknown or other

<400> SEQUENCE: 632
ctcaaagaac ctcttggtcc nngrr                                      25

<210> SEQ ID NO 633
<211> LENGTH: 23
<212> TYPE: DNA
<213> ORGANISM: Homo sapiens
<220> FEATURE:
<221> NAME/KEY: modified_base
<222> LOCATION: (21)..(21)
<223> OTHER INFORMATION: a, c, t, g, unknown or other

<400> SEQUENCE: 633
agcggttagg cgtacggccs ngg                                        23

<210> SEQ ID NO 634
<211> LENGTH: 23
<212> TYPE: DNA
<213> ORGANISM: Homo sapiens
<220> FEATURE:
<221> NAME/KEY: modified_base
<222> LOCATION: (21)..(21)
<223> OTHER INFORMATION: a, c, t, g, unknown or other

<400> SEQUENCE: 634
aggcgtacgg ccsgggctat ngg                                        23

<210> SEQ ID NO 635
<211> LENGTH: 25
<212> TYPE: DNA
<213> ORGANISM: Homo sapiens
<220> FEATURE:
<221> NAME/KEY: modified_base
<222> LOCATION: (21)..(22)
<223> OTHER INFORMATION: a, c, t, g, unknown or other

<400> SEQUENCE: 635
cgtacggccs gggctattgg nngrr                                      25

<210> SEQ ID NO 636
<211> LENGTH: 25
<212> TYPE: DNA
<213> ORGANISM: Homo sapiens
<220> FEATURE:
<221> NAME/KEY: modified_base
<222> LOCATION: (21)..(22)
<223> OTHER INFORMATION: a, c, t, g, unknown or other

<400> SEQUENCE: 636
cggccsgggc tattggttga nngrr                                      25
```

```
<210> SEQ ID NO 637
<211> LENGTH: 25
<212> TYPE: DNA
<213> ORGANISM: Homo sapiens
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: misc_feature
<222> LOCATION: (24)..(25)
<223> OTHER INFORMATION: May or may not be present

<400> SEQUENCE: 637
aagatcaaag tgctgagctc nggng                               25

<210> SEQ ID NO 638
<211> LENGTH: 23
<212> TYPE: DNA
<213> ORGANISM: Homo sapiens
<220> FEATURE:
<221> NAME/KEY: modified_base
<222> LOCATION: (21)..(21)
<223> OTHER INFORMATION: a, c, t, g, unknown or other

<400> SEQUENCE: 638
gtgctgagct ccggtgcgtt ngg                                 23

<210> SEQ ID NO 639
<211> LENGTH: 25
<212> TYPE: DNA
<213> ORGANISM: Homo sapiens
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: misc_feature
<222> LOCATION: (24)..(25)
<223> OTHER INFORMATION: May or may not be present

<400> SEQUENCE: 639
gagctccggt gcgttcggca nggng                               25

<210> SEQ ID NO 640
<211> LENGTH: 25
<212> TYPE: DNA
<213> ORGANISM: Homo sapiens
<220> FEATURE:
<221> NAME/KEY: modified_base
<222> LOCATION: (21)..(22)
<223> OTHER INFORMATION: a, c, t, g, unknown or other

<400> SEQUENCE: 640
agctcagcac tttgatcttt nngrr                               25

<210> SEQ ID NO 641
<211> LENGTH: 23
<212> TYPE: DNA
<213> ORGANISM: Homo sapiens
<220> FEATURE:
<221> NAME/KEY: modified_base
<222> LOCATION: (21)..(21)
```

```
<223> OTHER INFORMATION: a, c, t, g, unknown or other

<400> SEQUENCE: 641
cttgtggtag ttggagcttg ngg                                           23
```

ALLELE SELECTIVE GENE EDITING AND USES THEREOF

SEQUENCE LISTING

This application includes a Sequence Listing submitted electronically as an ASCII file created on Oct. 7, 2016, named ARC5237US_SL.txt, which is 153,879 bytes in size, and is hereby incorporated by reference in its entirety.

BACKGROUND OF THE INVENTION

Gene editing that is specific for a predetermined site can be done with the target-guided nuclease Cas9 and polynucleotide repair methods. Using the target-guided Cas9 endonuclease, both strands of a double stranded DNA can be cut near a target site to create a double-strand break.

The target specificity of Cas9 is determined by a guide molecule, which complexes Cas9 to the polynucleotide target. Polynucleotide target sequences, typically 17-20 bases in length, must be flanked by a 3' protospacer-adjacent motif (PAM). The structure of PAM is determined by the species of bacteria from which the Cas9 was derived. Fortuitously, suitable target sequences containing a PAM can be found in most genes of interest in most species. In one variation, the guide molecule can be made as a single RNA strand that has a sequence complementary to the target, which is attached to a bacterially-derived crispr-tracr RNA sequence that complexes Cas9.

In some modalities, after forming a double-strand break in dsDNA at a specific site, the break can be repaired to achieve editing of the DNA. A double-strand break can be repaired by non-homologous end joining (NHEJ) to generate random insertions and deletions. A double-strand break can also be repaired by homology-directed repair (HDR) using an exogenous DNA template to generate controlled insertions, deletions, and substitutions.

A major drawback of gene editing with Cas9 is that the guide molecule may have limited effectiveness for a target polynucleotide. The specificity and activity of a guide molecule can be unpredictable. Guide molecules for Cas9 editing can vary widely in effectiveness, and some guides that otherwise follow the structural scheme can be ineffective.

A further drawback of gene editing with Cas9 is that the guide molecule may lack selectivity for a target allele. Variations in the genome can contribute to disease conditions. Some alleles related to disease phenotypes have been identified in medical genetics. The inability to target particular alleles is a significant drawback of current methods for of gene editing.

Other drawbacks of gene editing with CRISPR-Cas systems include the occurrence of off-target mutations.

What is needed are stable and effective guide molecules for gene editing, as well as compositions and methods for use in treating disease.

There is an urgent need for new molecules for guiding gene editing with Cas9, and for allele selectivity and reduced off target activity.

BRIEF SUMMARY

This invention relates to the fields of biopharmaceuticals and therapeutics for editing genes, and regulating gene expression. More particularly, this invention relates to methods and compositions for editing or altering a polynucleotide, including genomic polynucleotides, and ultimately, for in vivo gene editing, and modulating, disrupting, activating or repressing gene expression.

This invention provides guide molecules that can be highly effective for CRISPR gene editing. The compositions and methods of this invention can be used for gene editing in vivo, ex vivo, and in vitro.

This invention further contemplates methods for gene editing with a Cas enzyme guided by novel allele-selective guide molecules. In some embodiments, guide molecules of this invention can used to perform gene editing with CRISPR-Cas systems with reduced occurrence of off-target mutations.

Guide molecules of this invention can provide efficient gene editing using Cas9. The Guide molecules of this invention can be active for gene editing to select between allelic variations based on one or more nucleotide polymorphisms. Further advantages of guide molecules of this disclosure include reduced off-target effects.

In some embodiments, the guide molecules of this invention can exhibit an extraordinary and surprising level of allele selectivity for targeting genomic DNA and generating double strand breaks through CRISPR/Cas gene editing. In certain embodiments, guide molecules of this invention can provide reduced off-target activity and greater efficiency of gene editing.

This invention also contemplates methods for gene editing with Cas guided by guide molecules, along with gene repair by any mechanism, including NHEJ and HDR repair mechanisms.

The guide molecules of this invention can advantageously increase the efficiency of gene engineering directed by Cas.

In some embodiments, the guide molecules of this invention can advantageously increase the efficiency of gene engineering directed by Cas9 and provide a high frequency of targeted mutagenesis via NHEJ.

In further embodiments, the guide molecules of this invention can advantageously increase the efficiency of gene engineering directed by Cas9 and provide exact DNA integration using HDR for any genomic target.

In some aspects, the guide molecules of this invention can enhance Cas9 binding and DNA cleavage in vivo.

This invention further provides novel molecules to be used as therapeutic agents for various diseases and conditions. The molecules of this invention can be used as active pharmaceutical ingredients in compositions for ameliorating, preventing or treating various diseases and conditions.

In some aspects, this invention provides guide molecules having structures that may include various combinations of linker groups, chain-forming monomers, non-natural nucleotides, modified nucleotides, or chemically-modified nucleotides, as well as certain natural nucleotides. These guide molecules can exhibit allele selectivity for targeting genomic DNA. This disclosure provides guide molecules that can used to perform CRISPR-Cas gene editing with reduced off-target mutations.

Embodiments of this invention include the following:

A guide compound targeted to a genomic DNA, comprising a target guide chain of 14-24 contiguous monomers attached to a crRNA, wherein the guide compound directs CRISPR gene editing of the genomic DNA.

The guide compound above, wherein the monomers comprise UNA monomers and nucleic acid monomers, and wherein the guide compound comprises a sequence of bases targeted to direct CRISPR gene editing of the genomic DNA.

The guide compound above, wherein the sequence of bases of the target guide chain has up to three mismatches from the genomic DNA.

The guide compound above, wherein the guide compound contains one to five UNA monomers.

The guide compound above, wherein the nucleic acid monomers are selected from natural nucleotides, non-natural nucleotides, modified nucleotides, chemically-modified nucleotides, and combinations thereof.

The guide compound above, wherein one or more of the nucleic acid monomers is a 2'-O-methyl ribonucleotide, a 2'-O-methyl purine nucleotide, a 2'-deoxy-2'-fluoro ribonucleotide, a 2'-deoxy-2'-fluoro pyrimidine nucleotide, a 2'-deoxy ribonucleotide, a 2'-deoxy purine nucleotide, a universal base nucleotide, a 5-C-methyl-nucleotide, an inverted deoxyabasic monomer residue, a 3'-end stabilized nucleotide, a 3'-glyceryl nucleotide, a 3'-inverted abasic nucleotide, a 3'-inverted thymidine, a locked nucleic acid nucleotide (LNA), a 2'-0,4'-C-methylene-(D-ribofuranosyl) nucleotide, a 2'-methoxyethoxy (MOE) nucleotide, a 2'-methyl-thio-ethyl, 2'-deoxy-2'-fluoro nucleotide, a 2'-O-methyl nucleotide, a 2',4'-Constrained 2'-O-Methoxyethyl (cMOE), a 2'-O-Ethyl (cEt), a 2'-amino nucleotide, a 2'-O-amino nucleotide, a 2'-C-allyl nucleotides, a 2'-O-allyl nucleotide, a $N^6$-methyladenosine nucleotide, a nucleotide with modified base 5-(3-amino)propyluridine, a nucleotide with modified base 5-(2-mercapto)ethyluridine, a nucleotide with modified base 5-bromouridine, a nucleotide with modified base 8-bromoguanosine, a nucleotide with modified base 7-deazaadenosine, a 2'-O-aminopropyl substituted nucleotide, or a nucleotide with a 2'-OH group replaced with a 2'-R, a 2'-OR, a 2'-halogen, a 2'-SR, or a 2'-amino, where R can be H, alkyl, alkenyl, or alkynyl.

The guide compound above, wherein one or more of the last three monomers at each end of the guide compound is connected by a phosphorothioate, a chiral phosphorothioate, or a phosphorodithioate linkage.

The guide compound above, wherein the guide compound directs double strand breaks in a gene selected from TTR, BIRC5, CDK16, STAT3, CFTR, F9, KRAS, and CAR.

The guide compound above, wherein the genomic DNA contains a target disease-related single nucleotide polymorphism.

The guide compound above, wherein the guide compound directs double strand breaks in a disease-related allele.

The guide compound above, wherein the guide compound directs double strand breaks in a disease-related allele selected from V30M TTR, G284R ColA1, L132P Keratin12, R135T Keratin12, G85R SOD1, G272V Tau, P301L Tau, V337M Tau, R406W Tau, Q39STOP beta-Globin, T8993G/C mtDNA, G719S EGFR, and G12C Kras.

The guide compound above, comprising 30-300 contiguous monomers.

The guide compound above, wherein the CRISPR gene editing uses Cas9.

The guide compound above, wherein the guide compound directs gene editing with reduced off target activity.

The guide compound above, wherein the guide compound directs more double strand breaks in a disease-related allele than in the same allele as a wild type.

A guide compound above annealed with a tracrRNA.

The guide compound above, wherein the tracrRNA is derived from S. pneumonia, S. pyogenes, N. menigiditis, or S. thermophiles.

A guide compound above annealed with a tracrRNA and complexed with a CRISPR-associated gene editing protein.

The guide compound above, wherein the CRISPR-associated gene editing protein is Cas9.

A guide compound targeted to a genomic DNA, wherein the guide compound is a chain of monomers and directs CRISPR gene editing of the genomic DNA, the guide compound comprising a target guide chain, a CRISPR crRNA, and a CRISPR tracrRNA as a single strand, wherein the target guide chain is 14-24 contiguous monomers in length, wherein the monomers comprise UNA monomers and nucleic acid monomers, and wherein the guide compound comprises a sequence of bases targeted to direct CRISPR gene editing of the genomic DNA.

The guide compound above, wherein the guide compound directs gene editing in a CRISPR/Cas9 complex.

A pharmaceutical composition comprising one or more guide compounds above and a pharmaceutically acceptable carrier. The pharmaceutically acceptable carrier may comprise a viral vector or a non-viral vector. The pharmaceutically acceptable carrier may comprise liposomes.

Embodiments of this invention include methods for editing a genomic DNA in a cell, wherein the cell comprises an inducible or constitutive CRISPR gene editing enzyme, the method comprising contacting the cell with a composition above.

The method above, wherein the editing is disrupting the DNA or repressing transcription of the DNA. The method above, wherein the editing is achieved with reduced off target activity. The method above, wherein the CRISPR gene editing enzyme is co-transfected with a composition above.

This invention includes methods for editing a genomic DNA in a subject in vivo, wherein the subject comprises an inducible or constitutive CRISPR gene editing enzyme, the method comprising administering to the subject a composition above. The editing can be disrupting the DNA or repressing transcription of the DNA. The editing can be achieved with reduced off target activity. The CRISPR gene editing enzyme may be co-transfected with a composition above.

This invention further contemplates methods for preventing, treating or ameliorating a disease associated with a target genomic DNA in a subject in need, wherein the subject comprises an inducible or constitutive CRISPR gene editing enzyme, the method comprising administering to the subject a composition above.

In some embodiments, this invention describes the use of a composition above for preventing, ameliorating or treating a disease or condition in a subject in need, the use in medical therapy, the use in the treatment of the human or animal body, or the use of a composition above for preparing or manufacturing a medicament for preventing, ameliorating or treating a disease or condition in a subject in need.

BRIEF DESCRIPTION OF THE DRAWINGS

FIG. 3 shows that U-Guide molecules UNA1 and UNA2 directed the cleavage of a 357-bp genomic TTR DNA at a predetermined position shown by the appearance of 275-bp and 82-bp products. As shown in FIG. 3, the U-Guide molecules of this invention exhibited surprisingly high allele selective gene editing of human V30M TTR over wild type TTR. This indicates the capability for reduced off target activity. Further, under the same conditions a CRISPR/Cas9 cr/tracr comparative guide (gRNA) having the same nucleobase sequence and structure as the U-Guide molecule, but lacking a UNA monomer, exhibited some selectivity for human V30M TTR over wild type TTR.

FIG. 10 shows that a U-Guide molecule UNA3 directed the cleavage of a 357-bp genomic TTR DNA at a predetermined position shown by the appearance of 271-bp and 86-bp products. As shown in FIG. 10, the U-Guide molecule of this invention exhibited allele selective gene editing of human V30M TTR over wild type TTR. This indicates the capability for reduced off target activity. Further, under the same conditions a CRISPR/Cas9 guide (gRNA) having the same nucleobase sequence and structure as the U-Guide molecule, but lacking any UNA monomer, exhibited some selectivity.

DETAILED DESCRIPTION OF THE INVENTION

Figure 1:
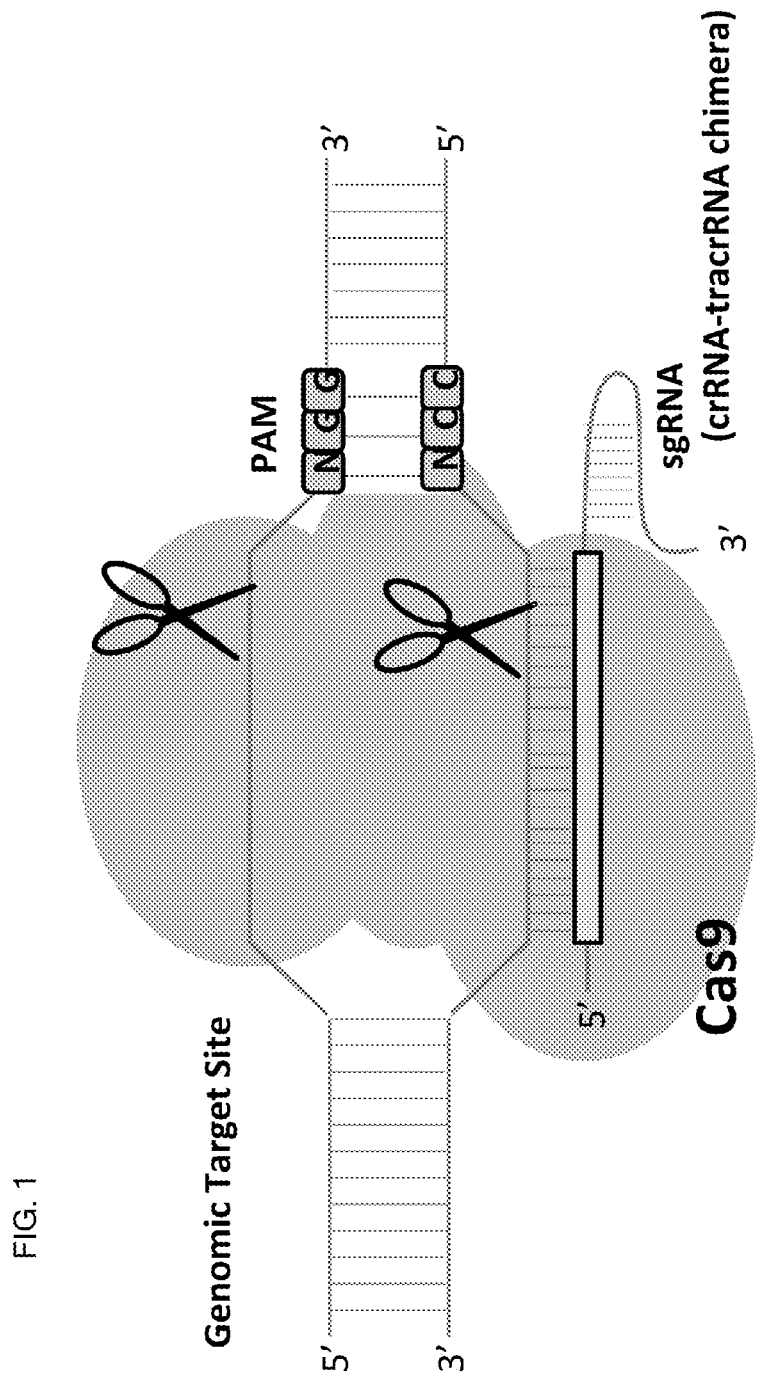
FIG. 1: illustrates a CRISPR-Cas gene editing complex with a "single guide" structure.

This invention provides a range of novel agents and compositions to be used for gene editing and therapeutic applications. Molecules of this invention can be used as guide components for compositions taking advantage of CRISPR gene editing modalities. The molecules and compositions of this invention can be used for ameliorating, preventing or treating various diseases associated with genes and their functionalities.

Guide molecules of this invention can provide efficient gene editing using Cas9, Cas9, and other gene editing enzymes.

The Guide molecules of this invention can be active for gene editing human genes. A Guide molecule can be attached to, or annealed with a tracrRNA to provide a Guide/tracr molecule for CRISPR/Cas gene editing.

The Guide/tracr molecules of this invention can be delivered and transfected into cells in vitro, in vivo, or ex vivo for editing a genomic DNA.

The Guide molecules of this invention can be surprisingly active for gene editing human genes with allele selective results.

In some embodiments, the Guide molecules of this invention exhibit an extraordinary and surprising level of allele selectivity for gene editing and generating double strand breaks in genomic DNA. This indicates the capability for advantageously reduced off target activity.

In some aspects, the ability to create double strand breaks in genomic DNA includes the ability to alter, modulate, or reduce the expression of the DNA in a cell.

A cell may be a eukaryotic cell, a mammalian cell, or a human cell.

The Guide molecules of this invention can be used for allele selective gene editing of human genomic DNA. This disclosure provides guide molecules that can used to perform CRISPR-Cas gene editing with reduced off-target mutations.

In certain embodiments, the Guide molecules of this invention can be used for allele selective gene editing of a human variant allele over a corresponding wild type allele with reduced off target effect.

In certain embodiments, the Guide molecules of this invention can be used for allele selective gene editing of a human gene variant allele over a corresponding wild type allele, with a selectivity of at least 30% as measured by editing efficiency.

In certain embodiments, the Guide molecules of this invention can be used for allele selective gene editing of a human gene variant allele over a corresponding wild type allele, with a selectivity of at least 40% as measured by editing efficiency.

In certain embodiments, the Guide molecules of this invention can be used for allele selective gene editing of a human gene variant allele over a corresponding wild type allele, with a selectivity ratio of at least 2 as measured by editing efficiency.

In certain embodiments, the Guide molecules of this invention can be used for allele selective gene editing of a human gene variant allele over a corresponding wild type allele, with a selectivity ratio of at least 3 as measured by editing efficiency.

In certain embodiments, the Guide molecules of this invention can be used for allele selective gene editing of a human gene variant allele over a corresponding wild type allele, with a selectivity ratio of at least 5 as measured by editing efficiency.

In certain embodiments, the Guide molecules of this invention can be used for allele selective gene editing of a human gene variant allele over a corresponding wild type allele, with a selectivity ratio of at least 8 as measured by editing efficiency.

By comparison, under the same conditions, a CRISPR/Cas9 guide having a selectivity ratio of 1 indicates lack of selectivity.

In certain embodiments, the Guide molecules of this invention can be used for allele selective gene editing of a human gene variant allele over a corresponding wild type allele, with essentially no off target activity toward the wild type allele.

In certain embodiments, the Guide molecules of this invention can be used for allele selective gene editing of a human gene variant allele over a corresponding wild type allele, with less than 1% off target activity toward the wild type allele.

In certain embodiments, the Guide molecules of this invention can be used for allele selective gene editing of a human gene variant allele over a corresponding wild type allele, with less than 3% off target activity toward the wild type allele.

The properties of the guide compounds of this invention arise according to their molecular structure, and the structure of the molecule in its entirety, as a whole, can provide significant benefits based on those properties. Embodiments of this invention can provide guide molecules having one or more properties that advantageously provide enhanced effectiveness in gene editing with Cas9, as well as compositions or formulations for therapeutic agents for various diseases and conditions, which can provide clinical agents.

A wide range of novel guide molecules are provided herein, each of which can incorporate specialized linker groups. The linker groups can be attached in a chain in the guide molecule. Each linker group can also be attached to a nucleobase.

In some aspects, a linker group can be a monomer. Monomers can be attached to form a chain molecule. In a chain molecule of this invention, a linker group monomer can be attached at any point in the chain.

In certain aspects, linker group monomers can be attached in a chain molecule of this invention so that the linker group monomers reside near the ends of the chain. The ends of the chain molecule can be formed by linker group monomers.

As used herein, a chain molecule can also be referred to as an oligomer.

In further aspects, the linker groups of a chain molecule can each be attached to a nucleobase. The presence of nucleobases in the chain molecule can provide a sequence of nucleobases.

In certain embodiments, this invention provides oligomer guide molecules having chain structures that incorporate novel combinations of the linker group monomers, along with certain natural nucleotides, or non-natural nucleotides, or modified nucleotides, or chemically-modified nucleotides.

The oligomer guide molecules of this invention can display a sequence of nucleobases that is targeted to at least a portion of a gene. In some embodiments, an oligomer can be targeted to at least a portion of a gene that is conserved, or highly conserved, among a number of variants.

In some aspects, this invention provides active oligomer guide molecules that correspond to, or are complementary to at least a fragment of a nucleic acid molecule, and that provide editing of at least such a fragment present in a cell.

In some embodiments, the cell can be a eukaryotic cell, a mammalian cell, or a human cell.

This invention provides structures, methods and compositions for oligomeric guide agents that incorporate the linker group monomers. The oligomeric guide molecules of this invention can be used as active agents in formulations for gene editing therapeutics.

This invention provides a range of guide molecules that are useful for providing therapeutic effects because of their activity in editing a gene. The guide molecules of this invention are structured to provide gene editing activity in vitro, ex vivo, and in vivo.

The guide molecules of this invention can be used in any CRISPR/Cas system.

In certain embodiments, an active guide molecule can be structured as an oligomer composed of monomers. The oligomeric structures of this invention may contain one or more linker group monomers, along with certain nucleotides.

In some aspects, this invention provides a CRISPR/Cas system having a Cas9 protein and one or more guide molecules that target a gene in a eukaryotic cell.

A guide molecule of this invention may have a guide sequence fused to a crispr-tracr sequence.

In further aspects, the CRISPR/Cas system may be used to cleave one or both strands of the DNA of the gene target.

The CRISPR gene editing enzyme, for example Cas9 protein, can be derived from *S. pneumonia*, *S. pyogenes* (for example, UniProtKB accession number Q99ZW2; CAS9_STRP1), *N. menigiditis*, and *S. thermophilus*, among other species.

The CRISPR gene editing enzyme may be derived from a genus including *Corynebacter, Sutterella, Legionella, Treponemna, Filifactor, Eubacterium, Streptococcus, Lactobacillus, Mycoplasma, Bacteroides, Flaviivola, Flavobacte-*

*rium, Sphaerochaeta, Azospirillumn, Gluconacetobacter, Neisseria, Roseburia, Parvibaculum, Staphylococcus, Nitratifractor, Mycoplasma,* and *Campylobacter.*

Embodiments of this invention can include methods for altering, modulating or reducing expression of a gene product. In some embodiments, a eukaryotic cell may contain and be expressing a DNA molecule having a target sequence, where the DNA encodes the gene product. The cell can be transfected with an engineered, non-naturally occurring CRISPR-associated (Cas) system, including an inducible or constitutive guide molecule of this invention that hybridizes with the target sequence. The CRISPR-associated (Cas) system may further include an inducible or constitutive Type-II Cas9 protein. The CRISPR-associated (Cas) system may further include one or more nuclear localization signals. The guide molecule can locate the target sequence and direct the Cas protein to cleave the DNA, and expression of a gene product can be altered. The Cas protein and the guide molecule do not naturally occur together.

Vectors for providing expression of one or more sequences in mammalian cells are known in the art.

Some examples of a Cas protein include Cas1, Cas2, Cas3, Cas4, Cas5, Cash, Cas7, Cas8, and Cas9.

A CRISPR-associated gene editing protein can include a Cas protein.

A CRISPR gene editing system can include polynucleotides, transcripts and moieties involved in the expression of, or directing the activity of genes encoding a CRISPR-associated (Cas) protein, a tracrRNA, and a guide chain. A CRISPR system can be derived from a particular organism having an endogenous CRISPR system, such as *Streptococcus pyogenes*. A CRISPR gene editing system can promote the formation of a CRISPR complex at the site of a target DNA sequence.

A Cas9 protein can be modified or mutated, or can be a homolog or ortholog for improved expression in a eukaryotic cell. A Cas9 protein can be human codon optimized. In some embodiments, paired guide molecules can be used to target different strands of a dsDNA with paired Cas9 nickases. Cleavage of both DNA strands by a pair of Cas9 nickases can be used to create a site-specific double strand break, which may decrease off-target effects without loss of efficiency of editing.

A guide molecule of this invention may contain a guide chain, which can also be referred to as a target guide chain. The guide chain can be composed of a chain of monomers, and each of the monomers can have an attached nucleobase. The guide chain can have a base sequence, which has sufficient complementarity with a target polynucleotide sequence to hybridize with the target sequence. The guide chain can direct sequence-specific binding of a CRISPR complex to the target sequence.

A guide molecule of this invention may contain a guide chain having a base sequence with sufficient complementarity to a target polynucleotide sequence to hybridize with the target sequence. The guide molecule may further contain a CRISPR portion or crRNA attached to the guide chain, where the crRNA can bind to a tracrRNA and direct sequence-specific binding of a CRISPR complex to the target sequence. Thus, the guide molecule can be a guide chain attached to a crRNA to form the guide molecule.

In some embodiments, this invention includes "single guide" embodiments in which a guide chain having sufficient complementarity with a target polynucleotide sequence to hybridize with the target sequence is attached to a crRNA sequence, which is further attached to a tracrRNA sequence, to form a "single guide molecule," where the single guide molecule can direct sequence-specific binding of a CRISPR complex to the target sequence. An example of a "single guide" embodiment is shown in FIG. 1.

A guide molecule of this invention, a crRNA, a guide chain, or a tracrRNA may contain one or more non-natural nucleotides, or modified nucleotides, or chemically-modified nucleotides.

In some embodiments, a guide molecule can be from 20 to 120 bases in length, or more. In certain embodiments, a guide molecule can be from 20 to 60 bases in length, or 20 to 50 bases, or 30 to 50 bases, or 39 to 46 bases.

In certain embodiments, a polynucleotide target sequence can be 5-100 bases in length, or 5-50 bases, or 5-30 bases, or 5-25 bases, or 5-24 bases, or 5-23 bases, or 5-22 bases, or 5-21 bases, or 5-20 bases, or 5-19 bases, or 5-18 bases.

In certain embodiments, a polynucleotide target sequence can be or 18-30 bases in length, or 18-24 bases, or 18-22 bases.

In additional embodiments, a polynucleotide target sequence can be 16 bases in length, or 17 bases, or 18 bases, or 19 bases, or 20 bases, or 21 bases, or 22 bases, or 23 bases, or 24 bases, or 25 bases, or 26 bases, or 27 bases, or 28 bases, or 29 bases, or 30 bases, or 31 bases, or 32 bases, or 33 bases, or 34 bases, or 35 bases.

In additional embodiments, a single guide molecule can be from 40 to 200 bases in length, or more.

The property of a guide sequence to direct sequence-specific binding of a CRISPR complex to a target sequence may be determined by any assay known in the art.

This invention further contemplates methods for delivering one or more vectors, or one or more transcripts thereof to a cell, as well as cells and organisms produced.

In some embodiments, the components of a CRISPR/Cas complex, including a guide molecule, can be delivered to a cell, in vitro, ex vivo, or in vivo. Viral and non-viral transfer methods as are known in the art can be used to introduce nucleic acids in mammalian cells. Nucleic acids can be delivered with a pharmaceutically acceptable vehicle, or for example, encapsulated in a liposome.

The target sequence can be any polynucleotide sequence, endogenous or exogenous to the eukaryotic cell. The target polynucleotide can be a coding or non-coding sequence. The target sequence can be associated with a PAM sequence, as are known in the art.

The target sequence can be any disease-associated polynucleotide or gene, as have been established in the art.

This invention further contemplates methods and compositions for repairing breaks in a polynucleotide or gene.

In some embodiments, a break in a polynucleotide or gene can be repaired by non-homologous end joining (NHEJ) to generate random insertions and deletions. The method may result in one or more changes in the structure of a protein expressed from a repaired target gene.

In further embodiments, a break in a polynucleotide or gene can be repaired by homology-directed repair (HDR) using an exogenous polynucleotide template to generate controlled insertions, deletions, and substitutions. The method may result in one or more changes in the structure of a protein expressed from a repaired target gene.

The repair of a break in a polynucleotide or gene can be done with a sense or antisense, single stranded oligonucleotide as a repair template, as is known in the art.

Allele Selective Embodiments and Reduced Off Target

This invention further contemplates Guide molecules that are allele selective for gene editing and generating double strand breaks in genomic DNA.

In some aspects, the Guide molecules of this invention can be used for gene editing with reduced off target activity.

In further aspects, the Guide molecules of this invention can be used for gene editing of a human gene variant allele over a corresponding wild type allele, with essentially no off target activity toward the wild type allele.

In certain embodiments, the Guide molecules of this invention can be used for allele selective gene editing of a human gene variant allele over a corresponding wild type allele, with less than 1% off target activity toward the wild type allele.

In certain embodiments, the Guide molecules of this invention can be used for allele selective gene editing of a human gene variant allele over a corresponding wild type allele, with less than 3% off target activity toward the wild type allele.

An allele selective guide molecule of this invention may contain a guide chain. The guide chain can be composed of a chain of monomers, and each of the monomers can have an attached nucleobase. The guide chain can have a base sequence, which has sufficient complementarity with a target polynucleotide sequence to hybridize with the target sequence. The guide chain can direct sequence-specific binding of a CRISPR complex to the target sequence.

A guide molecule of this invention having reduced off target effects may contain a guide chain. The guide chain can be composed of a chain of monomers, and each of the monomers can have an attached nucleobase. The guide chain can have a base sequence, which has sufficient complementarity with a target polynucleotide sequence to hybridize with the target sequence. The guide chain can direct sequence-specific binding of a CRISPR complex to the target sequence.

An allele selective guide molecule of this invention may contain a guide chain having a base sequence with sufficient complementarity to a target polynucleotide sequence to hybridize with the target sequence. The guide molecule may further contain a CRISPR portion or crRNA attached to the guide chain, where the crRNA can bind to a tracrRNA and direct sequence-specific binding of a CRISPR complex to the target sequence. Thus, the guide molecule can be a guide chain attached to a crRNA to form the guide molecule.

A guide molecule of this invention exhibiting reduced off target effects may contain a guide chain having a base sequence with sufficient complementarity to a target polynucleotide sequence to hybridize with the target sequence. The guide molecule may further contain a CRISPR portion or crRNA attached to the guide chain, where the crRNA can bind to a tracrRNA and direct sequence-specific binding of a CRISPR complex to the target sequence. Thus, the guide molecule can be a guide chain attached to a crRNA to form the guide molecule.

In some embodiments, this invention includes allele selective "single guide" embodiments in which a guide chain having sufficient complementarity with a target polynucleotide sequence to hybridize with the target sequence is attached to a crRNA sequence, which is further attached to a tracrRNA sequence, to form a "single guide molecule," where the single guide molecule can direct sequence-specific binding of a CRISPR complex to the target sequence.

Examples of target polynucleotide sequences for guide molecules of this invention are shown in Table 1. The target polynucleotide sequences in Table 1 reflect single nucleotide polymorphisms in certain human genes, which are disease-related.

TABLE 1

Guide target sequences for single nucleotide polymorphisms in human genes

| Gene | Mutation | Strand | 20-mer target (5'-3') | PAM | Cas9 |
| --- | --- | --- | --- | --- | --- |
| ColA1 | G284R | (+) | aagggagaagccagagatcc | NGG | S. pyr |
|  | G284R | (+) | gccagagatcctggaagacc | NGG | S. pyr |
|  | G284R | (+) | ccagagatcctggaagaccc | NGG | S. pyr |
|  | G284R | (+) | cagagatcctggaagacccg | NGG | S. pyr |
|  | G284R | (-) | ctggcttctcccttctctcc | NGG | S. pyr |
| Keratin 12 | L132P | (+) | aaactatgcaaaatcctaat | NNNNG ATT | N. menigiditis |
|  | R135T | (+) | tgatacattagcttcctacc | NGG | S. pyr |
| SOD1 | G85R | (+) | gcgcaatgtgactgctgacaaaga (24-mer) | NGG | S. pyr |
| Tau | G272V | (+) | gcaccagccgggagtcggga | NGG or NGGNG | S. thermophilus |
|  | G272V | (+) | tgaagcaccagccgggagtc | NGG | S. pyr |
|  | G272V | (+) | ctgaagcaccagccgggagt | NGG | S. pyr |
|  | G272V | (-) | cgactcccggctggtgcttc | NGG | S. pyr |
|  | G272V | (-) | gcaccttcccgactcccggc | NGG or NGGNG | S. pyr or S. thermophilus |
|  | G272V | (-) | atctgcaccttcccgactcc | NGG | S. pyr |
|  | P301L | (+) | gataatatcaaacacgtcct | NGG or NGGNG | S. pyr or S. thermophilus |
|  | P301L | (+) | aatatcaaacacgtcctggg | NGG | S. pyr |
|  | V337M | (-) | acttccatctggccacctcc | NGG | S. pyr |
|  | V337M | (-) | tctcagattttacttccatc | NGG | S. pyr |
|  | V337M | (-) | catctggccacctcctggtttatg (24-mer) | NNGRR (R = A/G) | SaCas |

TABLE 1-continued

Guide target sequences for single nucleotide polymorphisms in human genes

| Gene | Mutation | Strand | 20-mer target (5'-3') | PAM | Cas9 |
|---|---|---|---|---|---|
| | R406W | (-) | gagacattgctgagatgcca | NGG or NGGNG | S. pyror S. thermophilus |
| beta-Globin | Q39STOP | (+) | tggtctacccttggacctag | NGG | S. pyr |
| | Q39STOP | (+) | tcagaggttctttgagtcctt | NGG | S. pyr |
| | Q39STOP | (+) | cccttggacctagaggttct | NNGRR | SaCas |
| | Q39STOP | (-) | tcaaagaacctcttggtcca | NGG | S. pyr |
| | Q39STOP | (-) | caaagaacctcttggtccaa | NGG | S. pyr |
| | Q39STOP | (-) | ctcaaagaacctcttggtcc | NNGRR | SaCas |
| mtDNA | T8993G/C | (+) | agcggttaggcgtacggcc(c/g) | NGG | S. pyr |
| | T8993G/C | (+) | aggcgtacggcc(c/g)gggctat | NGG | S. pyr |
| | T8993G/C | (+) | cgtacggcc(c/g)gggctattgg | NNGRR | SaCas |
| | T8993G/C | (+) | cggcc(c/g)gggctattggttga | NNGRR | SaCas |
| EGFR | G719S | (+) | aagatcaaagtgctgagctc | NGG or NGGNG | S. pyror S. thermophilus |
| | G719S | (+) | gtgctgagctccggtgcgtt | NGG | S. pyr |
| | G719S | (+) | gagctccggtgcgttcggca | NGG or NGGNG | S. pyr or S. thermophilus |
| | G719S | (-) | agctcagcactttgatcttt | NNGRR | SaCas |
| Kras | G12C | | cttgtggtagttggagcttg | NGG | |

In Table 1, the position of the single nucleotide allelic mutation is underlined.

TABLE 2

Accession numbers for gene targets

| Disease | Gene | NCBI Acc # | Mutation |
|---|---|---|---|
| Ullrich Congenital Muscular Dystrophy (UCMD) | COL6A1 | NM_001848.2 | G284R (GGA to AGA) |
| Meesmann epithelial corneal dystrophy (MECD) | KRT12 | NM_000223.3 | L132P (CTT to CCT) and/or R135T (AGA to ACA) |
| Amyotrophic lateral sclerosis (ALS) | SOD1 | NM_000454.4 | G85R (GGC to CGC) |
| Frontotemporal dementia with parkinsonism linked to chromosom 17 (FTDP-17) | Tau | NM_001123066.3 | G272V (GGC to GTC), P301L (CCG to CTG), V337M (GTG to ATG), and/or R406W (CGG to TGG) |
| b-Thalassaemia | HBB | NM_000518.4 | Q39STOP (CAG to TAG) |
| Neurogenic weakness, ataxia and retinitis pigmentosa (NARP) | MT-ATP6 | NC_012920.1 | T8993G/C |
| Gefitinib-resistant cancer | EGFR | NM_005228.3 | G719S |

This invention contemplates Guide molecules that are allele selective for gene editing and generating double strand breaks in disease-related single nucleotide polymorphisms in human genes.

This invention further contemplates Guide molecules for gene editing and generating double strand breaks in disease-related single nucleotide polymorphisms in human genes with reduced off target activity.

An allele selective guide molecule of this invention may contain a guide chain. The guide chain can be composed of a chain of monomers, and each of the monomers can have an attached nucleobase. The guide chain can have a base sequence, which has sufficient complementarity with a target polynucleotide sequence containing a single nucleotide polymorphism to hybridize with the target sequence. The guide chain can direct sequence-specific binding of a CRISPR complex to the target sequence.

An allele selective guide molecule of this invention may contain a guide chain having a base sequence with sufficient complementarity to a target polynucleotide sequence containing a single nucleotide polymorphism to hybridize with the target sequence. The guide molecule may further contain a CRISPR portion or crRNA attached to the guide chain, where the crRNA can bind to a tracrRNA and direct sequence-specific binding of a CRISPR complex to the target sequence. Thus, the guide molecule can be a guide chain attached to a crRNA to form the guide molecule.

In some embodiments, this invention includes allele selective "single guide" embodiments in which a guide chain having sufficient complementarity with a target polynucleotide containing a single nucleotide polymorphism sequence to hybridize with the target sequence is attached to a crRNA sequence, which is further attached to a tracrRNA sequence, to form a "single guide molecule," where the single guide molecule can direct sequence-specific binding of a CRISPR complex to the target sequence.

TTR Embodiments

Amyloidosis related to transthyretin (ATTR) involves the depositing of amyloid fibril proteins in various organs and tissues, including the peripheral, autonomic, and central nervous systems. Transthyretin (TTR) is a secreted thyroid hormone-binding protein that binds and transports retinol binding protein, and serum thyroxine in plasma and cerebrospinal fluid.

The pathology of ATTR may include many TTR mutations. Symptoms of ATTR often include neuropathy and/or cardiomyopathy. Peripheral neuropathy can begin in the lower extremities, with sensory and motor neuropathy, and can progress to the upper extremities. Autonomic neuropathy can be manifest by gastrointestinal symptoms and orthostatic hypotension.

Patients with TTR gene Val-30-Met, the most common mutation, have normal echocardiograms. However, they may have conduction system irregularities and need a pacemaker. The ATTR V30M variant can cause lower extremity weakness, pain, and impaired sensation, as well as autonomic dysfunction. Vitreous and opaque amyloid deposits can be characteristic of ATTR.

The U-Guide molecules of this invention can be active for gene editing human TTR. A U-Guide molecule can be attached to, or annealed with a tracrRNA to provide a U-Guide/tracr molecule for CRISPR/Cas9 gene editing.

The U-Guide/tracr molecules of this invention can be delivered and transfected into cells in vitro, in vivo, or ex vivo for editing a genomic DNA.

The U-Guide molecules of this invention can be surprisingly active for gene editing human TTR with allele selective results.

In some embodiments, a U-Guide molecule of this invention can be active for gene editing human TTR with reduced off target activity.

In some embodiments, the U-Guide molecules of this invention exhibit an extraordinary and surprising level of allele selectivity for generating double strand breaks in V30M TTR over wild type TTR.

The U-Guide molecules of this invention can be used for allele selective gene editing of human TTR.

In further embodiments, the U-Guide molecules of this invention can be used for allele selective gene editing of human V30M TTR over wild type TTR with a selectivity ratio of at least 3.

In further embodiments, the U-Guide molecules of this invention can be used for allele selective gene editing of human V30M TTR over wild type TTR with a selectivity ratio of at least 5.

In additional embodiments, the U-Guide molecules of this invention can be used for allele selective gene editing of human V30M TTR over wild type TTR with a selectivity ratio of at least 8.

By direct comparison, under the same conditions, a CRISPR/Cas9 guide having the same nucleobase sequence and structure as the U-Guide molecule, but lacking any UNA monomer, may have a selectivity ratio of about 1, or less than 2.

In further aspects, the U-Guide molecules of this invention can be used for gene editing of human V30M TTR over wild type TTR, with essentially no off target activity toward the wild type allele.

In certain embodiments, the U-Guide molecules of this invention can be used for gene editing of human V30M TTR over wild type TTR, with less than 1% off target activity toward the wild type allele.

In certain embodiments, the U-Guide molecules of this invention can be used for gene editing of human V30M TTR over wild type TTR, with less than 3% off target activity toward the wild type allele.

U-guide Molecules

This invention further provides U-guide molecules that can be highly effective for gene editing with Cas9. The compositions and methods of this invention can be used for gene editing with Cas9 in vivo, ex vivo, and in vitro.

This invention contemplates methods for gene editing with Cas9 guided by novel U-guide molecules.

U-Guide molecules of this invention can provide efficient gene editing using Cas9.

The U-Guide molecules of this invention can be active for gene editing a TTR gene. The U-Guide molecules of this invention can be surprisingly active for gene editing human TTR with allele selective results, and can exhibit reduced off target effects.

In some embodiments, the U-Guide molecules of this invention exhibit an extraordinary and surprising level of allele selectivity for generating double strand breaks in V30M TTR over wild type TTR, indicating reduced off target effects.

This invention further contemplates methods for gene editing with Cas9 guided by novel U-guide molecules, along with gene repair by NHEJ and HDR repair mechanisms.

The U-guide molecules of this invention can advantageously increase the efficiency of gene engineering directed by Cas9.

In some embodiments, the U-guide molecules of this invention can advantageously increase the efficiency of gene engineering directed by Cas9 and provide a high frequency of targeted mutagenesis via NHEJ.

In further embodiments, the U-guide molecules of this invention can advantageously increase the efficiency of gene engineering directed by Cas9 and provide exact DNA integration using HDR for any genomic target.

In some aspects, the U-guide molecules of this invention can enhance Cas9 binding and DNA cleavage in vivo.

This invention provides novel molecules to be used as therapeutic agents for various diseases and conditions. The molecules of this invention can be used as active pharmaceutical ingredients in compositions for ameliorating, preventing or treating various diseases and conditions.

In some embodiments, molecules of this invention can be used for ameliorating and/or treating amyloidosis and related amyloid-related diseases, or Alzheimer's Disease.

Embodiments of this invention can provide guide molecules that advantageously provide effective gene editing with Cas9, as well as compositions or formulations for therapeutic agents, which can provide clinical agents.

The properties of the guide molecules of this invention arise according to their structure, and the molecular structure in its entirety, as a whole, can provide significant benefits and properties.

In some embodiments, a wide range of novel U-guide molecules are provided, which can incorporate one or more linker groups. The linker groups can be attached in a chain in the guide molecule. Each linker group can also be attached to a nucleobase.

In some aspects, a linker group can be a monomer. Monomers can be attached to form a chain molecule. In a chain molecule of this invention, a linker group monomer can be attached at any point in the chain.

In certain aspects, linker group monomers can be attached in a chain molecule of this invention so that the linker group monomers reside near the ends of the chain. The ends of the chain molecule can be formed by linker group monomers.

In further aspects, the linker groups of a chain molecule can each be attached to a nucleobase. The presence of nucleobases in the chain molecule can provide a sequence of nucleobases.

In certain embodiments, this invention provides oligomer molecules having chain structures that incorporate novel combinations of the linker group monomers, along with certain natural nucleotides, or non-natural nucleotides, or modified nucleotides, or chemically-modified nucleotides.

The oligomer molecules of this invention can display a sequence of nucleobases that is targeted to at least a portion of a polynucleotide or genome.

This invention provides structures, methods and compositions for oligomeric agents that incorporate the linker group monomers. The oligomeric molecules of this invention can be used as active agents in formulations for gene editing therapeutics.

Modalities of Action

Embodiments of this invention can provide an active guide molecule, which can be used for altering or editing a gene in a cell, thereby modulating gene functionality, gene expression or gene expression products.

This invention can provide robust and efficient methods for gene editing with a wide range of therapeutic applications.

In general, the CRISPR/Cas system can utilize a guide molecule to recognize a specific DNA target. The Cas enzyme may be recruited to a specific DNA target by the action of the guide molecule. The CRISPR/Cas system can be used for efficient and effective gene editing using guide molecules of this invention.

In some aspects, this invention provides methods for altering or modulating expression of one or more gene products.

Methods of this invention may utilize a vector for introducing into a eukaryotic cell the components of the Type II CRISPR/Cas9 Guided-Endonuclease gene editing system. The vector can have a regulatory sequence operably linked to a guide molecule that can hybridize with a target sequence in a gene, and an additional regulatory sequence operably linked to a Type II Cas9 endonuclease. The guide molecule can recruit the Cas9 protein to cleave the gene target. In certain embodiments, the vector can include a nuclear localization signal.

Some information concerning vectors is given in, for example, David V. Goeddel (Editor), Methods in Enzymology, Volume 185: Gene Expression Technology, Academic Press, 1990.

In some embodiments, a guide molecule may have a guide sequence attached to a crispr-tracr sequence. The guide sequence can be targeted to hybridize a gene target, and the crispr-tracr sequence can bind to Cas9.

Without wishing to be bound by any particular theory, a Type II prokaryotic CRISPR and CRISPR-associated protein (Cas) system can be used for gene editing. In the prokaryote, the system operates as an immune defense system. The CRISPR gene can consist of certain repeat sequences separated by spacer sequences that belong to targeted foreign genes. A primary transcript from CRISPR can be processed into CRISPR RNAs (crRNAs). The crRNA can consist of a conserved repeat sequence, and a variable spacer sequence or guide that is complementary to the target gene sequence. Trans activating crisper RNA (tracrRNA) can be a short RNA sequence that is complementary to the CRISPR repeat and serves to process crRNA. The complex formed by crRNA, tracrRNA and Cas9 binds to a target sequence by base pairing and causes sequence-specific, double strand DNA cleavage.

In further embodiments, a guide molecule of this invention can encompass structures that incorporate sequences related to crRNA and tracrRNA.

A CRISPR/Cas complex may include a guide sequence hybridized to a target sequence and complexed with a Cas protein. The CRISPR/Cas complex can provide cleavage of one or both strands of the target sequence, or within a few base pairs of the target sequence, or near the target sequence.

The components of the CRISPR/Cas complex including the Cas protein, the guide sequence, and the tracr sequence may each be operably linked to separate regulatory sequences on separate vectors.

The components of the CRISPR/Cas complex may be expressed from the same or different regulatory sequences, and may be combined in a single vector.

A vector may be used to provide one or more guide sequences.

As used herein, the term "Cas" refers to any Cas protein known in the art that is operable for gene editing using a guide molecule.

In some embodiments, one or more guide sequences can be used simultaneously for gene editing.

In some embodiments, this invention provides methods and compositions for knocking out genes, for amplifying genes, for repairing mutations associated with genomic instability, and for correcting known defects in a genome.

In some embodiments, the expression of one or more gene products of the target gene can be decreased.

In certain embodiments, the expression of one or more gene products of the target gene can be increased.

In some modalities, a CRISPR/Cas system can utilize a guide molecule of this invention for CRISPR genomic interference.

In certain aspects, a CRISPR/Cas system can utilize a guide molecule of this invention to repress gene expression. A catalytically inactive Cas9 can be used to suppress gene expression by interfering with transcription of the gene. A guide molecule of this invention can target the inactive Cas9 to a genomic sequence, acting as a repressor. The guide molecule may be co-expressed.

In certain embodiments, attachment of an effector domain having regulatory function to an inactive Cas9 can provide stable and efficient transcriptional repression. Attachment of a transcriptional repressor domain or regulatory domain having regulatory function to an inactive Cas9 can suppress expression of a targeted endogenous gene.

In some embodiments, a guide molecule of this invention can be relatively short, up to 14 or 16 nt in length, to allow an active Cas9 to bind specific target sequences without cleaving the DNA, therefore acting as a repressor.

In further aspects, a CRISPR/Cas system can utilize a guide molecule of this invention to activate gene expression. A transcriptional activator can be attached to an inactive Cas9. The transcriptional activator can increase gene expression, while the inactive Cas9 is targeted with a guide molecule of this invention.

UNA Monomers

In some embodiments, linker group monomers can be unlocked nucleomonomers (UNA monomers), which are small organic molecules based on a propane-1,2,3-tri-yl-trisoxy structure as shown below:

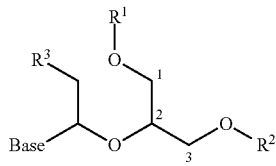

UNA Monomer where $R^1$ and $R^2$ are H, and $R^1$ and $R^2$ can be phosphodiester linkages, Base can be a nucleobase, and $R^3$ is a functional group described below.

In another view, the UNA monomer main atoms can be drawn in IUPAC notation as follows:

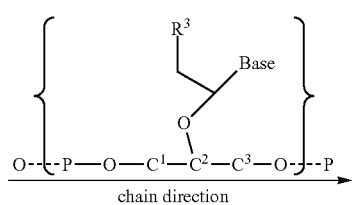

UNA monomer unit where the direction of progress of the oligomer chain is from the 1-end to the 3-end of the propane residue.

Examples of a nucleobase include uracil, thymine, cytosine, 5-methylcytosine, adenine, guanine, inosine, and natural and non-natural nucleobase analogues.

In general, because the UNA monomers are not nucleotides, they can exhibit at least four forms in an oligomer. First, a UNA monomer can be an internal monomer in an oligomer, where the UNA monomer is flanked by other monomers on both sides. In this form, the UNA monomer can participate in base pairing when the oligomer is a duplex, for example, and there are other monomers with nucleobases in the duplex.

Examples of UNA monomer as internal monomers flanked at both the propane-1-yl position and the propane-3-yl position, where $R^3$ is —OH, are shown below.

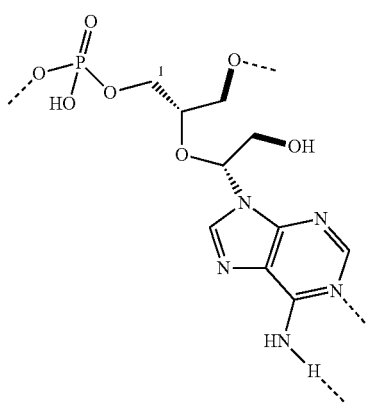

UNA-A

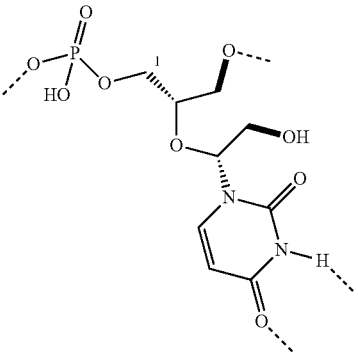

UNA-U

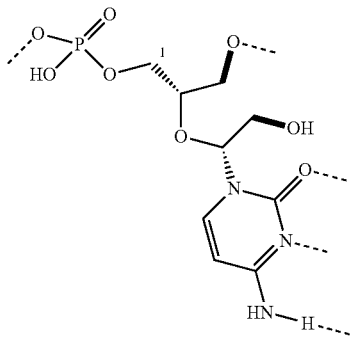

UNA-C

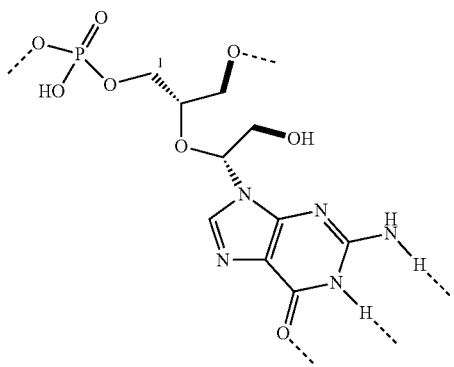

UNA-G

Second, a UNA monomer can be a monomer in an overhang of an oligomer duplex, where the UNA monomer is flanked by other monomers on both sides. In this form, the UNA monomer does not participate in base pairing. Because the UNA monomers are flexible organic structures, unlike nucleotides, the overhang containing a UNA monomer will be a flexible terminator for the oligomer.

A UNA monomer can be a terminal monomer in an overhang of an oligomer, where the UNA monomer is attached to only one monomer at either the propane-1-yl position or the propane-3-yl position. In this form, the UNA monomer does not participate in base pairing. Because the UNA monomers are flexible organic structures, unlike nucleotides, the overhang containing a UNA monomer can be a flexible terminator for the oligomer.

Examples of a UNA monomer as a terminal monomer attached at the propane-3-yl position are shown below.

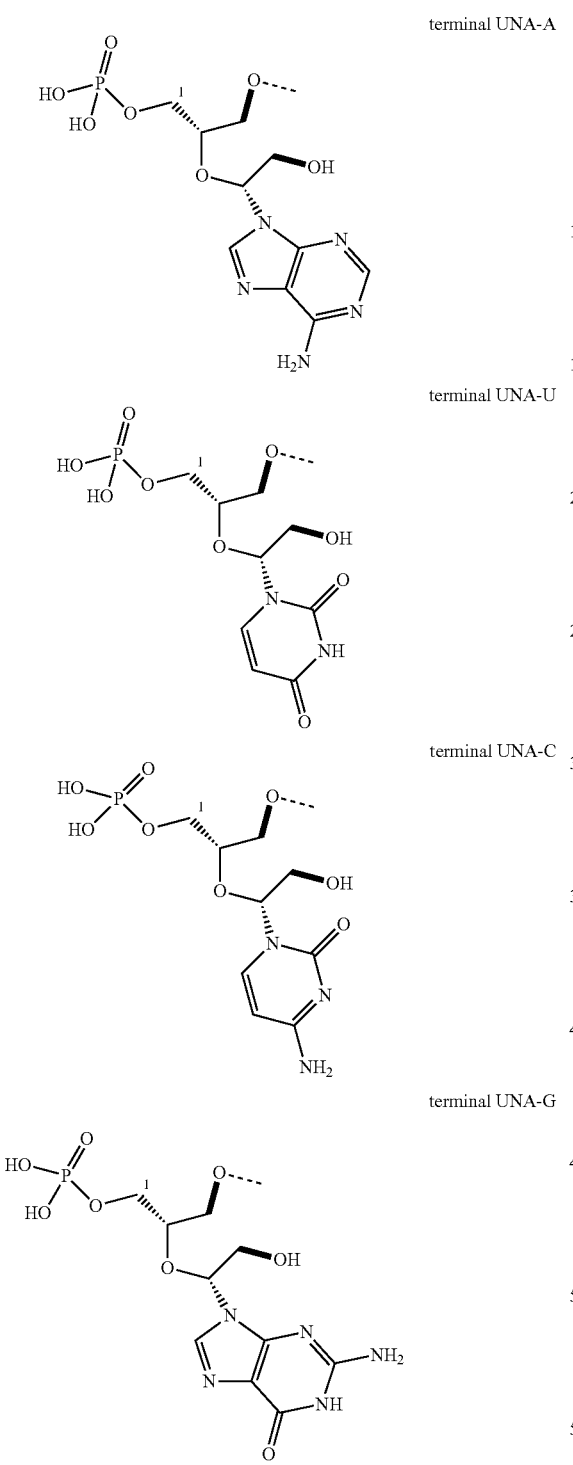

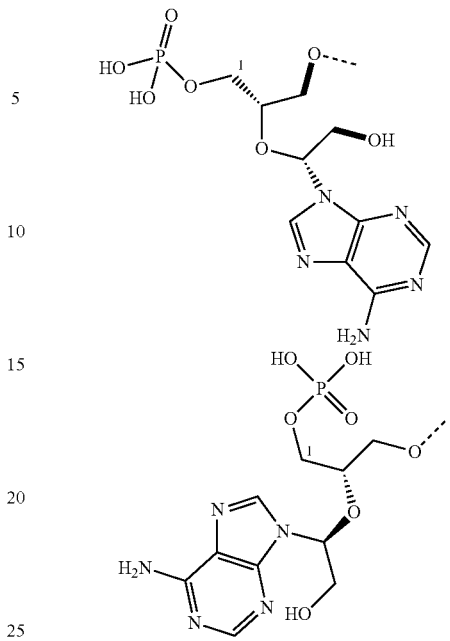

UNA-A terminal forms: the dashed bond shows the propane-3-yl attachment

Thus, UNA oligomers having a terminal UNA monomer are significantly different in structure from conventional nucleic acid agents. In contrast, the conformability of a terminal UNA monomer can provide UNA oligomers with different properties.

Among other things, the structure of the UNA monomer allows it to be attached to naturally-occurring nucleotides. A UNA oligomer can be a chain composed of UNA monomers, as well as various nucleotides that may be based on naturally-occurring nucleosides.

In some embodiments, the functional group $R^3$ of a UNA monomer can be —$OR^4$, —$SR^4$, —$NR^4{}_2$, —$NH(C=O)R^4$, morpholino, morpholin-1-yl, piperazin-1-yl, or 4-alkanoyl-piperazin-1-yl, where $R^4$ is the same or different for each occurrence, and can be H, alkyl, a cholesterol, a lipid molecule, a polyamine, an amino acid, or a polypeptide.

The UNA monomers are organic molecules. UNA monomers are not nucleic acid monomers or nucleotides, nor are they naturally-occurring nucleosides or modified naturally-occurring nucleosides.

A UNA oligomer of this invention is a synthetic chain molecule. A UNA oligomer of this invention is not a nucleic acid, nor an oligonucleotide.

In some embodiments, as shown above, a UNA monomer can be UNA-A (designated Ã), UNA-U (designated Ũ), UNA-C (designated Ĉ), and UNA-G (designated Ĝ).

Designations that may be used herein include mA, mG, mC, and mU, which refer to the 2'-O-Methyl modified ribonucleotides.

Designations that may be used herein include lower case c and u, which refer to the 2'-O-methyl modified ribonucleotides.

Designations that may be used herein include dT, which refers to a 2'-deoxy T nucleotide.

Because a UNA monomer can be a flexible molecule, a UNA monomer as a terminal monomer can assume widely differing conformations. An example of an energy minimized UNA monomer conformation as a terminal monomer attached at the propane-3-yl position is shown below.

Additional Monomers for Guide Compounds

As used herein, in the context of oligomer sequences, the symbol X represents a UNA monomer.

As used herein, in the context of oligomer sequences, the symbol N represents any natural nucleotide monomer, or a modified nucleotide monomer.

As used herein, in the context of oligomer sequences, the symbol Q represents a non-natural, modified, or chemically-modified nucleotide monomer.

When a Q monomer appears in one strand of a duplex, and is unpaired with the other strand, the monomer can have any base attached. When a Q monomer appears in one strand of a duplex, and is paired with a monomer in the other strand, the Q monomer can have any base attached that would be complementary to the monomer in the corresponding paired position in the other strand.

Examples of nucleic acid monomers include non-natural, modified, and chemically-modified nucleotides, including any such nucleotides known in the art.

Examples of non-natural, modified, and chemically-modified nucleotide monomers include any such nucleotides known in the art, for example, 2'-O-methyl ribonucleotides, 2'-O-methyl purine nucleotides, 2'-deoxy-2'-fluoro ribonucleotides, 2'-deoxy-2'-fluoro pyrimidine nucleotides, 2'-deoxy ribonucleotides, 2'-deoxy purine nucleotides, universal base nucleotides, 5-C-methyl-nucleotides, and inverted deoxyabasic monomer residues.

Examples of non-natural, modified, and chemically-modified nucleotide monomers include 3'-end stabilized nucleotides, 3'-glyceryl nucleotides, 3'-inverted abasic nucleotides, and 3'-inverted thymidine.

Examples of non-natural, modified, and chemically-modified nucleotide monomers include locked nucleic acid nucleotides (LNA), 2'-O,4'-C-methylene-(D-ribofuranosyl) nucleotides, 2'-methoxyethoxy (MOE) nucleotides, 2'-methyl-thio-ethyl, 2'-deoxy-2'-fluoro nucleotides, and 2'-O-methyl nucleotides.

Examples of non-natural, modified, and chemically-modified nucleotide monomers include 2',4'-Constrained 2'-O-Methoxyethyl (cMOE) and 2'-O-Ethyl (cEt) Modified DNAs.

Examples of non-natural, modified, and chemically-modified nucleotide monomers include 2'-amino nucleotides, 2'-O-amino nucleotides, 2'-C-allyl nucleotides, and 2'-O-allyl nucleotides.

Examples of non-natural, modified, and chemically-modified nucleotide monomers include $N^6$-methyladenosine nucleotides.

Examples of non-natural, modified, and chemically-modified nucleotide monomers include nucleotide monomers with modified bases 5-(3-amino)propyluridine, 5-(2-mercapto)ethyluridine, 5-bromouridine; 8-bromoguanosine, or 7-deazaadenosine.

Examples of non-natural, modified, and chemically-modified nucleotide monomers include 2'-O-aminopropyl substituted nucleotides.

Examples of non-natural, modified, and chemically-modified nucleotide monomers include replacing the 2'-OH group of a nucleotide with a 2'-R, a 2'-OR, a 2'-halogen, a 2'-SR, or a 2'-amino, where R can be H, alkyl, alkenyl, or alkynyl.

A guide molecule of this invention, a crRNA, a guide chain, or a tracrRNA may contain any one or more of the non-natural nucleotides, modified nucleotides, or chemically-modified nucleotides shown above.

In some aspects, a guide compound of this invention can be described by a sequence of attached bases, and being substituted or modified forms thereof. As used herein, substituted or modified forms include differently substituted UNA monomers, as well as differently substituted or modified nucleic acid monomers, as are further described herein.

Some examples of modified nucleotides are given in Saenger, Principles of Nucleic Acid Structure, Springer-Verlag, 1984.

U-Guide Compounds Composed of UNA Monomers

Aspects of this invention can provide structures and compositions for U-Guide molecules for gene editing that are UNA-monomer containing oligomeric compounds.

The oligomeric U-Guide agents may incorporate one or more UNA monomers. Oligomeric molecules of this invention can be used as active agents in formulations for gene editing therapeutics.

In some embodiments, this invention provides oligomeric U-Guide compounds having a structure that incorporates novel combinations of UNA monomers with certain natural nucleotides, non-natural nucleotides, modified nucleotides, or chemically-modified nucleotides.

In further aspects, the oligomeric U-Guide compounds of this invention can be pharmacologically active molecules. A U-Guide of this invention can be used as an active pharmaceutical ingredient for gene editing.

A U-Guide molecule of this invention can have the structure of Formula I

Formula I wherein $L^1$ is a linkage, n is from 39 to 46, and for each occurrence $L^2$ is a UNA linker group having the formula —$C^1$—$C^2$—$C^3$—, where R is attached to $C^2$ and has the formula —$OCH(CH_2R^3)R^5$, where $R^3$ is —$OR^4$, —$SR^4$, —$NR^4_2$, —$NH(C=O)R^4$, morpholino, morpholin-1-yl, piperazin-1-yl, or 4-alkanoyl-piperazin-1-yl, where $R^4$ is the same or different for each occurrence and is H, alkyl, a cholesterol, a lipid molecule, a polyamine, an amino acid, or a polypeptide, and where $R^5$ is a nucleobase, or $L^2(R)$ is a sugar such as a ribose and R is a nucleobase, or $L^2$ is a modified sugar such as a modified ribose and R is a nucleobase. In certain embodiments, alkyl is methyl, ethyl, propyl or isopropyl. In certain embodiments, a nucleobase can be a modified nucleobase. $L^1$ can be a phosphodiester linkage. In further embodiments, —$OCH(CH_2R^3)R^5$ may be —$SCH(CH_2R^3)R^5$, —$CH_2CH(CH_2R^3)R^5$, or —$(SO_2)CH(CH_2R^3)R^5$.

A U-Guide molecule of this invention can have a guide sequence that is complementary to a target sequence of a genome, where up to three mismatches can occur.

The target of a U-Guide molecule can be a target nucleic acid. In some embodiments, the target can be any genomic DNA of a subject. A U-Guide molecule can be active for gene editing with a CRISPR/Cas9 system.

In some aspects, a U-Guide molecule of this invention can have any number of phosphorothioate intermonomer linkages in any position in any strand.

In some embodiments, any one or more of the intermonomer linkages of a U-Guide molecule can be a phosphodiester, a phosphorothioate including dithioates, a chiral phosphorothioate, and other chemically modified forms.

For example, the symbol "N" can represent any nucleotide that is complementary to the monomer in the target.

The symbol "X" in a strand or oligomer represents a UNA monomer. When a UNA monomer appears in a strand of a U-Guide molecule, and is paired with a target, the UNA monomer can have any base attached that would be complementary to the monomer in the target strand.

When a U-Guide molecule terminates in a UNA monomer, the terminal position has a 1-end, or the terminal position has a 3-end, according to the positional numbering shown above. For example, the U-Guide molecule

SEQ ID NO: 1
1-ŨG̃CACGGCCACAUUGAUGGCGUUUUAGAGCUAUGCUGUCCŨŨ-3 has a UNA-U monomer 1-end on the left, and a UNA-U monomer 3-end on the right.

In some embodiments, a U-Guide molecule of this invention can have one or more UNA monomers at the 1-end of the strand, and one or more UNA monomers at the 3-end of the strand.

In certain embodiments, a U-Guide molecule of this invention may have a length of 39-46 monomers.

A U-Guide molecule of this invention for editing a gene can have a strand being 39-46 monomers in length, where the monomers can be UNA monomers and nucleic acid monomers.

A U-Guide molecule can be targeted to a target gene, and can exhibit reduced off-target effects as compared to conventional guide RNAs for CRISP/Cas9 gene editing.

Off target sites, based on sequence homology to the target, can be determined by constructing an episomally replicated reporter plasmid with either the target or off-target sequence. The reporter can be co-transfected with the U-Guide molecules into mammalian cells. The plasmids can be isolated to perform a T7 endonuclease I assay. Alternatively, sequencing of off-target can be done with PCR using a primer set flanking the potential off-target site.

A U-Guide molecule can be targeted to a target gene, and can exhibit increased efficiency of gene editing as compared to conventional guide RNAs for CRISP/Cas9 gene editing.

With a U-Guide molecule of this invention, the average rate of mutation of a genomic target can be at least 10%, or at least 15%, or at least 20%, or at least 25%, or at least 30%, or at least 40%, or at least 50%, or at least 60%, or at least 70%, or at least 80%, or at least 90%.

A U-Guide molecule of this disclosure may comprise naturally-occurring nucleic acid nucleotides, and modifications thereof that are compatible with gene editing activity.

As used herein, the term strand refers to a single, contiguous chain of monomers, the chain having any number of internal monomers and two end monomers, where each end monomer is attached to one internal monomer on one side, and is not attached to a monomer on the other side, so that it ends the chain.

The monomers of a U-Guide molecule may be attached via phosphodiester linkages, phosphorothioate linkages, gapped linkages, and other variations.

In some embodiments, a U-Guide molecule can include mismatches in complementarity between the guide sequence and the target sequence. In further embodiments, a U-Guide molecule may have 1, or 2, or 3 mismatches to the target.

The target of a U-Guide molecule can be a target nucleic acid of a target gene.

In certain embodiments, a U-Guide molecule can be a single strand that folds upon itself and hybridizes to itself to form a double stranded region having a connecting loop at one end.

In some embodiments, an U-Guide molecule of this invention may have a strand being 39-46 monomers in length, where any monomer that is not a UNA monomer can be a Q monomer.

In some embodiments, an U-Guide molecule of this invention may have a strand being 39-46 monomers in length, where any monomer that is not a UNA monomer can be a Q monomer, and where the number of Q monomers is less than twenty.

In some embodiments, an U-Guide molecule of this invention may have a strand being 39-46 monomers in length, where any monomer that is not a UNA monomer can be a Q monomer, and where the number of Q monomers is less than twelve.

In some embodiments, an U-Guide molecule of this invention may have a strand being 39-46 monomers in length, where any monomer that is not a UNA monomer can be a Q monomer, and where the number of Q monomers is less than ten.

In some embodiments, an U-Guide molecule of this invention may have a strand being 39-46 monomers in length, where any monomer that is not a UNA monomer can be a 2'-O-Methyl modified ribonucleotide.

Gene Editing

In some embodiments, the guide molecules of this invention can be used to edit any target portion of a TTR gene, when the target is flanked by a 3' protospacer-adjacent motif (PAM).

Examples of genes and/or polynucleotides that can be edited with the guide molecules of this invention include TTR, which may be related to amyloid neuropathy and amyloidosis.

In certain embodiments, this invention further contemplates methods for preventing, treating or ameliorating transthyretin-related hereditary amyloidosis.

Pharmaceutical Compositions

In some aspects, this invention provides pharmaceutical compositions containing an oligomeric compound and a pharmaceutically acceptable carrier.

A pharmaceutical composition can be capable of local or systemic administration. In some aspects, a pharmaceutical composition can be capable of any modality of administration. In certain aspects, the administration can be intravenous, subcutaneous, pulmonary, intramuscular, intraperitoneal, dermal, oral, or nasal administration.

Embodiments of this invention include pharmaceutical compositions containing an oligomeric compound in a lipid formulation.

In some embodiments, a pharmaceutical composition may comprise one or more lipids selected from cationic lipids, anionic lipids, sterols, pegylated lipids, and any combination of the foregoing.

In certain embodiments, a pharmaceutical composition can be substantially free of liposomes.

In further embodiments, a pharmaceutical composition can include liposomes or nanoparticles.

Some examples of lipids and lipid compositions for delivery of an active molecule of this invention are given in WO/2015/074085, which is hereby incorporated by reference in its entirety.

In additional embodiments, a pharmaceutical composition can contain an oligomeric compound within a viral or bacterial vector.

A pharmaceutical composition of this disclosure may include carriers, diluents or excipients as are known in the art. Examples of pharmaceutical compositions are described, for example, in *Remington's Pharmaceutical Sciences*, Mack Publishing Co. (A. R. Gennaro ed. 1985).

Examples of excipients for a pharmaceutical composition include antioxidants, suspending agents, dispersing agents, preservatives, buffering agents, tonicity agents, and surfactants.

An effective dose of an agent or pharmaceutical formulation of this invention can be an amount that is sufficient to cause gene editing in vivo.

An effective dose of an agent or pharmaceutical formulation of this invention can be an amount that is sufficient to cause an average rate of mutation of a genomic target in vivo of at least 10%, or at least 15%, or at least 20%, or at least 25%, or at least 30%, or at least 40%, or at least 50%, or at least 60%, or at least 70%, or at least 80%, or at least 90%.

A therapeutically effective dose can be an amount of an agent or formulation that is sufficient to cause a therapeutic effect. A therapeutically effective dose can be administered in one or more separate administrations, and by different routes.

A therapeutically effective dose, upon administration, can result in serum levels of an active agent of 1-1000 pg/ml, or 1-1000 ng/ml, or 1-1000 µg/ml, or more.

A therapeutically effective dose of an active agent in vivo can be a dose of 0.001-0.01 mg/kg body weight, or 0.01-0.1 mg/kg, or 0.1-1 mg/kg, or 1-10 mg/kg, or 10-100 mg/kg.

A therapeutically effective dose of an active agent in vivo can be a dose of 0.001 mg/kg body weight, or 0.01 mg/kg, or 0.1 mg/kg, or 1 mg/kg, or 2 mg/kg, or 3 mg/kg, or 4 mg/kg, or 5 mg/kg, or more.

Autosomal Dominant Diseases

Examples of diseases and/or conditions for which the guide molecules of this invention can be utilized include those in Table 3.

TABLE 3

Autosomal Dominant Diseases

| Autosomal Dominant Disease | Age/Notes | Related gene |
|---|---|---|
| Acropectoral syndrome | | |
| Acute intermittent porphyria | Adulthood. Attacks are treated with either glucose loading or hemin. These are specific treatments that lower the production of heme pathway intermediates by the liver. | HMBS gene |
| Adermatoglyphia | | |
| Albright's hereditary osteodystrophy | | |
| Arakawa's syndrome II | | |
| Aromatase excess syndrome | ~8-18 years old | Mutations in aromatase gene |
| Autosomal dominant cerebellar ataxia | | |
| Axenfeld syndrome | | |
| Bethlem myopathy | | |
| Birt-Hogg-Dube syndrome | Liver complications, progressive liver dysfunction, portal hypertension with varices, hypersplenism, and rarely overt liver failure with cirrhosis. Liver cancer. | Unknown, random |
| Boomerang dysplasia | | |
| Branchio-oto-renal syndrome | | |
| Buschke-Ollendorff syndrome | | |
| Camurati-Engelmann disease | Appears in childhood and is considered to be inherited. The disease is slowly progressive | Mutations in the TGFB1 gene |
| Central core disease | Reye's syndrome occurs almost exclusively in children. Acute liver failure/coma, death. | Unknown, possible damage to cellular mitochondria |
| Collagen disease | | |
| Collagenopathy, types II and XI | | |
| Congenital distal spinal muscular atrophy | | |
| Congenital stromal corneal dystrophy | | |
| Costello syndrome | | |
| Currarino syndrome | Birth to 64 years old | Mutation in the HLXB9 homeobox gene |
| Darier's disease | | |
| De Vivo disease | | |
| Dentatorubral-pallidoluysian atrophy | | |
| Dermatopathia pigmentosa reticularis | | |
| DiGeorge syndrome | | |
| Dysfibrinogenemia | Adulthood (20's) | Mutation controlling production of liver fibrinogen |

TABLE 3-continued

Autosomal Dominant Diseases

| Autosomal Dominant Disease | Age/Notes | Related gene |
|---|---|---|
| Familial atrial fibrillation | | |
| Familial hypercholesterolemia | Inherited condition that causes high levels of LDL cholesterol, beginning at birth, and heart attacks at an early age. | Mutations in APOB, LDLR, LDLRAP1, and PCSK9 |
| Familial male-limited precocious puberty | | |
| Feingold syndrome | | |
| Felty's syndrome | 50's, 60's | Unknown |
| Flynn-Aird syndrome | | |
| Gardner's syndrome | Birth to age 5 | Mutations in the APC gene |
| Gillespie syndrome | | |
| Gray platelet syndrome | | |
| Greig cephalopolysyndactyly syndrome | | |
| Hajdu-Cheney syndrome | | |
| Hawkinsinuria | | |
| Hay-Wells syndrome | | |
| Hereditary elliptocytosis | | |
| Hereditary hemorrhagic telangiectasia | Age-dependent, adolescence or later. Arteriovenous malformation (AVM) is one of the signs/symptoms, predominantly the lungs (50%), liver (30-70%), brain (10%). | Mutations in ACVRL1 gene |
| Hereditary mucoepithelial dysplasia | | |
| Hereditary spherocytosis | Acute cases can threaten to cause hypoxia through anemia and acute kernicterus through hyperbilirubinemia, particularly in newborns. | Mutations in the ANK1 gene. (also, SPTB, SPTA, SLC4A1, EPB42) |
| Holt-Oram syndrome | | |
| Hypertrophic cardiomyopathy | | |
| Hypoalphalipoproteinemia | | |
| Jackson-Weiss syndrome | | |
| Keratolytic winter erythema | | |
| Kniest dysplasia | | |
| Kostmann syndrome | | |
| Langer-Giedion syndrome | | |
| Larsen syndrome | | |
| Liddle's syndrome | | |
| Marfan syndrome | | |
| Marshall syndrome | | |
| Medullary cystic kidney disease | | |
| Metachondromatosis | | |
| Miller-Dieker syndrome | | |
| MOMO syndrome | | |
| Monilethrix | | |
| Multiple endocrine neoplasia | | |
| Multiple endocrine neoplasia type 1 | | |
| Multiple endocrine neoplasia type 2 | | |
| Multiple endocrine neoplasia type 2b | | |
| Myelokathexis | | |
| Myotonic dystrophy | | |
| Naegeli-Franceschetti-Jadassohn syndrome | | |
| Nail-patella syndrome | | |
| Noonan syndrome | | |
| Oculopharyngeal muscular dystrophy | | |
| Pachyonychia congenita | | |
| Pallister-Hall syndrome | | |
| PAPA syndrome | | |
| Papillorenal syndrome | | |
| Parastremmatic dwarfism | | |
| Pelger-Huet anomaly | | |
| Peutz-Jeghers syndrome | The average age of first diagnosis is 23, but the lesions can be identified at birth by an astute pediatrician | Mutations in the STK11 gene |
| Piebaldism | | |
| Platyspondylic lethal skeletal dysplasia, Torrance type | | |
| Popliteal pterygium syndrome | | |

TABLE 3-continued

Autosomal Dominant Diseases

| Autosomal Dominant Disease | Age/Notes | Related gene |
| --- | --- | --- |
| Porphyria cutanea tarda | Late adulthood between the ages of 30 to 40 years. | Inherited mutations in the UROD (20%). |
| RASopathy | | |
| Reis-Bucklers corneal dystrophy | | |
| Romano-Ward syndrome | | |
| Rosselli-Gulienetti syndrome | | |
| Roussy-Levy syndrome | | |
| Rubinstein-Taybi syndrome | | |
| Saethre-Chotzen syndrome | | |
| Schmitt Gillenwater Kelly syndrome | | |
| Short QT syndrome | | |
| Singleton Merten syndrome | | |
| Spinal muscular atrophy with lower extremity predominance | | |
| Spinocerebellar ataxia | | |
| Spinocerebellar ataxia type-6 | | |
| Spondyloepimetaphyseal dysplasia, Strudwick type | | |
| Spondyloepiphyseal dysplasia congenita | | |
| Spondyloperipheral dysplasia | | |
| Stickler syndrome | | |
| Tietz syndrome | | |
| Timothy syndrome | | |
| Treacher Collins syndrome | | |
| Tuberous sclerosis | Liver hamartomas. Essentially liver hamartoma embryonic dysplasia and tumor characteristics, from the surgical point of view will continue to hepatic disease classified as benign. | Tuberous Sclerosis, mutation of TSC1 or TSC2 |
| Upington disease | | |
| Variegate porphyria | Liver imaging beginning at age 50 years in those who have experienced persistent elevations in porphobilinogen or porphyrins may detect early hepatocellular carcinoma. | Mutations in the PPDX gene |
| Vitelliform macular dystrophy | | |
| Von Hippel-Lindau disease | | |
| Von Willebrand disease | Age 5-14 years, age 1-4 years and age 15-29 years. Age 75+ years and age <1 years rare. | Mutations in the VWF gene |
| Wallis-Zieff-Goldblatt syndrome | | |
| WHIM syndrome | | |
| White sponge nevus | | |
| Worth syndrome | | |
| Zaspopathy | | |
| Zimmermann-Laband syndrome | | |
| Zori-Stalker-Williams syndrome | | |

Protocol for Assessment of mTTR Gene Editing by T7 Assay

Hepa 1-6 cells expressing WT mouse TTR were transfected by LIPOFECTAMINE MESSENGERMAX reagent with Cas9 mRNA 4 hours prior to transfection with the UNA-Guide or comparative guide, each of which was a pre-annealed crRNA:tracrRNA unit targeting exon 2 of mTTR. 48 h following transfection, genomic DNA was isolated and a 459 by fragment of mTTR was amplified using primers

```
                                           SEQ ID NO: 2
5' CTGGTGCACAGCAGTGCATCT3'
and
                                           SEQ ID NO: 3
5' CCTCTCTCTGAGCCCTCTAGCTGGTA3'.
```

The PCR product was then heated at 98° C. for 5 minutes, and then slowly allowed to cool to room temperature for heteroduplex formation. The T7 endonuclease assay was then performed to assess gene editing. Image J analysis software was used to determine the percentage of Indels generated using the formula % Indel=100×(1-(1-Cleaved DNA fragment Area/Total Area)$^{1/2}$).

ELISA Assessment of Secreted mTTR Protein Knockdown by CRISPR/Cas9 Gene Editing

Hepa 1-6 cells expressing WT mouse TTR were transfected by LIPOFECTAMINE MESSENGERMAX reagent with Cas9 mRNA 4 hours prior to transfection with the UNA-Guide or comparative guide, each of which was a pre-annealed crRNA:tracrRNA targeting exon 2 of mTTR. 48 h following transfection, the supernatant was collected and an enzyme-linked immunosorbent assay (ELISA) (mouse prealbumin ELISA kit, Genway) performed to quantify the amount of secreted mouse TTR protein.

In Vivo Assessment of Gene Editing by T7 Assay

Cas9 mRNA and the UNA-Guide or comparative guide, each of which was a pre-annealed crRNA:tracrRNA targeting exon 2 of mTTR, were encapsulated by lipid nanoparticles separately and then mixed together for single administration by tail vein injection at 10 mg/kg total RNA. Six days post-dosing, the female 6-8 week old Balb/c mice were sacrificed and the genomic DNA was isolated and a 459 by fragment of mTTR amplified using primers SEQ ID NO: 4
5' CTGGTGCACAGCAGTGCATCT3'
and

SEQ ID NO: 5
5' CCTCTCTCTGAGCCCTCTAGCTGGTA3'.

The PCR product was then heated at 98° C. for 5 minutes and then slowly allowed to cool to room temperature for heteroduplex formation. The T7 endonuclease assay was then performed to assess gene editing. Image J analysis software was used to determine the percentage of Indels generated using the formula % Indel=100×(1−(1−Cleaved DNA fragment Area/Total Area)$^{1/2}$).

In Vivo ELISA Assessment of Secreted mTTR Protein Knockdown by CRISPR/Cas9 Gene Editing Cas9 mRNA and the UNA-Guide or comparative guide, each of which was a pre-annealed crRNA:tracrRNA targeting exon 2 of mTTR, were encapsulated by lipid nanoparticles separately and then mixed together for single administration by tail vien injection at 10 mg/kg total RNA. 2, 4 and 6 days post-dosing, serum was collected from the female 6-8 week old Balb/c mice and the amount of secreted mouse TTR protein determined by an enzyme-linked immunosorbent assay (ELISA) (mouse prealbumin ELISA kit, Genway).

CRISPR/Cas9 Gene Editing Targeting Mouse TTR

A 20-mer guide sequence for V30M mTTR is shown in Table 4.

TABLE 4

20-mer guide sequence for V30M mTTR

| SEQ ID NO. | SEQUENCE |
|---|---|
| 6 | 3'-GGA-CGA<u>CAT</u>CTGCACCGACATTT-5' (V30M mTTR GENE) |

The underlined CAT in Table 4 shows the V30M mutation.

A U-Guide molecule was synthesized, wherein the molecule contained the 20-mer guide sequence for V30M and a CRISPR sequence of *S. pyogenes*.

Figure 2:
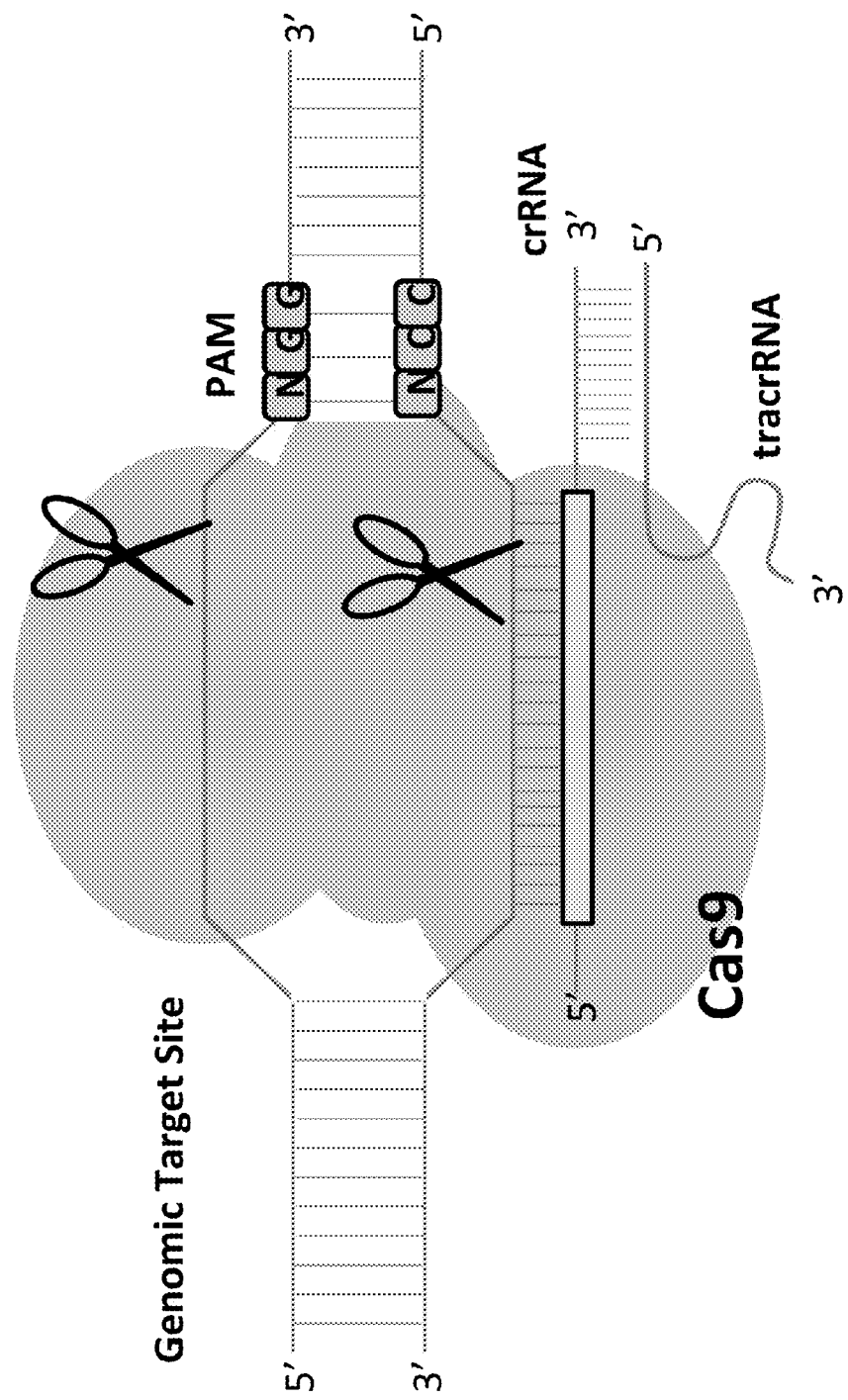
FIG. 2: illustrates a CRISPR-Cas gene editing complex.

Examples of a 20-mer target length U-Guide molecule for the V30M region of mTTR are shown in Table 5. The molecules in Table 5 contain the target U-Guide attached to a crRNA, as shown in FIG. 2.

TABLE 5

20-mer target length U-Guide molecules for editing the V30M region of mTTR

| SEQ ID NO. | U-GUIDE STRUCTURE (1 or 5' to 3') |
|---|---|
| 7 | Ũ*mU*mU*ACAGCCACGUCUACAGCGUUUUAGAGCUAU*mG*mC*mU |
| 8 | mU*Ũ*mU*ACAGCCACGUCUACAGCGUUUUAGAGCUAU*mG*mC*mU |
| 9 | mU*mU*Ũ*ACAGCCACGUCUACAGCGUUUUAGAGCUAU*mG*mC*mU |

TABLE 5-continued 20-mer target length U-Guide molecules for editing the V30M region of mTTR

| SEQ ID NO. | U-GUIDE STRUCTURE (1 or 5' to 3') |
|---|---|
| 10 | mU*mU*mU*ACAGCCACGUCUACAGCGUUUUAGAGCUAU*mG*mC*Ũ |

In Table 5, N (=A, U, C, G) designates an RNA monomer, mN designates a 2'-O-methyl-RNA monomer, * designates a 3'-phosphorothioate linkage, and Ã, Ũ, Č, Ĝ designate UNA monomers.

EXAMPLES

Example 1

Allele Selective Editing of a TTR Genomic Site with a U-Guide Molecule for CRISPR/Cas9

For this experiment, a 357-bp PCR product was generated from human TTR genomic DNA, accession number NC_000018.10, using the primers:

SEQ ID NO. 11

Forward (intron 1): 5'-tgtcttctctacacccagggcac-3'

SEQ ID NO. 12

Reverse (exon 2): 5'-gcaaaccacagctagaggagagga-3'.

Guide sequences of 20-mer length were identified that targeted regions 269-288 and 269-286, respectively, of the human TTR coding region.

A 20-mer guide sequence for V30M hTTR is shown in Table 6.

TABLE 6

20-mer guide sequence for V30M hTTR

| SEQ ID NO. | SEQUENCE |
|---|---|
| 13 | 3'-CGGUAGUUACACCGGUACGU-5' (TARGET GUIDE) |
| 14 | 5'-CCT-GCCATCAATGTGGCC<u>A</u>TGCA-3' (V30M TTR GENE) |
| 15 | 3'-GGA-CGGTAGTTACACCGG<u>T</u>ACGT-5' (V30M TTR GENE) |

In Table 6, the underlined positions show the V30M mutation. In Table 6, SEQ ID NO:13 can also be written in the 5' to 3' direction, and appears in the U-Guide molecules of Table 7 written in the 5' to 3' direction.

A U-Guide molecule was synthesized, wherein the molecule contained the 20-mer guide sequence for V30M and a CRISPR sequence of *S. pyogenes*.

Examples of 20-mer target length U-Guide molecules for the V30M region of hTTR are shown in Table 7. The molecules in Table 7 contain the target U-Guide attached to a crRNA, as shown in FIG. 2.

TABLE 7

20-mer target length U-Guide molecules for editing the V30M region of hTTR

| SEQ ID NO. | U-GUIDE STRUCTURE (1 or 5' to 3') |
|---|---|
| 16 | ŨGCAUGGCCACAUUGAUGGCGUUUUAGAGCUAUGCU |
| 17 | UĜCAUGGCCACAUUGAUGGCGUUUUAGAGCUAUGCU |
| 18 | UGČAUGGCCACAUUGAUGGCGUUUUAGAGCUAUGCU |
| 19 | UGCÃUGGCCACAUUGAUGGCGUUUUAGAGCUAUGCU |
| 20 | UGCAUGGCCACAUUGAUGGCGUUUUAGAGCUAUGCŨ |
| 21 | UGCAUGGCCACAUUGAUGGCGUUUUAGAGCUAUGČU |
| 22 | UGCAUGGCCACAUUGAUGGCGUUUUAGAGCUAUĜCU |
| 23 | UGCAUGGCCACAUUGAUGGCGUUUUAGAGCUAŨGCU |
| 24 | ŨmGmCAUGGCCACAUUGAUGGCGUUUUAGAGCUAUmGmCmU |
| 25 | mUĜmCAUGGCCACAUUGAUGGCGUUUUAGAGCUAUmGmCmU |
| 26 | mUmGČAUGGCCACAUUGAUGGCGUUUUAGAGCUAUmGmCmU |
| 27 | mUmGmCÃUGGCCACAUUGAUGGCGUUUUAGAGCUAUmGmCmU |
| 28 | mUmGmCAUGGCCACAUUGAUGGCGUUUUAGAGCUAUmGmCŨ |
| 29 | mUmGmCAUGGCCACAUUGAUGGCGUUUUAGAGCUAUmGČmU |
| 30 | mUmGmCAUGGCCACAUUGAUGGCGUUUUAGAGCUAUĜmCmU |
| 31 | mUmGmCAUGGCCACAUUGAUGGCGUUUUAGAGCUAŨmGmCmU |
| 32 | Ũ*mG*mC*AUGGCCACAUUGAUGGCGUUUUAGAGCUAU*mG*mC*mU |
| 33 | mU*Ĝ*mC*AUGGCCACAUUGAUGGCGUUUUAGAGCUAU*mG*mC*mU |
| 34 | mU*mG*Č*AUGGCCACAUUGAUGGCGUUUUAGAGCUAU*mG*mC*mU |
| 35 | mU*mG*mC*ÃUGGCCACAUUGAUGGCGUUUUAGAGCUAU*mG*mC*mU |
| 36 | mU*mG*mC*AUGGCCACAUUGAUGGCGUUUUAGAGCUAU*mG*mC*Ũ |
| 37 | mU*mG*mC*AUGGCCACAUUGAUGGCGUUUUAGAGCUAU*mG*Č*mU |
| 38 | mU*mG*mC*AUGGCCACAUUGAUGGCGUUUUAGAGCUAU*Ĝ*mC*mU |
| 39 | mU*mG*mC*AUGGCCACAUUGAUGGCGUUUUAGAGCUAŨ*mG*mC*mU |

In Table 7, N (=A, U, C, G) designates an RNA monomer, mN designates a 2'-O-methyl-RNA monomer, * designates a 3'-phosphorothioate linkage, and Ã, Ũ, Č, Ĝ designate UNA monomers.

A U-Guide molecule in Table 7 was active for gene editing human TTR. An assay for gene editing human TTR was performed with the 357 by PCR product. In this assay, the U-Guide molecule is pre-annealed with a tracrRNA to provide the U-Guide/tracr for CRISPR/Cas9 gene editing.

In the assay, 293 cells expressing V30M human TTR and 293 cells expressing WT human TTR were each transfected using LIPOFECTAMINE MESSENGER MAX reagent with Cas9 mRNA 4 hours prior to transfection with the U-Guide/tracr. 48 h following transfection, genomic DNA was isolated, and the T7 endonuclease assay performed.

Figure 3:
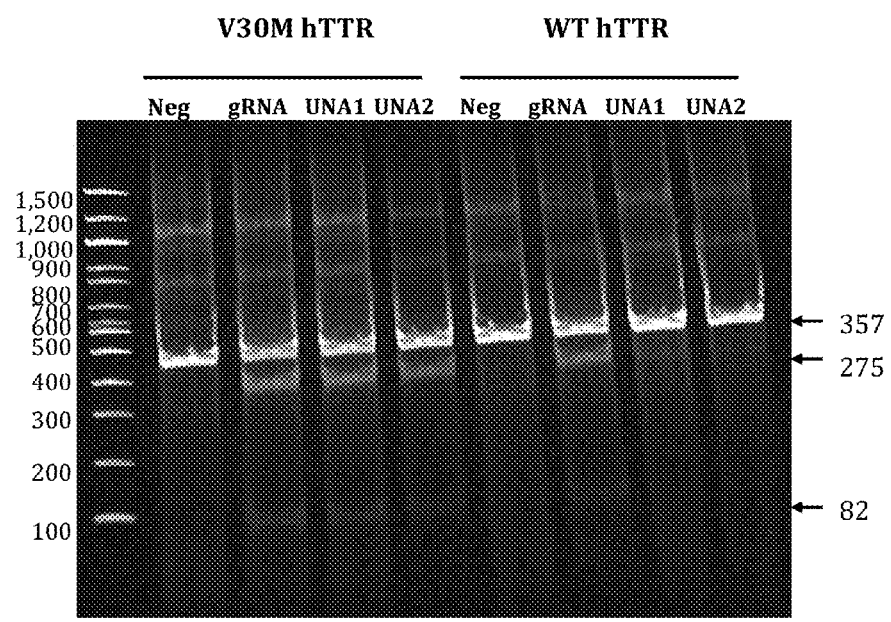
FIG. 3: Allele selective gene editing of a transthyretin (TTR) genomic site with a U-Guide molecule for CRISPR/Cas9.

FIG. 3 shows that using U-Guide molecules UNA1 (SEQ ID NO:32) and UNA2 (SEQ ID NO:35), double strand breaks were made in the 357 by PCR product to give 275 by and 82 by cleavage products.

The U-Guide molecule SEQ ID NO:32 was surprisingly active for gene editing human TTR with allele selective results. The U-Guide molecule SEQ ID NO:32 showed an extraordinary level of allele selectivity for generating double strand breaks in V30M TTR over wild type TTR.

Figure 4:
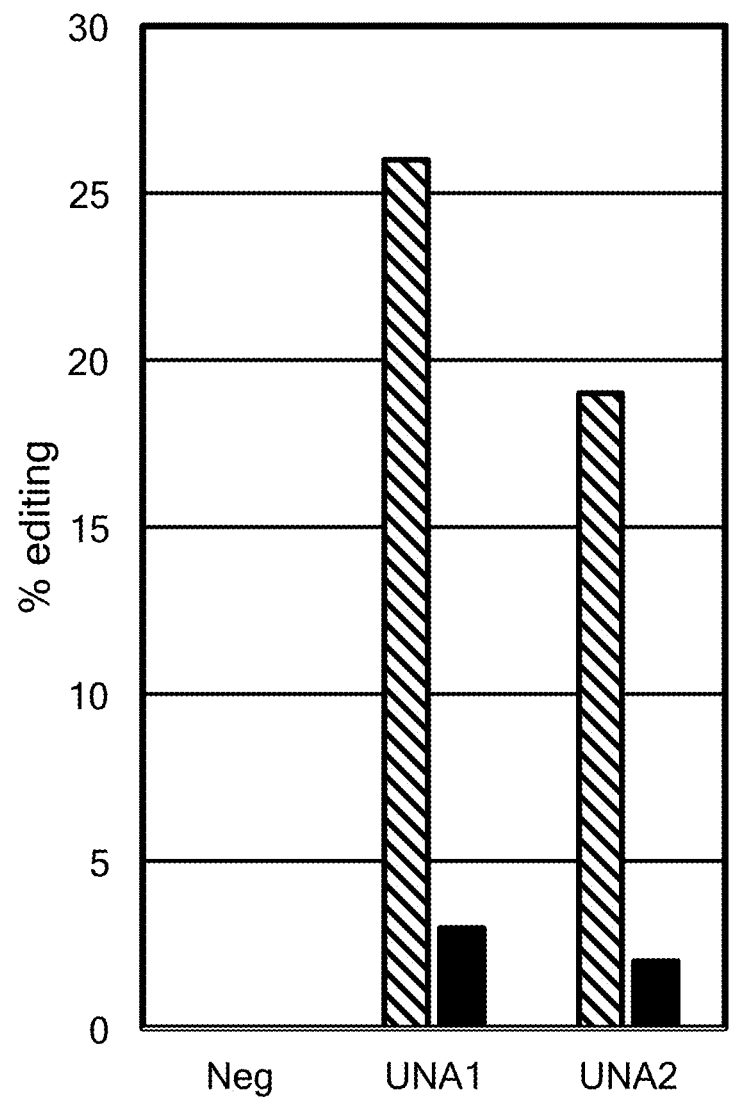
FIG. 4 shows that the U-Guide molecules UNA1 and UNA2 of this invention provided selective editing of V30M TTR over wild type TTR in a CRISPR/Cas9 system. The U-Guide molecules UNA1 and UNA2 produced high levels of double strand breaks in V30M TTR (patterned bar), but surprisingly few double strand breaks in wild type TTR (black bar). Thus, the U-Guide molecules UNA1 and UNA2 of this invention were extraordinarily active for allele selective gene editing of human TTR. This indicates the capability for reduced off target activity. The Neg control contained no CRISPR/tracr guide.

As shown in FIG. 4, the U-Guide molecule SEQ ID NO:32 provided 26% editing of V30M TTR, but only about 3% editing of wild type TTR, where the editing represents the degree of double strand breaks. Thus, the U-Guide molecule SEQ ID NO:32 was surprisingly and extraordinarily active for gene editing human TTR with allele selective results. This example indicates the capability for reduced off target activity.

The U-Guide molecule SEQ ID NO:35 was surprisingly active for gene editing human TTR with allele selective results. The U-Guide molecule SEQ ID NO:35 showed an extraordinary level of allele selectivity for generating double strand breaks in V30M TTR over wild type TTR.

As shown in FIG. 4, the U-Guide molecule SEQ ID NO:35 provided 19% editing of V30M TTR, but only about 2% editing of wild type TTR, where the editing represents the degree of double strand breaks. Thus, the U-Guide molecule SEQ ID NO:35 was surprisingly and extraordinarily active for gene editing human TTR with allele selective results. This example indicates the capability for reduced off target activity.

Figure 5:
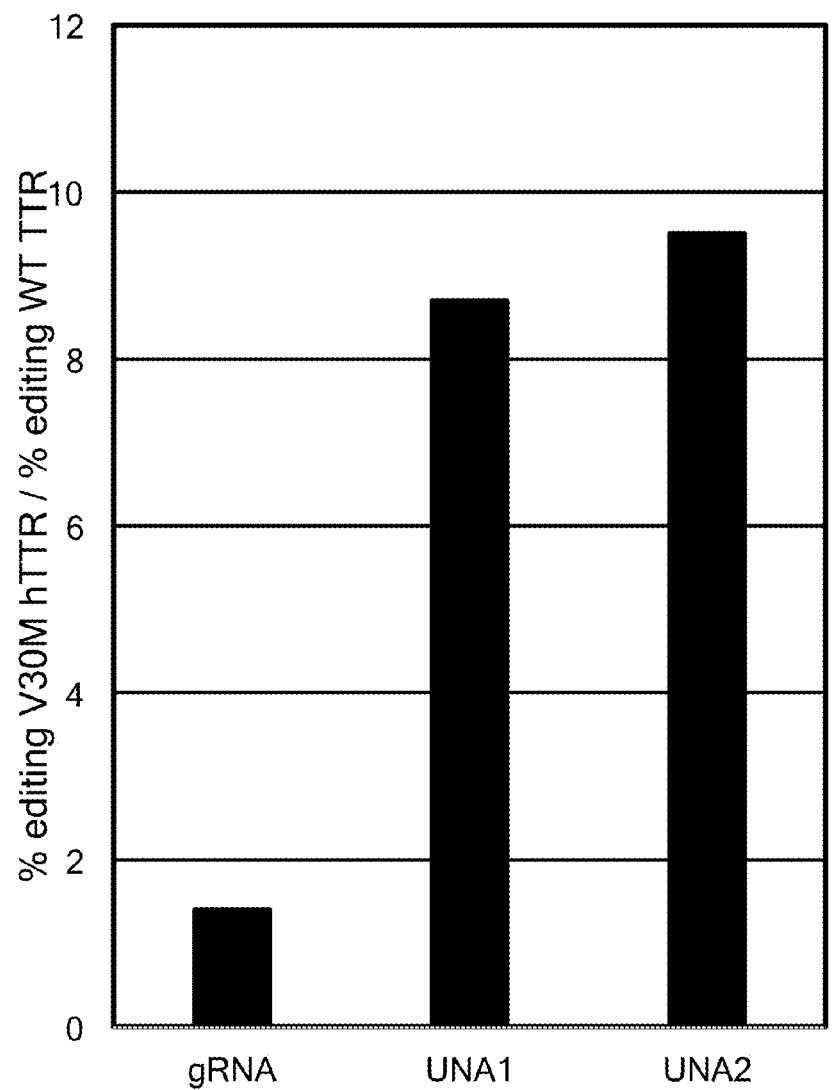
FIG. 5: The U-Guide molecules of this invention can be used for allele selective gene editing of human TTR. The surprising level of allele selectivity for gene editing of human TTR is shown in FIG. 5. The U-Guide molecules UNA1 and UNA2 provided high selectivity ratios of 8.7 and 9.5, respectively. This indicates the capability for reduced off target activity. Further, under the same conditions, a CRISPR/Cas9 cr/tracr guide (gRNA) having the same nucleobase sequence and structure as the U-Guide molecules, but lacking any UNA monomer, exhibited selectivity ratio of 1.4. Thus, the U-Guide molecules UNA1 and UNA2 were extraordinarily active for gene editing human TTR with allele selectivity of V30M TTR over wild type TTR.

These results show that the U-Guide molecules of this invention can be used for allele selective gene editing of human TTR. The surprising level of allele selectivity for gene editing of human TTR is shown in FIG. 5. The U-Guide molecule SEQ ID NO:32 provided a high selectivity ratio of 8.7. Further, the U-Guide molecule SEQ ID NO:35 provided a high selectivity ratio of 9.5.

Further, under the same conditions, a CRISPR/Cas9 guide having the same nucleobase sequence and structure as the U-Guide molecule SEQ ID NOs:32 and 35, but lacking any UNA monomer, had a selectivity ratio of 1.43.

Assessment of genome editing by sequence trace decomposition was also performed. 293 cells expressing either V30M or WT human TTR were transfected by LIPOFECTAMINE MESSENGERMAX reagent with Cas9 mRNA 4 hours prior to transfection with the comparative guide or UNA-Guide (UNA1), each of which were pre-annealed with tracrRNA, and targeting the V30M mutation of hTTR. 48 h following transfection, genomic DNA was isolated and a 1048 by fragment of hTTR was amplified. The PCR product was purified and then sanger sequenced.

The sequencing data files were imported into TIDE (Tracking of Indels by Decomposition) (See, e.g., Brinkman, 2014, Nucl. Acids Res., Vol. 42, No. 22, pp. 1-8) and aligned to the control sequence to determine the relative abundance of aberrant nucleotides following the expected break site to generate the spectrum of insertions and deletions (indels) and their frequencies.

Figure 6:
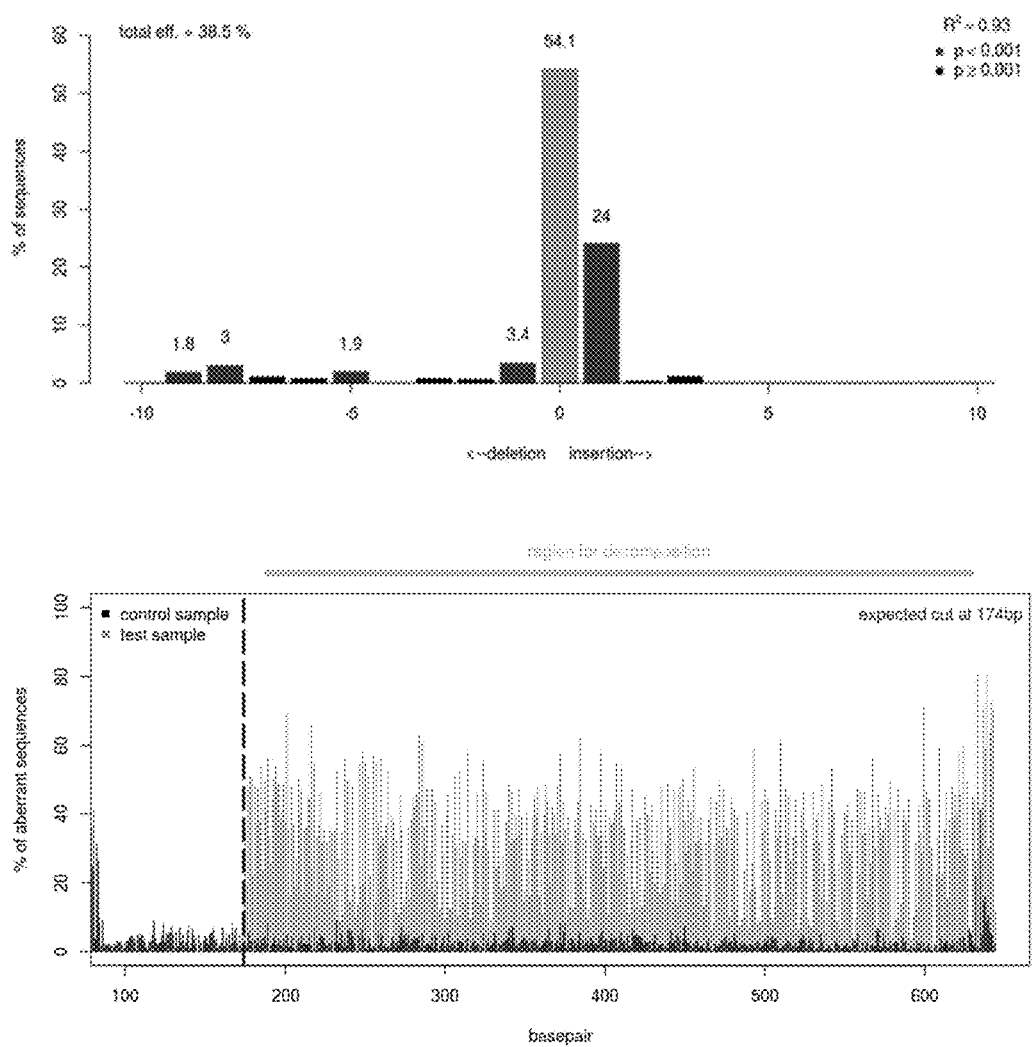
FIG. 6: shows the indel spectrum for a comparative gRNA guide (non-UNA guide structure) for assessment of genome editing of V30M TTR by sequence trace decomposition (TIDE).

FIG. 6 shows the indel spectrum for a comparative gRNA guide (non-UNA guide structure) for assessment of genome editing of V30M TTR by sequence trace decomposition (TIDE). The total efficiency was 38.5%.

Figure 7:
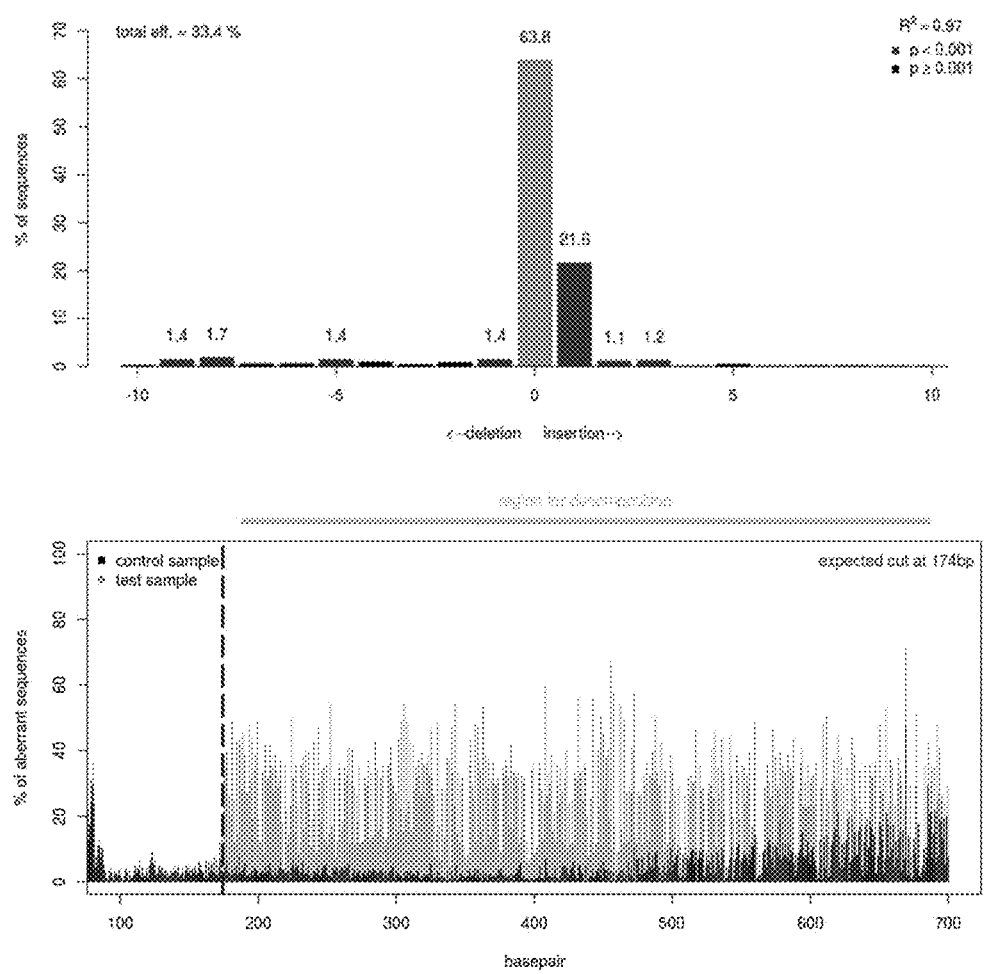
FIG. 7: shows the indel spectrum for UNA-guide (UNA1) for assessment of genome editing of V30M TTR by sequence trace decomposition (TIDE).

FIG. 7 shows the indel spectrum for UNA-guide (UNA1) for assessment of genome editing of V30M TTR by sequence trace decomposition (TIDE). The total efficiency was 33.4%.

Figure 8:
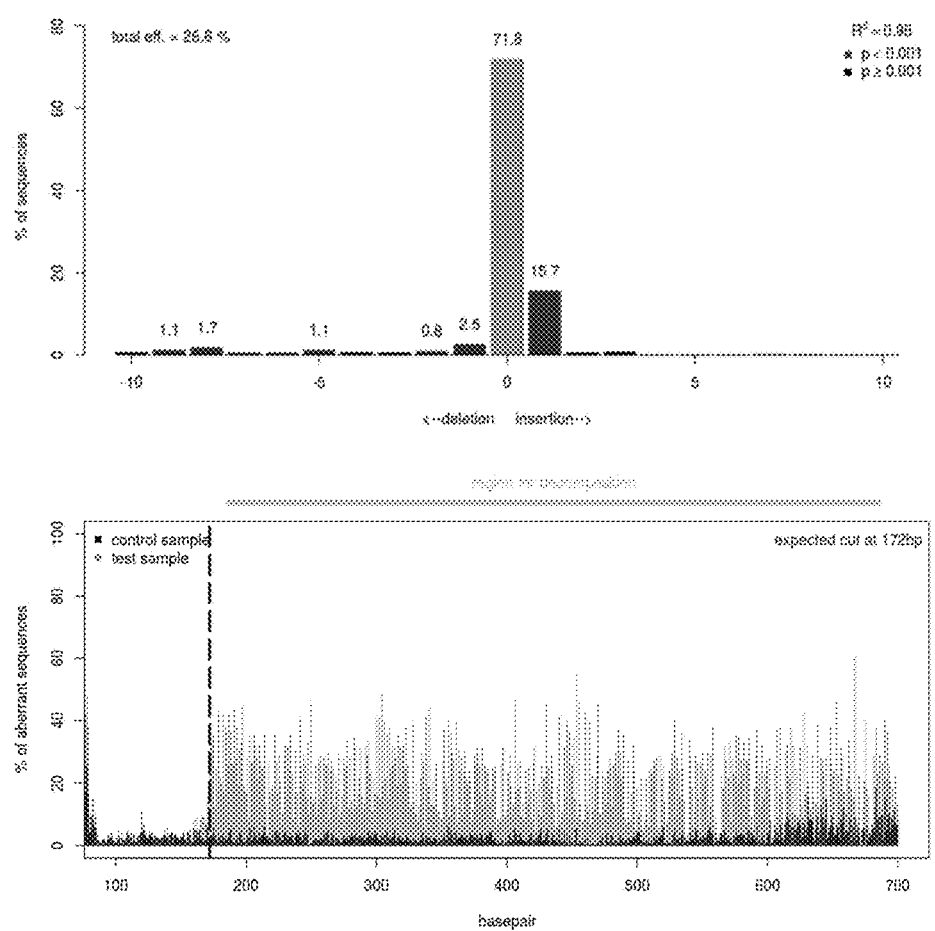
FIG. 8: shows the indel spectrum for a comparative gRNA guide (non-UNA guide structure) for assessment of genome editing of Wild Type TTR by sequence trace decomposition (TIDE).

FIG. 8 shows the indel spectrum for a comparative gRNA guide (non-UNA guide structure) for assessment of genome editing of Wild Type TTR by sequence trace decomposition (TIDE). The total efficiency was 26.6%. Thus, the selectivity of the comparative gRNA guide was 38.5/26.6=1.4 for V30M TTR over Wild Type TTR.

Figure 9:
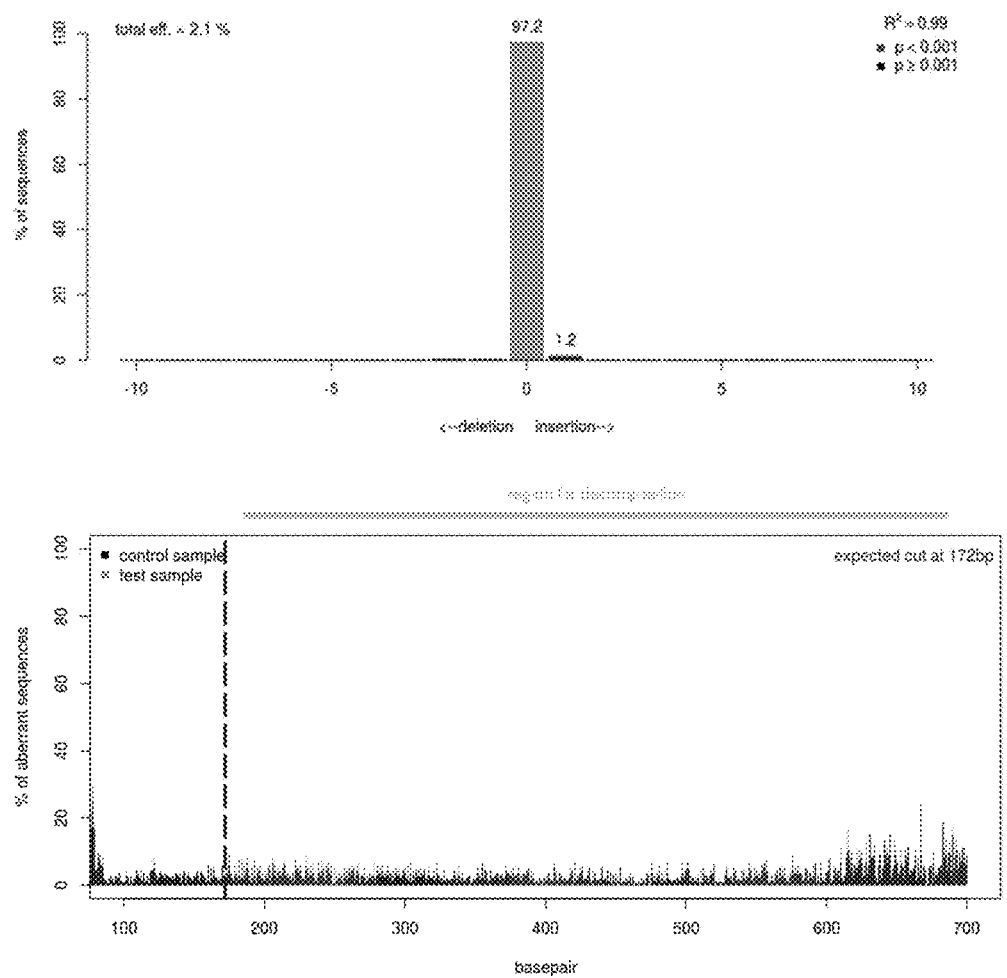
FIG. 9: shows the indel spectrum for UNA-guide (UNA1) for assessment of genome editing of Wild Type TTR by sequence trace decomposition (TIDE).

FIG. 9 shows the indel spectrum for UNA-guide (UNA1) for assessment of genome editing of Wild Type TTR by sequence trace decomposition (TIDE). The total efficiency was 2.1%. Thus, the selectivity of the UNA-guide (UNA1) was 33.4/2.1=15.9 for V30M TTR over Wild Type TTR.

These results show that the U-Guide molecules of this invention can be used for allele selective gene editing of human TTR. The U-Guide molecules of this invention exhibited a surprisingly high level of allele selectivity for gene editing of human TTR.

Example 2

Allele Selective Editing of a TTR Genomic Site with a U-Guide Molecule for CRISPR/Cas9

A 20-mer guide sequence for V30M hTTR is shown in Table 8.

TABLE 8

20-mer guide sequence for V30M hTTR

| SEQ ID NO. | SEQUENCE |
| --- | --- |
| 40 | 3'-AGUUACACCGGUACGUACAC-5' (TARGET GUIDE) |
| 41 | 5'-CCA-TCAATGTGGCCATGCATGTG-3' (V30M TTR GENE) |
| 42 | 3'-GGT-AGTTACACCGGTACGTACAC-5' (V30M TTR GENE) |

In Table 8, SEQ ID NO:40 can also be written in the 5' to 3' direction, and appears in the U-Guide molecules of Table 9 written in the 5' to 3' direction.

As used herein, the term "1 or 5' to 3'" refers to U-Guides having either a UNA monomer on the leftmost end (1 to 3', for example SEQ ID NO:43) or a nucleotide on the leftmost end (5' to 3', for example SEQ ID NO:44).

A U-Guide molecule was synthesized, wherein the molecule contained the 20-mer guide sequence for V30M and a CRISPR sequence of S. pyogenes.

Examples of 20-mer target length U-Guide molecules for the V30M region of hTTR are shown in Table 9.

TABLE 9

20-mer target length U-Guide molecules for editing the V30M region of hTTR

| SEQ ID NO. | U-GUIDE STRUCTURE (1 or 5' to 3') |
| --- | --- |
| 43 |ČACAUGCAUGGCCACAUUGAGUUUUAGAGCUAUGCU |
| 44 | CÃCAUGCAUGGCCACAUUGAGUUUUAGAGCUAUGCU |
| 45 | CAČAUGCAUGGCCACAUUGAGUUUUAGAGCUAUGCU |
| 46 | CACÃUGCAUGGCCACAUUGAGUUUUAGAGCUAUGCU |
| 47 | CACAUGCAUGGCCACAUUGAGUUUUAGAGCUAUGCŨ |
| 48 | CACAUGCAUGGCCACAUUGAGUUUUAGAGCUAUGČU |
| 49 | CACAUGCAUGGCCACAUUGAGUUUUAGAGCUAUĜCU |
| 50 | CACAUGCAUGGCCACAUUGAGUUUUAGAGCUAŨGCU |
| 51 | ČmAmCAUGCAUGGCCACAUUGAGUUUUAGAGCUAUmGmCmU |
| 52 | mCÃmCAUGCAUGGCCACAUUGAGUUUUAGAGCUAUmGmCmU |
| 53 | mCmAČAUGCAUGGCCACAUUGAGUUUUAGAGCUAUmGmCmU |
| 54 | mCmAmCÃUGCAUGGCCACAUUGAGUUUUAGAGCUAUmGmCmU |
| 55 | mCmAmCAUGCAUGGCCACAUUGAGUUUUAGAGCUAUmGmCŨ |
| 56 | mCmAmCAUGCAUGGCCACAUUGAGUUUUAGAGCUAUmGČmU |
| 57 | mCmAmCAUGCAUGGCCACAUUGAGUUUUAGAGCUAUĜmCmU |
| 58 | mCmAmCAUGCAUGGCCACAUUGAGUUUUAGAGCUAŨmGmCmU |
| 59 | Č*mA*mC*AUGCAUGGCCACAUUGAGUUUUAGAGCUAU*mG*mC*mU |
| 60 | mC*Ã*mC*AUGCAUGGCCACAUUGAGUUUUAGAGCUAU*mG*mC*mU |
| 61 | mC*mA*Č*AUGCAUGGCCACAUUGAGUUUUAGAGCUAU*mG*mC*mU |

TABLE 9-continued 20-mer target length U-Guide molecules for editing the V30M region of hTTR

| SEQ ID NO. | U-GUIDE STRUCTURE (1 or 5' to 3') |
|---|---|
| 62 | mC*mA*mC*ÃUGCAUGGCCACAUUGAGUUUUAGAGCUAU*mG*mC*mU |
| 63 | mC*mA*mC*AUGCAUGGCCACAUUGAGUUUUAGAGCUAU*mG*mC*Ũ |
| 64 | mC*mA*mC*AUGCAUGGCCACAUUGAGUUUUAGAGCUAU*mG*Č*mU |
| 65 | mC*mA*mC*AUGCAUGGCCACAUUGAGUUUUAGAGCUAU*Ĝ*mC*mU |
| 66 | mC*mA*mC*AUGCAUGGCCACAUUGAGUUUUAGAGCUAŨ*mG*mC*mU |

In Table 9, N (=A, U, C, G) designates an RNA monomer, mN designates a 2'-O-methyl-RNA monomer, * designates a 3'-phosphorothioate linkage, and Ã, Ũ, Č, Ĝ designate UNA monomers.

A U-Guide molecule in Table 9 was active for gene editing human TTR. An assay for gene editing human TTR was performed with the 357 by PCR product. In this assay, the U-Guide molecule is pre-annealed with a tracrRNA to provide a the U-Guide/tracr for CRISPR/Cas9 gene editing.

In the assay, 293 cells expressing V30M human TTR and 293 cells expressing WT human TTR were each transfected using LIPOFECTAMINE MESSENGER MAX reagent with Cas9 mRNA 4 hours prior to transfection with the U-Guide/tracr. 48 h following transfection, genomic DNA was isolated, and the T7 endonuclease assay performed.

Figure 10:
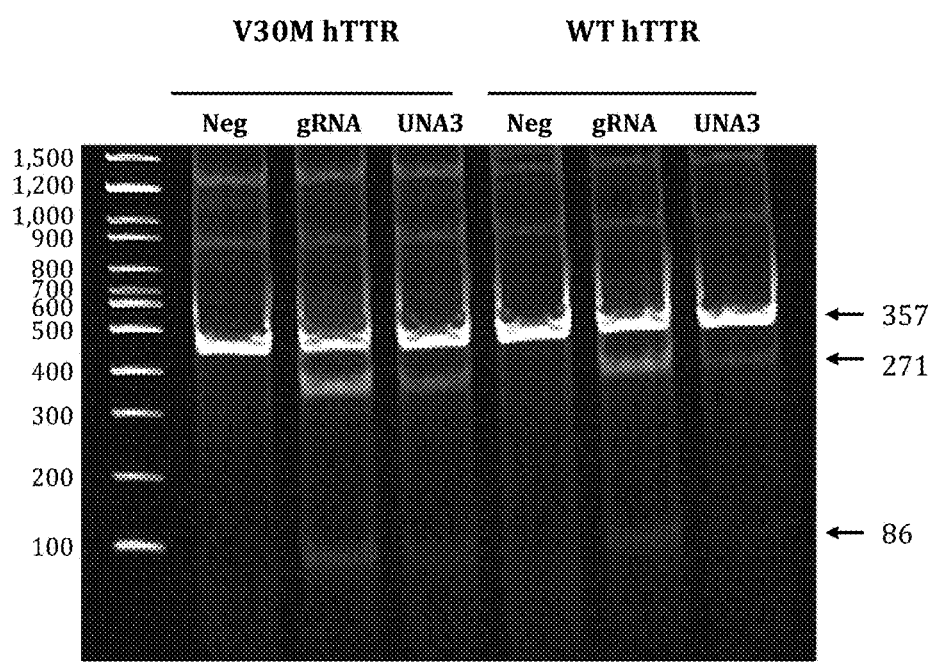
FIG. 10: Allele selective gene editing of a transthyretin (TTR) genomic site with a U-Guide molecule for CRISPR/Cas9.

FIG. 10 shows that using U-Guide molecule UNA3 (SEQ ID NO:61), a double strand break was made in the 357 by PCR product to give 271 by and 86 by cleavage products.

The U-Guide molecule SEQ ID NO:61 was surprisingly active for gene editing human TTR with allele selective results. The U-Guide molecule SEQ ID NO:61 showed an extraordinary level of allele selectivity for generating double strand breaks in V30M TTR over wild type TTR.

Figure 11:
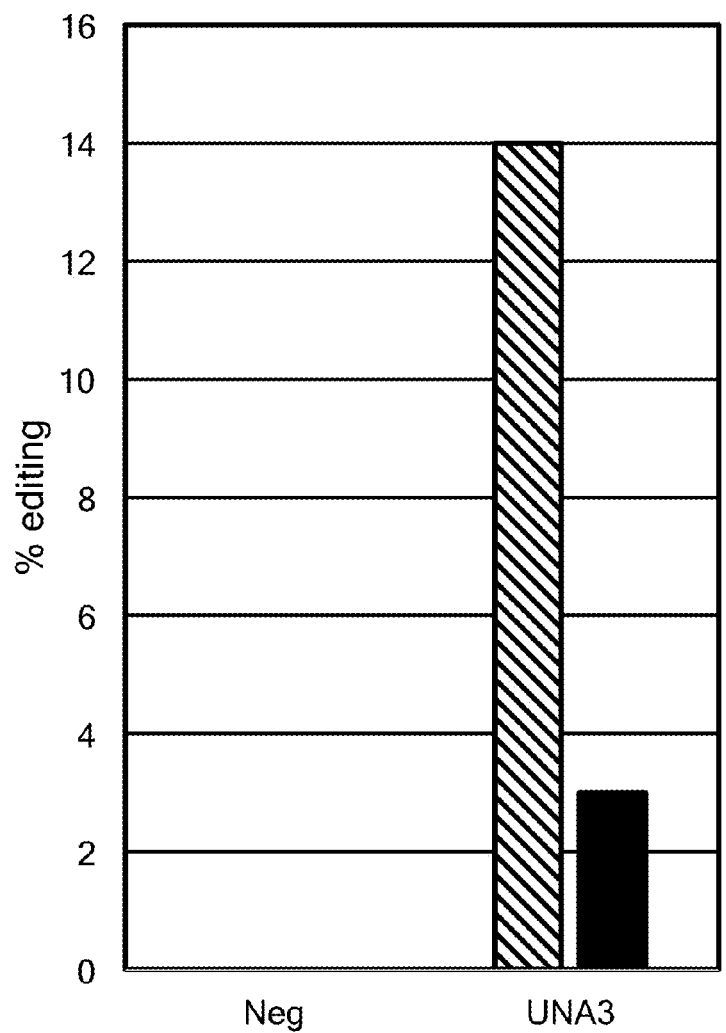
FIG. 11: shows that a U-Guide molecule UNA3 of this invention provided selective editing of V30M TTR over wild type TTR in a CRISPR/Cas9 system. The U-Guide molecule UNA3 produced high levels of double strand breaks in V30M TTR (patterned bar), but surprisingly few double strand breaks in wild type TTR (black bar). Thus, the U-Guide molecule UNA3 of this invention was extraordinarily active for allele selective gene editing of human TTR. This indicates the capability for reduced off target activity. The Neg control contained no CRISPR/tracr guide.

As shown in FIG. 11, the U-Guide molecule SEQ ID NO:61 provided 14% editing of V30M TTR, but only about 3% editing of wild type TTR, where the editing represents the degree of double strand breaks. Thus, the U-Guide molecule SEQ ID NO:62 was surprisingly and extraordinarily active for gene editing human TTR with allele selective results. This example indicates the capability for reduced off target activity.

Figure 12:
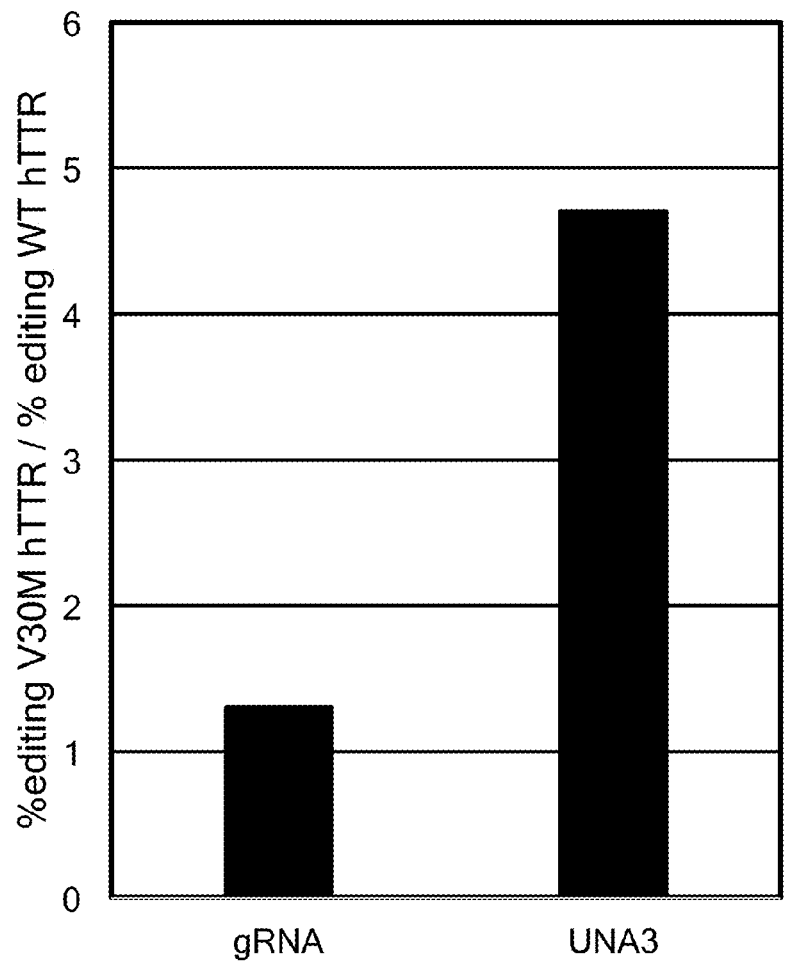
FIG. 12: The U-Guide molecules of this invention can be used for allele selective gene editing of human TTR. The surprising level of allele selectivity for gene editing of human TTR is shown in FIG. 12. The U-Guide molecule UNA3 provided high a selectivity ratio of 4.7. This indicates the capability for reduced off target activity. Further, under the same conditions, a CRISPR/Cas9 guide (gRNA) having the same nucleobase sequence and structure as the U-Guide molecule, but lacking any UNA monomer, exhibited a selectivity ratio of 1.3. Thus, the U-Guide molecule UNA3 was extraordinarily active for gene editing human TTR with allele selectivity of V30M TTR over wild type TTR.

These results show that the U-Guide molecules of this invention can be used for allele selective gene editing of human TTR. The surprising level of allele selectivity for gene editing of human TTR is shown in FIG. 12. The U-Guide molecule SEQ ID NO:61 provided a high selectivity ratio of 4.7.

Thus, the U-Guide molecule SEQ ID NO:62 was extraordinarily active for gene editing human TTR with allele selectivity of V30M TTR over wild type TTR. This example indicates the capability for reduced off target activity.

Example 3

Editing a BIRC5 Genomic Site with a U-Guide Molecule for CRISPR/Cas9

Survivin (baculoviral inhibitor of apoptosis repeat-containing 5, human BIRC5, NG_029069.1) can be expressed in tumor cells, especially in breast and lung cancer, and is generally not present in normal cells. Survivin may be an oncogene, and its overexpression in cancer cells may lead to resistance to apoptosis, and increased survival.

Guide sequences of 20-mer length were identified that targeted certain regions of human BIRC5. The EntreZ Gene ID for these sequences is 332.

20-mer guide sequences for BIRC5 are shown in Table 10.

TABLE 10

20-mer guide sequences for BIRC5

| SEQ ID NO. | TARGET SEQUENCE 5' -> 3' |
|---|---|
| 67 | GAUGCGGUGGUCCUUGAGAA |
| 68 | CAAGAACUGGCCCUUCUUGG |
| 69 | GCAGGCGCAGCCCUCCAAGA |
| 70 | UUCUGCUUCAAGGAGCUGGA |
| 71 | CCAGUUUCAAAAAUUCACCA |
| 72 | CAAUAAGAAGAAAGAAUUUG |

A U-Guide molecule is synthesized, wherein the molecule contains the 20-mer target sequence and a CRISPR sequence of S. pyogenes.

Examples of 20-mer target length U-Guide molecules for BIRC5 are shown in Table 11.

TABLE 11

20-mer target length U-Guide molecules for editing BIRC5

| SEQ ID NO. | U-GUIDE STRUCTURE (1 or 5' to 3') |
|---|---|
| 73 | GAUGCGGUGGUCCUUGAGAAGUUUUAGAGCUAUGCUGUCCUU |
| 74 | ŨGAUGCGGUGGUCCUUGAGAAGUUUUAGAGCUAUGCUGUCCUU |
| 75 | UĜAUGCGGUGGUCCUUGAGAAGUUUUAGAGCUAUGCUGUCCUU |
| 76 | U*ĜAUGCGGUGGUCCUUGAGAAGUUUUAGAGCUAUGCUGUCCU*U |
| 77 | mUUUGAUGCGGUGGUCCUUGAGAAGUUUUAGAGCUAUGCUGUCCUUUmU |

TABLE 11-continued 20-mer target length U-Guide molecules for editing BIRC5

| SEQ ID NO. | U-GUIDE STRUCTURE (1 or 5' to 3') |
|---|---|
| 78 | mU*UUGAUGCGGUGGUCCUUGAGAAGUUUUAGAGCUAUGCUGUCCUUU*mU |
| 79 | mU*U*UGAUGCGGUGGUCCUUGAGAAGUUUUAGAGCUAUGCUGUCCUU*U*mU |
| 80 | mU*U*U*GAUGCGGUGGUCCUUGAGAAGUUUUAGAGCUAUGCUGUCCU*U*U*mU |
| 81 | mU*UUGAUGCGGUGGUCCUUGAGAAGUUUUAGAGCUAUGCUGUCCUUU*mU |
| 82 | mU*U*UGAUGCGGUGGUCCUUGAGAAGUUUUAGAGCUAUGCUGUCCUU*U*mU |
| 83 | mU*U*U*GAUGCGGUGGUCCUUGAGAAGUUUUAGAGCUAUGCUGUCCU*U*U*mU |
| 84 | CAAGAACUGGCCCUUCUUGGGUUUUAGAGCUAUGCUGUCCUU |
| 85 | UCAAGAACUGGCCCUUCUUGGGUUUUAGAGCUAUGCUGUCCUU |
| 86 | UĈAAGAACUGGCCCUUCUUGGGUUUUAGAGCUAUGCUGUCCUU |
| 87 | U*ĈAAGAACUGGCCCUUCUUGGGUUUUAGAGCUAUGCUGUCCU*U |
| 88 | mUUCAAGAACUGGCCCUUCUUGGGUUUUAGAGCUAUGCUGUCCUUUmU |
| 89 | mU*UCAAGAACUGGCCCUUCUUGGGUUUUAGAGCUAUGCUGUCCUUU*mU |
| 90 | mU*U*CAAGAACUGGCCCUUCUUGGGUUUUAGAGCUAUGCUGUCCUU*U*mU |
| 91 | mU*U*U*CAAGAACUGGCCCUUCUUGGGUUUUAGAGCUAUGCUGUCCU*U*U*mU |
| 92 | mU*UUCAAGAACUGGCCCUUCUUGGGUUUUAGAGCUAUGCUGUCCUUU*mU |
| 93 | mU*U*UCAAGAACUGGCCCUUCUUGGGUUUUAGAGCUAUGCUGUCCUU*U*mU |
| 94 | mU*U*U*CAAGAACUGGCCCUUCUUGGGUUUUAGAGCUAUGCUGUCCU*U*U*mU |
| 95 | GCAGGCGCAGCCCUCCAAGAGUUUUAGAGCUAUGCUGUCCUU |
| 96 | UGCAGGCGCAGCCCUCCAAGAGUUUUAGAGCUAUGCUGUCCUU |
| 97 | UĜCAGGCGCAGCCCUCCAAGAGUUUUAGAGCUAUGCUGUCCUU |
| 98 | U*ĜCAGGCGCAGCCCUCCAAGAGUUUUAGAGCUAUGCUGUCCU*U |
| 99 | mUOGCAGGCGCAGCCCUCCAAGAGUUUUAGAGCUAUGCUGUCCUUUmU |
| 100 | mU*UGCAGGCGCAGCCCUCCAAGAGUUUUAGAGCUAUGCUGUCCUUU*mU |
| 101 | mU*U*GCAGGCGCAGCCCUCCAAGAGUUUUAGAGCUAUGCUGUCCUU*U*mU |
| 102 | mU*U*U*GCAGGCGCAGCCCUCCAAGAGUUUUAGAGCUAUGCUGUCCU*U*U*mU |
| 103 | mU*UUGCAGGCGCAGCCCUCCAAGAGUUUUAGAGCUAUGCUGUCCUUU*mU |
| 104 | mU*U*UGCAGGCGCAGCCCUCCAAGAGUUUUAGAGCUAUGCUGUCCUU*U*mU |
| 105 | mU*U*U*GCAGGCGCAGCCCUCCAAGAGUUUUAGAGCUAUGCUGUCCU*U*U*mU |
| 106 | UUCUGCUUCAAGGAGCUGGAGUUUUAGAGCUAUGCUGUCCUU |
| 107 | UUUCUGCUUCAAGGAGCUGGAGUUUUAGAGCUAUGCUGUCCUU |
| 108 | UUUCUGCUUCAAGGAGCUGGAGUUUUAGAGCUAUGCUGUCCUU |
| 109 | U*ŨUCUGCUUCAAGGAGCUGGAGUUUUAGAGCUAUGCUGUCCU*U |
| 110 | mUUUUCUGCUUCAAGGAGCUGGAGUUUUAGAGCUAUGCUGUCCUUUmU |
| 111 | mU*UUUCUGCUUCAAGGAGCUGGAGUUUUAGAGCUAUGCUGUCCUUU*mU |

TABLE 11-continued 20-mer target length U-Guide molecules for editing BIRC5

| SEQ ID NO. | U-GUIDE STRUCTURE (1 or 5' to 3') |
|---|---|
| 112 | mU*U*UUCUGCUUCAAGGAGCUGGAGUUUUAGAGCUAUGCUGUCCUU*U*mU |
| 113 | mU*U*U*UUCUGCUUCAAGGAGCUGGAGUUUUAGAGCUAUGCUGUCCU*U*U*mU |
| 114 | mU*UUUCUGCUUCAAGGAGCUGGAGUUUUAGAGCUAUGCUGUCCUUU*mU |
| 115 | mU*U*UUUCUGCUUCAAGGAGCUGGAGUUUUAGAGCUAUGCUGUCCUU*U*mU |
| 116 | mU*U*U*UUCUGCUUCAAGGAGCUGGAGUUUUAGAGCUAUGCUGUCCU*U*U*mU |
| 117 | CCAGUUUCAAAAAUUCACCAGUUUUAGAGCUAUGCUGUCCUU |
| 118 | UCCAGUUUCAAAAAUUCACCAGUUUUAGAGCUAUGCUGUCCUU |
| 119 | UĈCAGUUUCAAAAAUUCACCAGUUUUAGAGCUAUGCUGUCCUU |
| 120 | U*ĈCAGUUUCAAAAAUUCACCAGUUUUAGAGCUAUGCUGUCCU*U |
| 121 | mUUCCAGUUUCAAAAAUUCACCAGUUUUAGAGCUAUGCUGUCCUUUmU |
| 122 | mU*UCCAGUUUCAAAAAUUCACCAGUUUUAGAGCUAUGCUGUCCUUU*mU |
| 123 | mU*U*CCAGUUUCAAAAAUUCACCAGUUUUAGAGCUAUGCUGUCCUU*U*mU |
| 124 | mU*U*U*CCAGUUUCAAAAAUUCACCAGUUUUAGAGCUAUGCUGUCCU*U*U*mU |
| 125 | mU*UUCCAGUUUCAAAAAUUCACCAGUUUUAGAGCUAUGCUGUCCUUU*mU |
| 126 | mU*U*UCCAGUUUCAAAAAUUCACCAGUUUUAGAGCUAUGCUGUCCUU*U*mU |
| 127 | mU*U*U*CCAGUUUCAAAAAUUCACCAGUUUUAGAGCUAUGCUGUCCU*U*U*mU |
| 128 | CAAUAAGAAGAAAGAAUUUGGUUUUAGAGCUAUGCUGUCCUU |
| 129 | UCAAUAAGAAGAAAGAAUUUGGUUUUAGAGCUAUGCUGUCCUU |
| 130 | UĈAAUAAGAAGAAAGAAUUUGGUUUUAGAGCUAUGCUGUCCUU |
| 131 | U*ĈAAUAAGAAGAAAGAAUUUGGUUUUAGAGCUAUGCUGUCCU*U |
| 132 | mUUCAAUAAGAAGAAAGAAUUUGGUUUUAGAGCUAUGCUGUCCUUUmU |
| 133 | mU*UCAAUAAGAAGAAAGAAUUUGGUUUUAGAGCUAUGCUGUCCUUU*mU |
| 134 | mU*U*CAAUAAGAAGAAAGAAUUUGGUUUUAGAGCUAUGCUGUCCUU*U*mU |
| 135 | mU*U*U*CAAUAAGAAGAAAGAAUUUGGUUUUAGAGCUAUGCUGUCCU*U*U*mU |
| 136 | mU*UUCAAUAAGAAGAAAGAAUUUGGUUUUAGAGCUAUGCUGUCCUUU*mU |
| 137 | mU*U*UCAAUAAGAAGAAAGAAUUUGGUUUUAGAGCUAUGCUGUCCUU*U*mU |
| 138 | mU*U*U*CAAUAAGAAGAAAGAAUUUGGUUUUAGAGCUAUGCUGUCCU*U*U*mU |

In Table 11, N designates an RNA monomer, mN designates a 2'-O-methyl-RNA monomer, * designates a 3'-phosphorothioate linkage, Ũ designates a UNA-U monomer, and Ĝ designates a UNA-G monomer.

Example 4

Editing a CDK16 Genomic Site with a U-Guide Molecule for CRISPR/Cas9

The protein encoded by CDK16 belongs to the cdc2/cdkx subfamily of the ser/thr family of protein kinases (human CDK16, NG_012517.1). CDK16 may be associated with in signal transduction cascades in terminally differentiated cells, in exocytosis, and in transport of secretory cargo from the endoplasmic reticulum. Defects and copy-number variants of CDK16 have been associated with various diseases, including intellectual disability and related disorders.

Guide sequences of 20-mer length were identified that targeted certain regions of human CDK16. The EntreZ Gene ID for these sequences is 5127.

20-mer guide sequences for CDK16 are shown in Table 12.

TABLE 12

20-mer guide sequences for CDK16

| SEQ ID NO. | TARGET SEQUENCE 5' -> 3' |
|---|---|
| 139 | CGUGCAGAACGAAGUUCCCC |
| 140 | UGGAGACUGCACCUCAUCCG |
| 141 | UGAUCUCCUUGAGUGCCACA |
| 142 | UGAUGUUCCCACAGUCAUCC |
| 143 | AGUAGUCCGUGGACCCAAGC |
| 144 | CUACCCCAAGUACCGAGCCG |

A U-Guide molecule is synthesized, wherein the molecule contains the 20-mer target sequence and a CRISPR sequence of S. pyogenes.

Examples of 20-mer target length U-Guide molecules for CDK16 are shown in Table 13.

TABLE 13

20-mer target length U-Guide molecules for editing CDK16

| SEQ ID NO. | U-GUIDE STRUCTURE (1 or 5' to 3') |
|---|---|
| 145 | CGUGCAGAACGAAGUUCCCCGUUUUAGAGCUAUGCUGUCCUU |
| 146 | UCGUGCAGAACGAAGUUCCCCGUUUUAGAGCUAUGCUGUCCUU |
| 147 | UĈGUGCAGAACGAAGUUCCCCGUUUUAGAGCUAUGCUGUCCUU |
| 148 | U*ĈGUGCAGAACGAAGUUCCCCGUUUUAGAGCUAUGCUGUCCU*U |
| 149 | mUŨCCGUGCAGCAACGAAGUUCCCCGUUUUAGAGCUAUGCUGUCCUUUmU |
| 150 | mU*UCGUGCAGAACGAAGUUCCCCGUUUUAGAGCUAUGCUGUCCUU*mU |
| 151 | mU*U*CGUGCAGAACGAAGUUCCCCGUUUUAGAGCUAUGCUGUCCUU*U*mU |
| 152 | mU*U*U*CGUGCAGAACGAAGUUCCCCGUUUUAGAGCUAUGCUGUCCU*U*U*mU |
| 153 | mU*UUCGUGCAGAACGAAGUUCCCCGUUUUAGAGCUAUGCUGUCCUU*mU |
| 154 | mU*U*UCGUGCAGAACGAAGUUCCCCGUUUUAGAGCUAUGCUGUCCUU*U*mU |
| 155 | mU*U*U*CGUGCAGAACGAAGUUCCCCGUUUUAGAGCUAUGCUGUCCU*U*U*mU |
| 156 | UGGAGACUGCACCUCAUCCGGUUUUAGAGCUAUGCUGUCCUU |
| 157 | UUGGAGACUGCACCUCAUCCGGUUUUAGAGCUAUGCUGUCCUU |
| 158 | CUGGAGACUGCACCUCAUCCGGUUUUAGAGCUAUGCUGUCCUU |
| 159 | U*UGGAGACUGCACCUCAUCCGGUUUUAGAGCUAUGCUGUCCU*U |
| 160 | mUUUGGAGACUGCACCUCAUCCGGUUUUAGAGCUAUGCUGUCCUUUmU |
| 161 | mU*UUGGAGACUGCACCUCAUCCGGUUUUAGAGCUAUGCUGUCCUUU*mU |
| 162 | mU*U*UGGAGACUGCACCUCAUCCGGUUUUAGAGCUAUGCUGUCCUU*U*mU |
| 163 | mU*U*U*UGGAGACUGCACCUCAUCCGGUUUUAGAGCUAUGCUGUCCU*U*U*mU |
| 164 | mU*CUUGGAGACUGCACCUCAUCCGGUUUUAGAGCUAUGCUGUCCUUU*mU |
| 165 | mU*U*UUGGAGACUGCACCUCAUCCGGUUUUAGAGCUAUGCUGUCCUU*U*mU |
| 166 | mU*U*U*UGGAGACUGCACCUCAUCCGGUUUUAGAGCUAUGCUGUCCU*U*U*mU |
| 167 | UGAUCUCCUUGAGUGCCACAGUUUUAGAGCUAUGCUGUCCUU |

TABLE 13-continued 20-mer target length U-Guide molecules for editing CDK16

| SEQ ID NO. | U-GUIDE STRUCTURE (1 or 5' to 3') |
|---|---|
| 168 | UUGAUCUCCUUGAGUGCCACAGUUUUAGAGCUAUGCUGUCCUU |
| 169 | CUGAUCUCCUUGAGUGCCACAGUUUUAGAGCUAUGCUGUCCUU |
| 170 | U*UGAUCUCCUUGAGUGCCACAGUUUUAGAGCUAUGCUGUCCU*U |
| 171 | mUUUGAUCUCCUUGAGUGCCACAGUUUUAGAGCUAUGCUGUCCUUUmU |
| 172 | mU*UUGAUCUCCUUGAGUGCCACAGUUUUAGAGCUAUGCUGUCCUUU*mU |
| 173 | mU*U*UGAUCUCCUUGAGUGCCACAGUUUUAGAGCUAUGCUGUCCUU*U*mU |
| 174 | mU*U*U*UGAUCUCCUUGAGUGCCACAGUUUUAGAGCUAUGCUGUCCU*U*U*mU |
| 175 | mU*CUUGAUCUCCUUGAGUGCCACAGUUUUAGAGCUAUGCUGUCCUUU*mU |
| 176 | mU*U*UUGAUCUCCUUGAGUGCCACAGUUUUAGAGCUAUGCUGUCCUU*U*mU |
| 177 | mU*U*U*UGAUCUCCUUGAGUGCCACAGUUUUAGAGCUAUGCUGUCCU*U*U*mU |
| 178 | UGAUGUUCCCACAGUCAUCCGUUUUAGAGCUAUGCUGUCCUU |
| 179 | UUGAUGUUCCCACAGUCAUCCGUUUUAGAGCUAUGCUGUCCUU |
| 180 | CUGAUGUUCCCACAGUCAUCCGUUUUAGAGCUAUGCUGUCCUU |
| 181 | U*UGAUGUUCCCACAGUCAUCCGUUUUAGAGCUAUGCUGUCCU*U |
| 182 | mUUUGAUGUUCCCACAGUCAUCCGUUUUAGAGCUAUGCUGUCCUUUmU |
| 183 | mU*UUGAUGUUCCCACAGUCAUCCGUUUUAGAGCUAUGCUGUCCUUU*mU |
| 184 | mU*U*UGAUGUUCCCACAGUCAUCCGUUUUAGAGCUAUGCUGUCCUU*U*mU |
| 185 | mU*U*U*UGAUGUUCCCACAGUCAUCCGUUUUAGAGCUAUGCUGUCCU*U*U*mU |
| 186 | mU*CUUGAUGUUCCCACAGUCAUCCGUUUUAGAGCUAUGCUGUCCUUU*mU |
| 187 | mU*U*UUGAUGUUCCCACAGUCAUCCGUUUUAGAGCUAUGCUGUCCUU*U*mU |
| 188 | mU*U*U*UGAUGUUCCCACAGUCAUCCGUUUUAGAGCUAUGCUGUCCU*U*U*mU |
| 189 | AGUAGUCCGUGGACCCAAGCGUUUUAGAGCUAUGCUGUCCUU |
| 190 | CAGUAGUCCGUGGACCCAAGCGUUUUAGAGCUAUGCUGUCCUU |
| 191 | ŨÃGUAGUCCGUGGACCCAAGCGUUUUAGAGCUAUGCUGUCCUU |
| 192 | U*ÃGUAGUCCGUGGACCCAAGCGUUUUAGAGCUAUGCUGUCCU*U |
| 193 | mUCAGUAGUCCGUGGACCCAAGCGUUUUAGAGCUAUGCUGUCCUUUmU |
| 194 | mU*UAGUAGUCCGUGGACCCAAGCGUUUUAGAGCUAUGCUGUCCUUU*mU |
| 195 | mU*U*AGUAGUCCGUGGACCCAAGCGUUUUAGAGCUAUGCUGUCCUU*U*mU |
| 196 | mu*U*U*AGUAGUCCGUGGACCCAAGCGUUUUAGAGCUAUGCUGUCCU*U*U*mU |
| 197 | mU*UUAGUAGUCCGUGGACCCAAGCGUUUUAGAGCUAUGCUGUCCUUU*mU |
| 198 | mU*U*UAGUAGUCCGUGGACCCAAGCGUUUUAGAGCUAUGCUGUCCUU*U*mU |
| 199 | mU*U*U*AGUAGUCCGUGGACCCAAGCGUUUUAGAGCUAUGCUGUCCU*U*U*mU |
| 200 | CUACCCCAAGUACCGAGCCGGUUUUAGAGCUAUGCUGUCCUU |
| 201 | UCUACCCCAAGUACCGAGCCGGUUUUAGAGCUAUGCUGUCCUU |
| 202 | UĈUACCCCAAGUACCGAGCCGGUUUUAGAGCUAUGCUGUCCUU |
| 203 | U*ĈUACCCCAAGUACCGAGCCGGUUUUAGAGCUAUGCUGUCCU*U |
| 204 | mUCCUACCCCAAGUACCGAGCCGGUUUUAGAGCUAUGCUGUCCUUUmU |

TABLE 13-continued 20-mer target length U-Guide molecules for editing CDK16

| SEQ ID NO. | U-GUIDE STRUCTURE (1 or 5' to 3') |
|---|---|
| 205 | mU*UCUACCCCAAGUACCGAGCCGGUUUUAGAGCUAUGCUGUCCUUU*mU |
| 206 | mU*U*CUACCCCAAGUACCGAGCCGGUUUUAGAGCUAUGCUGUCCUU*U*mU |
| 207 | mU*U*U*CUACCCCAAGUACCGAGCCGGUUUUAGAGCUAUGCUGUCCU*U*U*mU |
| 208 | mU*UCCUACCCCAAGUACCGAGCCGGUUUUAGAGCUAUGCUGUCCUUU*mU |
| 209 | mU*U*UCUACCCCAAGUACCGAGCCGGUUUUAGAGCUAUGCUGUCCUU*U*mU |
| 210 | mU*U*U*CUACCCCAAGUACCGAGCCGGUUUUAGAGCUAUGCUGUCCU*U*U*mU |

In Table 13, N designates an RNA monomer, mN designates a 2'-O-methyl-RNA monomer, * designates a 3'-phosphorothioate linkage, Ũ designates a UNA-U monomer, and Ĝ designates a UNA-G monomer.

Example 5

Editing a STAT3 Genomic Site with a U-Guide Molecule for CRISPR/Cas9

Signal transducer and activator of transcription 3 (STAT3) is a transcriptional mediator for many cytokines (human STAT3, NG_007370.1). STAT3 belongs to the family of STAT proteins, which are activated in response to extracellular signaling proteins including the interleukin (IL)-6 family (e.g., IL-5, IL-6, IL-11), among others. STAT3 may be associated in various autoimmune disorders, such as inflammatory bowel disease (IBD), as well as liver disease, gliosis and reactive astrocytes, and other diseases and conditions.

Guide sequences of 20-mer length were identified that targeted certain regions of human STAT3. The EntreZ Gene ID for these sequences is 6774.

20-mer guide sequences for STAT3 are shown in Table 14.

TABLE 14

20-mer guide sequences for STAT3

| SEQ ID NO. | TARGET SEQUENCE 5' -> 3' |
|---|---|
| 211 | AGAGCUGAUGGAGCUGCUCC |
| 212 | ACUGCUGGUCAAUCUCUCCC |
| 213 | CUCUCUUCCGGACAUCCUGA |
| 214 | GAGACCGAGGUGUAUCACCA |
| 215 | AACCUGGGAUCAAGUGGCCG |
| 216 | GAAGGUGCUGAACCCUCAGC |

A U-Guide molecule is synthesized, wherein the molecule contains the 20-mer target sequence and a CRISPR sequence of S. pyogenes.

Examples of 20-mer target length U-Guide molecules for STAT3 are shown in Table 15.

TABLE 15

20-mer target length U-Guide molecules for editing STAT3

| SEQ ID NO. | U-GUIDE STRUCTURE (1 or 5' to 3') |
|---|---|
| 217 | AGAGCUGAUGGAGCUGCUCCGUUUUAGAGCUAUGCUGUCCUU |
| 218 | CAGAGCUGAUGGAGCUGCUCCGUUUUAGAGCUAUGCUGUCCUŨ |
| 219 | ŨÃGAGCUGAUGGAGCUGCUCCGUUUUAGAGCUAUGCUGUCCUŨ |
| 220 | Ũ*ÃGAGCUGAUGGAGCUGCUCCGUUUUAGAGCUAUGCUGUCCŨ*Ũ |
| 221 | mUCAGAGCUGAUGGAGCUGCUCCGUUUUAGAGCUAUGCUGUCCUUŨmU |
| 222 | mU*ŨAGAGCUGAUGGAGCUGCUCCGUUUUAGAGCUAUGCUGUCCUUŨ*mU |
| 223 | mU*Ũ*AGAGCUGAUGGAGCUGCUCCGUUUUAGAGCUAUGCUGUCCUU*Ũ*mU |
| 224 | mu*Ũ*U*AGAGCUGAUGGAGCUGCUCCGUUUUAGAGCUAUGCUGUCCU*U*Ũ*mU |
| 225 | mU*ŨŨAGAGCUGAUGGAGCUGCUCCGUUUUAGAGCUAUGCUGUCCUŨŨ*mU |
| 226 | mU*Ũ*CAGAGCUGAUGGAGCUGCUCCGUUUUAGAGCUAUGCUGUCCUŨ*Ũ*mU |
| 227 | mU*Ũ*Ũ*AGAGCUGAUGGAGCUGCUCCGUUUUAGAGCUAUGCUGUCCU*Ũ*Ũ*mU |

TABLE 15-continued

20-mer target length U-Guide molecules for editing STAT3

| SEQ ID NO. | U-GUIDE STRUCTURE (1 or 5' to 3') |
|---|---|
| 228 | ACUGCUGGUCAAUCUCUCCCGUUUUAGAGCUAUGCUGUCCUU |
| 229 | ŨACUGCUGGUCAAUCUCUCCCGUUUUAGAGCUAUGCUGUCCUŨ |
| 230 | ŨÃCUGCUGGUCAAUCUCUCCCGUUUUAGAGCUAUGCUGUCCUŨ |
| 231 | Ũ*ÃCUGCUGGUCAAUCUCUCCCGUUUUAGAGCUAUGCUGUCCŨ*Ũ |
| 232 | mUCACUGCUGGUCAAUCUCUCCCGUUUUAGAGCUAUGCUGUCCUUŨmU |
| 233 | mU*ŨACUGCUGGUCAAUCUCUCCCGUUUUAGAGCUAUGCUGUCCUUŨ*mU |
| 234 | mU*Ũ*ACUGCUGGUCAAUCUCUCCCGUUUUAGAGCUAUGCUGUCCUU*Ũ*mU |
| 235 | mU*Ũ*U*ACUGCUGGUCAAUCUCUCCCGUUUUAGAGCUAUGCUGUCCU*U*Ũ*mU |
| 236 | mU*CŨACUGCUGGUCAAUCUCUCCCGUUUUAGAGCUAUGCUGUCCUŨŨ*mU |
| 237 | mU*Ũ*ŨACUGCUGGUCAAUCUCUCCCGUUUUAGAGCUAUGCUGUCCUŨ*Ũ*mU |
| 238 | mU*Ũ*Ũ*ACUGCUGGUCAAUCUCUCCCGUUUUAGAGCUAUGCUGUCCU*Ũ*Ũ*mU |
| 239 | CUCUCUUCCGGACAUCCUGAGUUUUAGAGCUAUGCUGUCCUU |
| 240 | ŨCUCUCUUCCGGACAUCCUGAGUUUUAGAGCUAUGCUGUCCUŨ |
| 241 | ŨĈCUCUCUUCCGGACAUCCUGAGUUUUAGAGCUAUGCUGUCCŨŨ |
| 242 | Ũ*ĈCUCUCUUCCGGACAUCCUGAGUUUUAGAGCUAUGCUGUCCŨ*Ũ |
| 243 | mUCCUCUCUUCCGGACAUCCUGAGUUUUAGAGCUAUGCUGUCCUUŨmU |
| 244 | mU*ŨCUCUCUUCCGGACAUCCUGAGUUUUAGAGCUAUGCUGUCCUUŨ*mU |
| 245 | mU*Ũ*CUCUCUUCCGGACAUCCUGAGUUUUAGAGCUAUGCUGUCCUU*Ũ*mU |
| 246 | mU*Ũ*U*CUCUCUUCCGGACAUCCUGAGUUUUAGAGCUAUGCUGUCCU*U*Ũ*mU |
| 247 | mU*ŨCCUCUCUUCCGGACAUCCUGAGUUUUAGAGCUAUGCUGUCCUŨŨ*mU |
| 248 | mU*Ũ*ŨCUCUCUUCCGGACAUCCUGAGUUUUAGAGCUAUGCUGUCCUŨ*Ũ*mU |
| 249 | mU*Ũ*Ũ*CUCUCUUCCGGACAUCCUGAGUUUUAGAGCUAUGCUGUCCU*Ũ*Ũ*mU |
| 250 | GAGACCGAGGUGUAUCACCAGUUUUAGAGCUAUGCUGUCCUU |
| 251 | ŨGAGACCGAGGUGUAUCACCAGUUUUAGAGCUAUGCUGUCCUŨ |
| 252 | ŨĜAGACCGAGGUGUAUCACCAGUUUUAGAGCUAUGCUGUCCŨŨ |
| 253 | Ũ*ĜAGACCGAGGUGUAUCACCAGUUUUAGAGCUAUGCUGUCCŨ*Ũ |
| 254 | mUŨGAGACCGAGGUGUAUCACCAGUUUUAGAGCUAUGCUGUCCUUŨmU |
| 255 | mU*ŨGAGACCGAGGUGUAUCACCAGUUUUAGAGCUAUGCUGUCCUUŨ*mU |
| 256 | mU*Ũ*UGAGACCGAGGUGUAUCACCAGUUUUAGAGCUAUGCUGUCCUU*Ũ*mU |
| 257 | mU*Ũ*U*GAGACCGAGGUGUAUCACCAGUUUUAGAGCUAUGCUGUCCU*U*Ũ*mU |
| 258 | mU*CŨGAGACCGAGGUGUAUCACCAGUUUUAGAGCUAUGCUGUCCUŨŨ*mU |
| 259 | mU*Ũ*ŨGAGACCGAGGUGUAUCACCAGUUUUAGAGCUAUGCUGUCCUŨ*Ũ*mU |
| 260 | mU*Ũ*Ũ*GAGACCGAGGUGUAUCACCAGUUUUAGAGCUAUGCUGUCCU*Ũ*Ũ*mU |
| 261 | AACCUGGGAUCAAGUGGCCGGUUUUAGAGCUAUGCUGUCCUU |
| 262 | CAACCUGGGAUCAAGUGGCCGGUUUUAGAGCUAUGCUGUCCUŨ |
| 263 | ŨÃACCUGGGAUCAAGUGGCCGGUUUUAGAGCUAUGCUGUCCUŨ |
| 264 | Ũ*ÃACCUGGGAUCAAGUGGCCGGUUUUAGAGCUAUGCUGUCCŨ*Ũ |

TABLE 15-continued 20-mer target length U-Guide molecules for editing STAT3

| SEQ ID NO. | U-GUIDE STRUCTURE (1 or 5' to 3') |
|---|---|
| 265 | mUCAACCUGGGAUCAAGUGGCCGGUUUUAGAGCUAUGCUGUCCUUŨmU |
| 266 | mU*ŨAACCUGGGAUCAAGUGGCCGGUUUUAGAGCUAUGCUGUCCUUŨ*mU |
| 267 | mU*Ũ*AACCUGGGAUCAAGUGGCCGGUUUUAGAGCUAUGCUGUCCUU*Ũ*mU |
| 268 | mU*Ũ*U*AACCUGGGAUCAAGUGGCCGGUUUUAGAGCUAUGCUGUCCU*U*Ũ*mU |
| 269 | mU*CŨAACCUGGGAUCAAGUGGCCGGUUUUAGAGCUAUGCUGUCCUŨŨ*mU |
| 270 | mU*Ũ*CAACCUGGGAUCAAGUGGCCGGUUUUAGAGCUAUGCUGUCCUŨ*Ũ*mU |
| 271 | mU*Ũ*Ũ*AACCUGGGAUCAAGUGGCCGGUUUUAGAGCUAUGCUGUCCU*Ũ*Ũ*mU |
| 272 | GAAGGUGCUGAACCCUCAGCGUUUUAGAGCUAUGCUGUCCUU |
| 273 | ŨGAAGGUGCUGAACCCUCAGCAGUUUUAGAGCUAUGCUGUCCUŨ |
| 274 | ŨĜAAGGUGCUGAACCCUCAGCGUUUUAGAGCUAUGCUGUCCŨŨ |
| 275 | Ũ*ĜAAGGUGCUGAACCCUCAGCGUUUUAGAGCUAUGCUGUCCŨ*Ũ |
| 276 | mUŨGAAGGUGCUGAACCCUCAGCGUUUUAGAGCUAUGCUGUCCUUŨmU |
| 277 | mU*ŨGAAGGUGCUGAACCCUCAGCGUUUUAGAGCUAUGCUGUCCUUŨ*mU |
| 278 | mU*Ũ*UGAAGGUGCUGAACCCUCAGCGUUUUAGAGCUAUGCUGUCCUU*Ũ*mU |
| 279 | mU*Ũ*U*GAAGGUGCUGAACCCUCAGCGUUUUAGAGCUAUGCUGUCCU*U*Ũ*mU |
| 280 | mU*CŨGAAGGUGCUGAACCCUCAGCGUUUUAGAGCUAUGCUGUCCUŨŨ*mU |
| 281 | mU*Ũ*ŨGAAGGUGCUGAACCCUCAGCGUUUUAGAGCUAUGCUGUCCUŨ*Ũ*mU |
| 282 | mU*Ũ*Ũ*GAAGGUGCUGAACCCUCAGCGUUUUAGAGCUAUGCUGUCCU*Ũ*Ũ*mU |

In Table 15, N designates an RNA monomer, mN designates a 2'-O-methyl-RNA monomer, * designates a 3'-phosphorothioate linkage, Ũ designates a UNA-U monomer, and Ĝ designates a UNA-G monomer.

Example 6

Editing a CFTR Genomic Site with a U-Guide Molecule for CRISPR/Cas9

Cystic fibrosis (CF) is a genetic disorder that substantially affects the respiratory system, causing abnormally thick mucus linings in the lungs. The disease can lead to fatal lung infections, and may also result in various obstructions of the pancreas, hindering digestion. Symptoms of CF include persistent coughing, wheezing or shortness of breath, and an excessive appetite but poor weight gain. Deterioration is inevitable, leading to debility and eventually death. In the United States, the incidence of CF is reported to be 1 in every 3500 births.

An individual who has the disease inherits a defective cystic fibrosis CFTR gene from each parent. The defective CFTR gene produces the defective protein cystic fibrosis transmembrane conductance regulator, which does not properly regulate the movement of salt and water in and out of cells. The result is thick, sticky mucus in the respiratory, digestive and reproductive systems, as well as increased salt in sweat. There are more than one thousand possible mutations of the CFTR gene.

Guide sequences of 20-mer length were identified that targeted certain regions of human CFTR (human CFTR, NG_016465.4). The EntreZ Gene ID for these sequences is 1080.

20-mer guide sequences for CFTR are shown in Table 16.

TABLE 16

20-mer guide sequences for CFTR

| SEQ ID NO. | TARGET SEQUENCE 5' -> 3' |
|---|---|
| 283 | GGUAUAUGUCUGACAAUUCC |
| 284 | ACUCCCAGAUUAGCCCCAUG |
| 285 | AAGGACAGCCUUCUCUCUAA |
| 286 | UGCUGAUCACGCUGAUGCG |
| 287 | CUAUUCCCUUUGUCUUGAAG |
| 288 | UUCAUUGACAUGCCAACAGA |

A U-Guide molecule is synthesized, wherein the molecule contains the 20-mer target sequence and a CRISPR sequence of S. pyogenes.

Examples of 20-mer target length U-Guide molecules for CFTR are shown in Table 17.

TABLE 17

20-mer target length U-Guide molecules for editing CFTR

| SEQ ID NO. | U-GUIDE STRUCTURE (1 or 5' to 3') |
|---|---|
| 289 | GGUAUAUGUCUGACAAUUCCGUUUUAGAGCUAUGCUGUCCUU |
| 290 | ŨGGUAUAUGUCUGACAAUUCCGUUUUAGAGCUAUGCUGUCCUŨ |
| 291 | ŨĜGUAUAUGUCUGACAAUUCCGUUUUAGAGCUAUGCUGUCCŨŨ |
| 292 | Ũ*ĜUAUAUGUCUGACAAUUCCGUUUUAGAGCUAUGCUGUCCŨ*Ũ |
| 293 | mUŨGGUAUAUGUCUGACAAUUCCGUUUUAGAGCUAUGCUGUCCUUŨmU |
| 294 | mU*ŨGGUAUAUGUCUGACAAUUCCGUUUUAGAGCUAUGCUGUCCUŨ*mU |
| 295 | mU*Ũ*GGUAUAUGUCUGACAAUUCCGUUUUAGAGCUAUGCUGUCCUU*Ũ*mU |
| 296 | mU*Ũ*U*GGUAUAUGUCUGACAAUUCCGUUUUAGAGCUAUGCUGUCCU*Ũ*U*mU |
| 297 | mU*ŨŨGGUAUAUGUCUGACAAUUCCGUUUUAGAGCUAUGCUGUCCUŨŨ*mU |
| 298 | mU*Ũ*ŨGGUAUAUGUCUGACAAUUCCGUUUUAGAGCUAUGCUGUCCUŨ*Ũ*mU |
| 299 | mU*Ũ*Ũ*GGUAUAUGUCUGACAAUUCCGUUUUAGAGCUAUGCUGUCCU*Ũ*Ũ*mU |
| 300 | ACUCCCAGAUUAGCCCCAUGGUUUUAGAGCUAUGCUGUCCUU |
| 301 | ŨACUCCCAGAUUAGCCCCAUGGUUUUAGAGCUAUGCUGUCCUŨ |
| 302 | ŨĜCUCCCAGAUUAGCCCCAUGGUUUUAGAGCUAUGCUGUCCŨŨ |
| 303 | Ũ*ĜCUCCCAGAUUAGCCCCAUGGUUUUAGAGCUAUGCUGUCCŨ*Ũ |
| 304 | mUŨACUCCCAGAUUAGCCCCAUGGUUUUAGAGCUAUGCUGUCCUUŨmU |
| 305 | mU*ŨACUCCCAGAUUAGCCCCAUGGUUUUAGAGCUAUGCUGUCCUŨ*mU |
| 306 | mU*Ũ*ACUCCCAGAUUAGCCCCAUGGUUUUAGAGCUAUGCUGUCCUU*Ũ*mU |
| 307 | mU*Ũ*U*ACUCCCAGAUUAGCCCCAUGGUUUUAGAGCUAUGCUGUCCU*U*Ũ*mU |
| 308 | mU*ŨŨACUCCCAGAUUAGCCCCAUGGUUUUAGAGCUAUGCUGUCCUŨŨ*mU |
| 309 | mU*Ũ*ŨACUCCCAGAUUAGCCCCAUGGUUUUAGAGCUAUGCUGUCCUŨ*Ũ*mU |
| 310 | mU*Ũ*Ũ*ACUCCCAGAUUAGCCCCAUGGUUUUAGAGCUAUGCUGUCCU*Ũ*Ũ*mU |
| 311 | AAGGACAGCCUUCUCUCUAAGUUUUAGAGCUAUGCUGUCCUU |
| 312 | ŨAAGGACAGCCUUCUCUCUAAGUUUUAGAGCUAUGCUGUCCUŨ |
| 313 | ŨĜAGGACAGCCUUCUCUCUAAGUUUUAGAGCUAUGCUGUCCŨŨ |
| 314 | Ũ*ĜAGGACAGCCUUCUCUCUAAGUUUUAGAGCUAUGCUGUCCŨ*Ũ |
| 315 | mUŨAAGGACAGCCUUCUCUCUAAGUUUUAGAGCUAUGCUGUCCUUŨmU |
| 316 | mU*ŨAAGGACAGCCUUCUCUCUAAGUUUUAGAGCUAUGCUGUCCUŨ*mU |
| 317 | mU*Ũ*AAGGACAGCCUUCUCUCUAAGUUUUAGAGCUAUGCUGUCCUU*Ũ*mU |
| 318 | mU*Ũ*U*AAGGACAGCCUUCUCUCUAAGUUUUAGAGCUAUGCUGUCCU*U*Ũ*mU |
| 319 | mU*ŨŨAAGGACAGCCUUCUCUCUAAGUUUUAGAGCUAUGCUGUCCUŨŨ*mU |
| 320 | mU*Ũ*ŨAAGGACAGCCUUCUCUCUAAGUUUUAGAGCUAUGCUGUCCUŨ*Ũ*mU |
| 321 | mU*Ũ*Ũ*AAGGACAGCCUUCUCUCUAAGUUUUAGAGCUAUGCUGUCCU*Ũ*Ũ*mU |
| 322 | UGCUGAUCACGCUGAUGCGGUUUUAGAGCUAUGCUGUCCUU |
| 323 | ŨUGCUGAUCACGCUGAUGCGGUUUUAGAGCUAUGCUGUCCUŨ |
| 324 | ŨŨGCUGAUCACGCUGAUGCGGUUUUAGAGCUAUGCUGUCCŨŨ |
| 325 | Ũ*ŨGCUGAUCACGCUGAUGCGGUUUUAGAGCUAUGCUGUCCŨ*Ũ |

TABLE 17 -continued 20-mer target length U-Guide molecules for editing CFTR

| SEQ ID NO. | U-GUIDE STRUCTURE (1 or 5' to 3') |
|---|---|
| 326 | mUŨUGCUGAUCACGCUGAUGCGGUUUUAGAGCUAUGCUGUCCUUŨmU |
| 327 | mU*ŨUGCUGAUCACGCUGAUGCGGUUUUAGAGCUAUGCUGUCCUUŨ*mU |
| 328 | mU*Ũ*UGCUGAUCACGCUGAUGCGGUUUUAGAGCUAUGCUGUCCUU*Ũ*mU |
| 329 | mU*Ũ*U*UGCUGAUCACGCUGAUGCGGUUUUAGAGCUAUGCUGUCCU*U*Ũ*mU |
| 330 | mU*ŨŨUGCUGAUCACGCUGAUGCGGUUUUAGAGCUAUGCUGUCCUŨŨ*mU |
| 331 | mU*Ũ*ŨUGCUGAUCACGCUGAUGCGGUUUUAGAGCUAUGCUGUCCUŨ*Ũ*mU |
| 332 | mU*Ũ*Ũ*UGCUGAUCACGCUGAUGCGGUUUUAGAGCUAUGCUGUCCU*Ũ*Ũ*mU |
| 333 | CUAUUCCCUUUGUCUUGAAGGUUUUAGAGCUAUGCUGUCCUU |
| 334 | ŨCUAUUCCCUUUGUCUUGAAGGUUUUAGAGCUAUGCUGUCCUŨ |
| 335 | ŨĈUAUUCCCUUUGUCUUGAAGGUUUUAGAGCUAUGCUGUCCŨŨ |
| 336 | Ũ*ĈUAUUCCCUUUGUCUUGAAGGUUUUAGAGCUAUGCUGUCCŨ*Ũ |
| 337 | mUŨCUAUUCCCUUUGUCUUGAAGGUUUUAGAGCUAUGCUGUCCUUŨmU |
| 338 | mU*ŨCUAUUCCCUUUGUCUUGAAGGUUUUAGAGCUAUGCUGUCCUUŨ*mU |
| 339 | mU*Ũ*CUAUUCCCUUUGUCUUGAAGGUUUUAGAGCUAUGCUGUCCUU*Ũ*mU |
| 340 | mU*Ũ*U*CUAUUCCCUUUGUCUUGAAGGUUUUAGAGCUAUGCUGUCCU*U*Ũ*mU |
| 341 | mU*ŨŨCUAUUCCCUUUGUCUUGAAGGUUUUAGAGCUAUGCUGUCCUŨŨ*mU |
| 342 | mU*Ũ*ŨCUAUUCCCUUUGUCUUGAAGGUUUUAGAGCUAUGCUGUCCUŨ*Ũ*mU |
| 343 | mU*Ũ*Ũ*CUAUUCCCUUUGUCUUGAAGGUUUUAGAGCUAUGCUGUCCU*Ũ*Ũ*mU |
| 344 | UUCAUUGACAUGCCAACAGAGUUUUAGAGCUAUGCUGUCCUU |
| 345 | ŨUUCAUUGACAUGCCAACAGAGUUUUAGAGCUAUGCUGUCCUŨ |
| 346 | ŨŨUCAUUGACAUGCCAACAGAGUUUUAGAGCUAUGCUGUCCŨŨ |
| 347 | Ũ*ŨUCAUUGACAUGCCAACAGAGUUUUAGAGCUAUGCUGUCCŨ*Ũ |
| 348 | mUŨUUCAUUGACAUGCCAACAGAGUUUUAGAGCUAUGCUGUCCUUŨmU |
| 349 | mU*ŨUUCAUUGACAUGCCAACAGAGUUUUAGAGCUAUGCUGUCCUUŨ*mU |
| 350 | mU*Ũ*UUCAUUGACAUGCCAACAGAGUUUUAGAGCUAUGCUGUCCUU*Ũ*mU |
| 351 | mU*Ũ*U*UUCAUUGACAUGCCAACAGAGUUUUAGAGCUAUGCUGUCCU*U*Ũ*mU |
| 352 | mU*ŨŨUUCAUUGACAUGCCAACAGAGUUUUAGAGCUAUGCUGUCCUŨŨ*mU |
| 353 | mU*Ũ*ŨUUCAUUGACAUGCCAACAGAGUUUUAGAGCUAUGCUGUCCUŨ*Ũ*mU |
| 354 | mU*Ũ*Ũ*UUCAUUGACAUGCCAACAGAGUUUUAGAGCUAUGCUGUCCU*Ũ*Ũ*mU |

In Table 17, N designates an RNA monomer, mN designates a 2'-O-methyl-RNA monomer, * designates a 3'-phosphorothioate linkage, Ũ designates a UNA-U monomer, and Ĝ designates a UNA-G monomer.

Example 7

Editing a Factor IX (F9) Genomic Site with a U-Guide Molecule for CRISPR/Cas9

Deficiency of Factor IX causes Hemophilia B. There are more than 100 known mutations of Factor IX.

Guide sequences of 20-mer length were identified that targeted certain regions of human F9 (human F9, NG_007994.1). The EntreZ Gene ID for these sequences is 2158.

20-mer guide sequences for F9 are shown in Table 18.

TABLE 18

20-mer guide sequences for F9

| SEQ ID NO. | TARGET SEQUENCE 5' → 3' |
|---|---|
| 355 | CUAAAAGGCAGAUGGUGAUG |
| 356 | CUUCCAUACAUUCUCUCUCA |

TABLE 18-continued 20-mer guide sequences for F9

| SEQ ID NO. | TARGET SEQUENCE 5' → 3' |
|---|---|
| 357 | AAAGGGACACCAACAUUCAU |
| 358 | AAGUCGAUAUCCCUCAGUAC |
| 359 | GGUGGAGAAGAUGCCAAACC |
| 360 | UUCUGUGCUGGCUUCCAUGA |

A U-Guide molecule is synthesized, wherein the molecule contains the 20-mer target sequence and a CRISPR sequence of S. pyogenes.

Examples of 20-mer target length U-Guide molecules for F9 are shown in Table 19.

TABLE 19

20-mer target length U-Guide molecules for editing F9

| SEQ ID NO. | U-GUIDE STRUCTURE (1 or 5' to 3') |
|---|---|
| 361 | CUAAAAGGCAGAUGGUGAUGGUUUUAGAGCUAUGCUGUCCUU |
| 362 | ŨCUAAAAGGCAGAUGGUGAUGGUUUUAGAGCUAUGCUGUCCUŨ |
| 363 | ŨCUAAAAGGCAGAUGGUGAUGGUUUUAGAGCUAUGCUGUCCŨŨ |
| 364 | Ũ*CUAAAAGGCAGAUGGUGAUGGUUUUAGAGCUAUGCUGUCCŨ*Ũ |
| 365 | mUŨCUAAAAGGCAGAUGGUGAUGGUUUUAGAGCUAUGCUGUCCUUŨmU |
| 366 | mU*ŨCUAAAAGGCAGAUGGUGAUGGUUUUAGAGCUAUGCUGUCCUUŨ*mU |
| 367 | mU*Ũ*CUAAAAGGCAGAUGGUGAUGGUUUUAGAGCUAUGCUGUCCUU*Ũ*mU |
| 368 | mU*Ũ*U*CUAAAAGGCAGAUGGUGAUGGUUUUAGAGCUAUGCUGUCCU*U*Ũ*mU |
| 369 | mU*ŨŨCUAAAAGGCAGAUGGUGAUGGUUUUAGAGCUAUGCUGUCCUŨŨ*mU |
| 370 | mU*Ũ*ŨCUAAAAGGCAGAUGGUGAUGGUUUUAGAGCUAUGCUGUCCUŨ*Ũ*mU |
| 371 | mU*Ũ*Ũ*CUAAAAGGCAGAUGGUGAUGGUUUUAGAGCUAUGCUGUCCU*Ũ*Ũ*mU |
| 372 | CUUCCAUACAUUCUCUCUCAGUUUUAGAGCUAUGCUGUCCUU |
| 373 | ŨCUUCCAUACAUUCUCUCUCAGUUUUAGAGCUAUGCUGUCCUŨ |
| 374 | ŨĈUUCCAUACAUUCUCUCUCAGUUUUAGAGCUAUGCUGUCCŨŨ |
| 375 | Ũ*ĈUUCCAUACAUUCUCUCUCAGUUUUAGAGCUAUGCUGUCCŨ*Ũ |
| 376 | mUŨCUUCCAUACAUUCUCUCUCAGUUUUAGAGCUAUGCUGUCCUUŨmU |
| 377 | mU*ŨCUUCCAUACAUUCUCUCUCAGUUUUAGAGCUAUGCUGUCCUUŨ*mU |
| 378 | mU*Ũ*CUUCCAUACAUUCUCUCUCAGUUUUAGAGCUAUGCUGUCCUU*Ũ*mU |
| 379 | mU*Ũ*U*CUUCCAUACAUUCUCUCUCAGUUUUAGAGCUAUGCUGUCCU*U*Ũ*mU |

TABLE 19-continued 20-mer target length U-Guide molecules for editing F9

| SEQ ID NO. | U-GUIDE STRUCTURE (1 or 5' to 3') |
|---|---|
| 380 | mU*ŨŨCUUCCAUACAUUCUCUCUCAGUUUUAGAGCUAUGCUGUCCUŨŨ*mU |
| 381 | mU*Ũ*ŨCUUCCAUACAUUCUCUCUCAGUUUUAGAGCUAUGCUGUCCUŨ*Ũ*mU |
| 382 | mU*Ũ*Ũ*CUUCCAUACAUUCUCUCUCAGUUUUAGAGCUAUGCUGUCCU*Ũ*Ũ*mU |
| 383 | AAAGGGACACCAACAUUCAUGUUUUAGAGCUAUGCUGUCCUU |
| 384 | ŨAAAGGGACACCAACAUUCAUGUUUUAGAGCUAUGCUGUCCUŨ |
| 385 | ŨÃAAGGGACACCAACAUUCAUGUUUUAGAGCUAUGCUGUCCŨŨ |
| 386 | Ũ*ÃAAGGGACACCAACAUUCAUGUUUUAGAGCUAUGCUGUCCŨ*Ũ |
| 387 | mUŨAAAGGGACACCAACAUUCAUGUUUUAGAGCUAUGCUGUCCUUŨmU |
| 388 | mU*ŨAAAGGGACACCAACAUUCAUGUUUUAGAGCUAUGCUGUCCUUŨ*mU |
| 389 | mU*Ũ*AAAGGGACACCAACAUUCAUGUUUUAGAGCUAUGCUGUCCUU*Ũ*mU |
| 390 | mU*Ũ*U*AAAGGGACACCAACAUUCAUGUUUUAGAGCUAUGCUGUCCU*U*Ũ*mU |
| 391 | mU*ŨŨAAAGGGACACCAACAUUCAUGUUUUAGAGCUAUGCUGUCCUŨŨ*mU |
| 392 | mU*Ũ*ŨAAAGGGACACCAACAUUCAUGUUUUAGAGCUAUGCUGUCCUŨ*Ũ*mU |
| 393 | mU*Ũ*Ũ*AAAGGGACACCAACAUUCAUGUUUUAGAGCUAUGCUGUCCU*Ũ*Ũ*mU |
| 394 | AAGUCGAUAUCCCUCAGUACGUUUUAGAGCUAUGCUGUCCUU |
| 395 | ŨAAGUCGAUAUCCCUCAGUACGUUUUAGAGCUAUGCUGUCCUŨ |
| 396 | ŨÃAGUCGAUAUCCCUCAGUACGUUUUAGAGCUAUGCUGUCCŨŨ |
| 397 | Ũ*ÃAGUCGAUAUCCCUCAGUACGUUUUAGAGCUAUGCUGUCCŨ*Ũ |
| 398 | mUŨAAGUCGAUAUCCCUCAGUACGUUUUAGAGCUAUGCUGUCCUUŨmU |
| 399 | mU*ŨAAGUCGAUAUCCCUCAGUACGUUUUAGAGCUAUGCUGUCCUUŨ*mU |
| 400 | mU*Ũ*AAGUCGAUAUCCCUCAGUACGUUUUAGAGCUAUGCUGUCCUU*Ũ*mU |
| 401 | mU*Ũ*U*AAGUCGAUAUCCCUCAGUACGUUUUAGAGCUAUGCUGUCCU*U*Ũ*mU |
| 402 | mU*ŨŨAAGUCGAUAUCCCUCAGUACGUUUUAGAGCUAUGCUGUCCUŨŨ*mU |
| 403 | mU*Ũ*ŨAAGUCGAUAUCCCUCAGUACGUUUUAGAGCUAUGCUGUCCUŨ*Ũ*mU |
| 404 | mU*Ũ*Ũ*AAGUCGAUAUCCCUCAGUACGUUUUAGAGCUAUGCUGUCCU*Ũ*Ũ*mU |
| 405 | GGUGGAGAAGAUGCCAAACCGUUUUAGAGCUAUGCUGUCCUU |
| 406 | ŨGGUGGAGAAGAUGCCAAACCGUUUUAGAGCUAUGCUGUCCUŨ |
| 407 | ŨĜGUGGAGAAGAUGCCAAACCGUUUUAGAGCUAUGCUGUCCŨŨ |
| 408 | Ũ*ĜGUGGAGAAGAUGCCAAACCGUUUUAGAGCUAUGCUGUCCŨ*Ũ |
| 409 | mUŨGGUGGAGAAGAUGCCAAACCGUUUUAGAGCUAUGCUGUCCUUŨmU |
| 410 | mU*ŨGGUGGAGAAGAUGCCAAACCGUUUUAGAGCUAUGCUGUCCUUŨ*mU |
| 411 | mU*Ũ*GGUGGAGAAGAUGCCAAACCGUUUUAGAGCUAUGCUGUCCUU*Ũ*mU |
| 412 | mU*Ũ*U*GGUGGAGAAGAUGCCAAACCGUUUUAGAGCUAUGCUGUCCU*U*Ũ*mU |
| 413 | mU*ŨŨGGUGGAGAAGAUGCCAAACCGUUUUAGAGCUAUGCUGUCCUŨŨ*mU |
| 414 | mU*Ũ*ŨGGUGGAGAAGAUGCCAAACCGUUUUAGAGCUAUGCUGUCCUŨ*Ũ*mU |
| 415 | mU*Ũ*Ũ*GGUGGAGAAGAUGCCAAACCGUUUUAGAGCUAUGCUGUCCU*Ũ*Ũ*mU |
| 416 | UUCUGUGCUGGCUUCCAUGAGUUUUAGAGCUAUGCUGUCCUU |

TABLE 19-continued

20-mer target length U-Guide molecules for editing F9

| SEQ ID NO. | U-GUIDE STRUCTURE (1 or 5' to 3') |
|---|---|
| 417 | ŨUUCUGUGCUGGCUUCCAUGAGUUUUAGAGCUAUGCUGUCCUŨ |
| 418 | ŨŨUCUGUGCUGGCUUCCAUGAGUUUUAGAGCUAUGCUGUCCŨŨ |
| 419 | Ũ*ŨUCUGUGCUGGCUUCCAUGAGUUUUAGAGCUAUGCUGUCCŨ*Ũ |
| 420 | mUŨUUCUGUGCUGGCUUCCAUGAGUUUUAGAGCUAUGCUGUCCUUŨmU |
| 421 | mU*ŨUUCUGUGCUGGCUUCCAUGAGUUUUAGAGCUAUGCUGUCCUUŨ*mU |
| 422 | mU*Ũ*UUCUGUGCUGGCUUCCAUGAGUUUUAGAGCUAUGCUGUCCUU*Ũ*mU |
| 423 | mU*Ũ*U*UUCUGUGCUGGCUUCCAUGAGUUUUAGAGCUAUGCUGUCCU*U*Ũ*mU |
| 424 | mU*ŨŨUUCUGUGCUGGCUUCCAUGAGUUUUAGAGCUAUGCUGUCCUŨŨ*mU |
| 425 | mU*Ũ*ŨUUCUGUGCUGGCUUCCAUGAGUUUUAGAGCUAUGCUGUCCUŨ*Ũ*mU |
| 426 | mU*Ũ*Ũ*UUCUGUGCUGGCUUCCAUGAGUUUUAGAGCUAUGCUGUCCU*Ũ*Ũ*mU |

In Table 19, N designates an RNA monomer, mN designates a 2'-O-methyl-RNA monomer, * designates a 3'-phosphorothioate linkage, Ũ designates a UNA-U monomer, and Ĝ designates a UNA-G monomer.

Example 8

Editing a KRAS Genomic Site with a U-Guide Molecule for CRISPR/Cas9

KRAS protein is essential in normal tissue signaling, and mutation of a KRAS gene is associated with many cancers.

Guide sequences of 20-mer length were identified that targeted certain regions of human KRAS (human KRAS, NG_007524.1). The EntreZ Gene ID for these sequences is 3845.

20-mer guide sequences for KRAS are shown in Table 20.

TABLE 20

20-mer guide sequences for KRAS

| SEQ ID NO. | TARGET SEQUENCE 5' → 3' |
|---|---|
| 427 | CUGAAUUAGCUGUAUCGUCA |
| 428 | CAAUGAGGGACCAGUACAUG |
| 429 | AGAACAAAUUAAAAGAGUUA |
| 430 | AAUCACAUUUAUUUCCUACU |
| 431 | UUCUCGAACUAAUGUAUAGA |
| 432 | GAAUAUGAUCCAACAAUAGA |

A U-Guide molecule is synthesized, wherein the molecule contains the 20-mer target sequence and a CRISPR sequence of S. pyogenes.

Examples of 20-mer target length U-Guide molecules for KRAS are shown in Table 21.

TABLE 21

20-mer target length U-Guide molecules for editing KRAS

| SEQ ID NO. | U-GUIDE STRUCTURE (1 or 5' to 3') |
|---|---|
| 433 | CUGAAUUAGCUGUAUCGUCAGUUUUAGAGCUAUGCUGUCCUU |
| 434 | ŨCUGAAUUAGCUGUAUCGUCAGUUUUAGAGCUAUGCUGUCCUŨ |
| 435 | ŨĈUGAAUUAGCUGUAUCGUCAGUUUUAGAGCUAUGCUGUCCŨŨ |
| 436 | Ũ*ĈUGAAUUAGCUGUAUCGUCAGUUUUAGAGCUAUGCUGUCCŨ*Ũ |

TABLE 21-continued 20-mer target length U-Guide molecules for editing KRAS

| SEQ ID NO. | U-GUIDE STRUCTURE (1 or 5' to 3') |
|---|---|
| 437 | mUŨCUGAAUUAGCUGUAUCGUCAGUUUUAGAGCUAUGCUGUCCUUŨmU |
| 438 | mU*ŨCUGAAUUAGCUGUAUCGUCAGUUUUAGAGCUAUGCUGUCCUUU*mU |
| 439 | mU*Ũ*CUGAAUUAGCUGUAUCGUCAGUUUUAGAGCUAUGCUGUCCUU*Ũ*mU |
| 440 | mU*Ũ*U*CUGAAUUAGCUGUAUCGUCAGUUUUAGAGCUAUGCUGUCCU*U*Ũ*mU |
| 441 | mU*ŨCUGAAUUAGCUGUAUCGUCAGUUUUAGAGCUAUGCUGUCCUŨŨ*mU |
| 442 | mU*Ũ*ŨCUGAAUUAGCUGUAUCGUCAGUUUUAGAGCUAUGCUGUCCUŨ*Ũ*mU |
| 443 | mU*Ũ*Ũ*CUGAAUUAGCUGUAUCGUCAGUUUUAGAGCUAUGCUGUCCU*Ũ*Ũ*mU |
| 444 | CAAUGAGGGACCAGUACAUGGUUUUAGAGCUAUGCUGUCCUU |
| 445 | ŨCAAUGAGGGACCAGUACAUGGUUUUAGAGCUAUGCUGUCCUŨ |
| 446 | ŨĈAAUGAGGGACCAGUACAUGGUUUUAGAGCUAUGCUGUCCŨŨ |
| 447 | Ũ*ĈAAUGAGGGACCAGUACAUGGUUUUAGAGCUAUGCUGUCCŨ*Ũ |
| 448 | mUŨCAAUGAGGGACCAGUACAUGGUUUUAGAGCUAUGCUGUCCUUŨmU |
| 449 | mU*ŨCAAUGAGGGACCAGUACAUGGUUUUAGAGCUAUGCUGUCCUUŨ*mU |
| 450 | mU*Ũ*CAAUGAGGGACCAGUACAUGGUUUUAGAGCUAUGCUGUCCUU*Ũ*mU |
| 451 | mU*Ũ*U*CAAUGAGGGACCAGUACAUGGUUUUAGAGCUAUGCUGUCCU*U*Ũ*mU |
| 452 | mU*ŨŨCAAUGAGGGACCAGUACAUGGUUUUAGAGCUAUGCUGUCCUŨŨ*mU |
| 453 | mU*Ũ*ŨCAAUGAGGGACCAGUACAUGGUUUUAGAGCUAUGCUGUCCUŨ*Ũ*mU |
| 454 | mU*Ũ*Ũ*CAAUGAGGGACCAGUACAUGGUUUUAGAGCUAUGCUGUCCU*Ũ*Ũ*mU |
| 455 | AGAACAAAUUAAAAGAGUUAGUUUUAGAGCUAUGCUGUCCUU |
| 456 | ŨAGAACAAAUUAAAAGAGUUAGUUUUAGAGCUAUGCUGUCCUŨ |
| 457 | ŨÃGAACAAAUUAAAAGAGUUAGUUUUAGAGCUAUGCUGUCCŨŨ |
| 458 | Ũ*ÃGAACAAAUUAAAAGAGUUAGUUUUAGAGCUAUGCUGUCCŨ*Ũ |
| 459 | mUŨAGAACAAAUUAAAAGAGUUAGUUUUAGAGCUAUGCUGUCCUUŨmU |
| 460 | mU*ŨAGAACAAAUUAAAAGAGUUAGUUUUAGAGCUAUGCUGUCCUUŨ*mU |
| 461 | mU*Ũ*AGAACAAAUUAAAAGAGUUAGUUUUAGAGCUAUGCUGUCCUU*Ũ*mU |
| 462 | mU*Ũ*U*AGAACAAAUUAAAAGAGUUAGUUUUAGAGCUAUGCUGUCCU*U*Ũ*mU |
| 463 | mU*ŨŨAGAACAAAUUAAAAGAGUUAGUUUUAGAGCUAUGCUGUCCUŨŨ*mU |
| 464 | mU*Ũ*ŨAGAACAAAUUAAAAGAGUUAGUUUUAGAGCUAUGCUGUCCUŨ*Ũ*mU |
| 465 | mU*Ũ*Ũ*AGAACAAAUUAAAAGAGUUAGUUUUAGAGCUAUGCUGUCCU*Ũ*Ũ*mU |
| 466 | AAUCACAUUUAUUCCUACUGUUUUAGAGCUAUGCUGUCCUU |
| 467 | ŨAAUCACAUUUAUUCCUACUGUUUUAGAGCUAUGCUGUCCUŨ |
| 468 | ŨÃAUCACAUUUAUUCCUACUGUUUUAGAGCUAUGCUGUCCŨŨ |
| 469 | Ũ*ÃAUCACAUUUAUUCCUACUGUUUUAGAGCUAUGCUGUCCŨ*Ũ |
| 470 | mUŨAAUCACAUUUAUUCCUACUGUUUUAGAGCUAUGCUGUCCUUŨmU |
| 471 | mU*ŨAAUCACAUUUAUUCCUACUGUUUUAGAGCUAUGCUGUCCUUŨ*mU |
| 472 | mU*Ũ*AAUCACAUUUAUUCCUACUGUUUUAGAGCUAUGCUGUCCUU*Ũ*mU |
| 473 | mU*Ũ*U*AAUCACAUUUAUUCCUACUGUUUUAGAGCUAUGCUGUCCU*U*Ũ*mU |

TABLE 21-continued 20-mer target length U-Guide molecules for editing KRAS

| SEQ ID NO. | U-GUIDE STRUCTURE (1 or 5' to 3') |
|---|---|
| 474 | mU*ŨŨAAUCACAUUUAUUUCCUACUGUUUUAGAGCUAUGCUGUCCUŨŨ*mU |
| 475 | mU*Ũ*ŨAAUCACAUUUAUUUCCUACUGUUUUAGAGCUAUGCUGUCCUŨ*Ũ*mU |
| 476 | mU*Ũ*Ũ*AAUCACAUUUAUUUCCUACUGUUUUAGAGCUAUGCUGUCCU*Ũ*Ũ*mU |
| 477 | UUCUCGAACUAAUGUAUAGAGUUUUAGAGCUAUGCUGUCCUU |
| 478 | ŨUUCUCGAACUAAUGUAUAGAGUUUUAGAGCUAUGCUGUCCUŨ |
| 479 | ŨŨUCUCGAACUAAUGUAUAGAGUUUUAGAGCUAUGCUGUCCŨŨ |
| 480 | Ũ*ŨUCUCGAACUAAUGUAUAGAGUUUUAGAGCUAUGCUGUCCŨ*Ũ |
| 481 | mUUŨUUCUCGAACUAAUGUAUAGAGUUUUAGAGCUAUGCUGUCCUUŨmU |
| 482 | mU*ŨUUCUCGAACUAAUGUAUAGAGUUUUAGAGCUAUGCUGUCCUUŨ*mU |
| 483 | mU*Ũ*UUCUCGAACUAAUGUAUAGAGUUUUAGAGCUAUGCUGUCCUU*Ũ*mU |
| 484 | mU*Ũ*U*UUCUCGAACUAAUGUAUAGAGUUUUAGAGCUAUGCUGUCCU*U*Ũ*mU |
| 485 | mU*ŨŨUUCUCGAACUAAUGUAUAGAGUUUUAGAGCUAUGCUGUCCUŨŨ*mU |
| 486 | mU*Ũ*ŨUUCUCGAACUAAUGUAUAGAGUUUUAGAGCUAUGCUGUCCUŨ*Ũ*mU |
| 487 | mU*Ũ*Ũ*UUCUCGAACUAAUGUAUAGAGUUUUAGAGCUAUGCUGUCCU*Ũ*Ũ*mU |
| 488 | GAAUAUGAUCCAACAAUAGAGUUUUAGAGCUAUGCUGUCCUU |
| 489 | ŨGAAUAUGAUCCAACAAUAGAGUUUUAGAGCUAUGCUGUCCUŨ |
| 490 | ŨĜAAUAUGAUCCAACAAUAGAGUUUUAGAGCUAUGCUGUCCŨŨ |
| 491 | Ũ*ĜGAAUAUGAUCCAACAAUAGAGUUUUAGAGCUAUGCUGUCCŨ*Ũ |
| 492 | mUŨGAAUAUGAUCCAACAAUAGAGUUUUAGAGCUAUGCUGUCCUUŨmU |
| 493 | mU*ŨGAAUAUGAUCCAACAAUAGAGUUUUAGAGCUAUGCUGUCCUUŨ*mU |
| 494 | mU*Ũ*GAAUAUGAUCCAACAAUAGAGUUUUAGAGCUAUGCUGUCCUU*Ũ*mU |
| 495 | mU*Ũ*U*GAAUAUGAUCCAACAAUAGAGUUUUAGAGCUAUGCUGUCCU*U*Ũ*mU |
| 496 | mU*ŨŨGAAUAUGAUCCAACAAUAGAGUUUUAGAGCUAUGCUGUCCUŨŨ*mU |
| 497 | mU*Ũ*ŨGAAUAUGAUCCAACAAUAGAGUUUUAGAGCUAUGCUGUCCUŨ*Ũ*mU |
| 498 | mU*Ũ*Ũ*GAAUAUGAUCCAACAAUAGAGUUUUAGAGCUAUGCUGUCCU*Ũ*Ũ*mU |

In Table 21, N designates an RNA monomer, mN designates a 2'-O-methyl-RNA monomer, * designates a 3'-phosphorothioate linkage, Ũ designates a UNA-U monomer, and Ĝ designates a UNA-G monomer.

Example 9

Editing a T Cell Genomic Site with a U-Guide Molecule for CRISPR/Cas9

Figure 13:
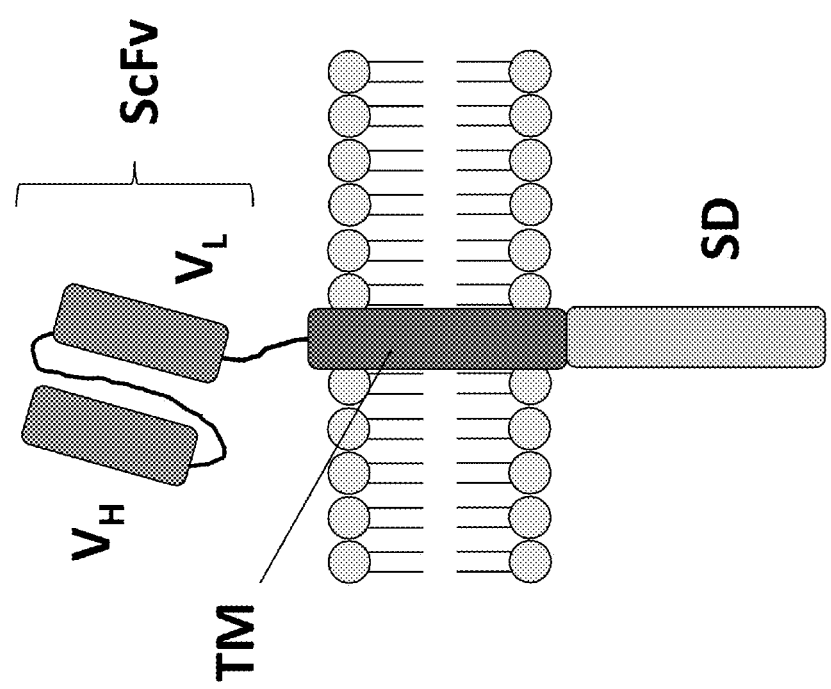
FIG. 13: shows a schematic representation of the structure of a chimeric antigen receptor (CAR). ScFv is a single chain fragment variable. $V_H$ is a heavy-chain variable region. $V_L$ is a light-chain variable region. TM is a transmembrane domain. SD is a signaling domain.

A schematic representation of the structure of a chimeric antigen receptor (CAR) is shown in FIG. 13. The CAR is an artificial T cell receptor that is inserted and expressed in the T cell. ScFv is a single chain fragment variable. $V_H$ is a heavy-chain variable region. $V_L$ is a light-chain variable region. TM is a transmembrane domain. SD is a signaling domain.

The CAR gene can be inserted into any constitutively expressed gene of a T cell.

For example, in one embodiment, the CAR gene can be inserted into a CD2 gene (cluster of differentiation 2). CD2 is a cell adhesion molecule found on the surface of T cells, which assists the T cells in adhering to antigen-presenting cells.

Figure 14:
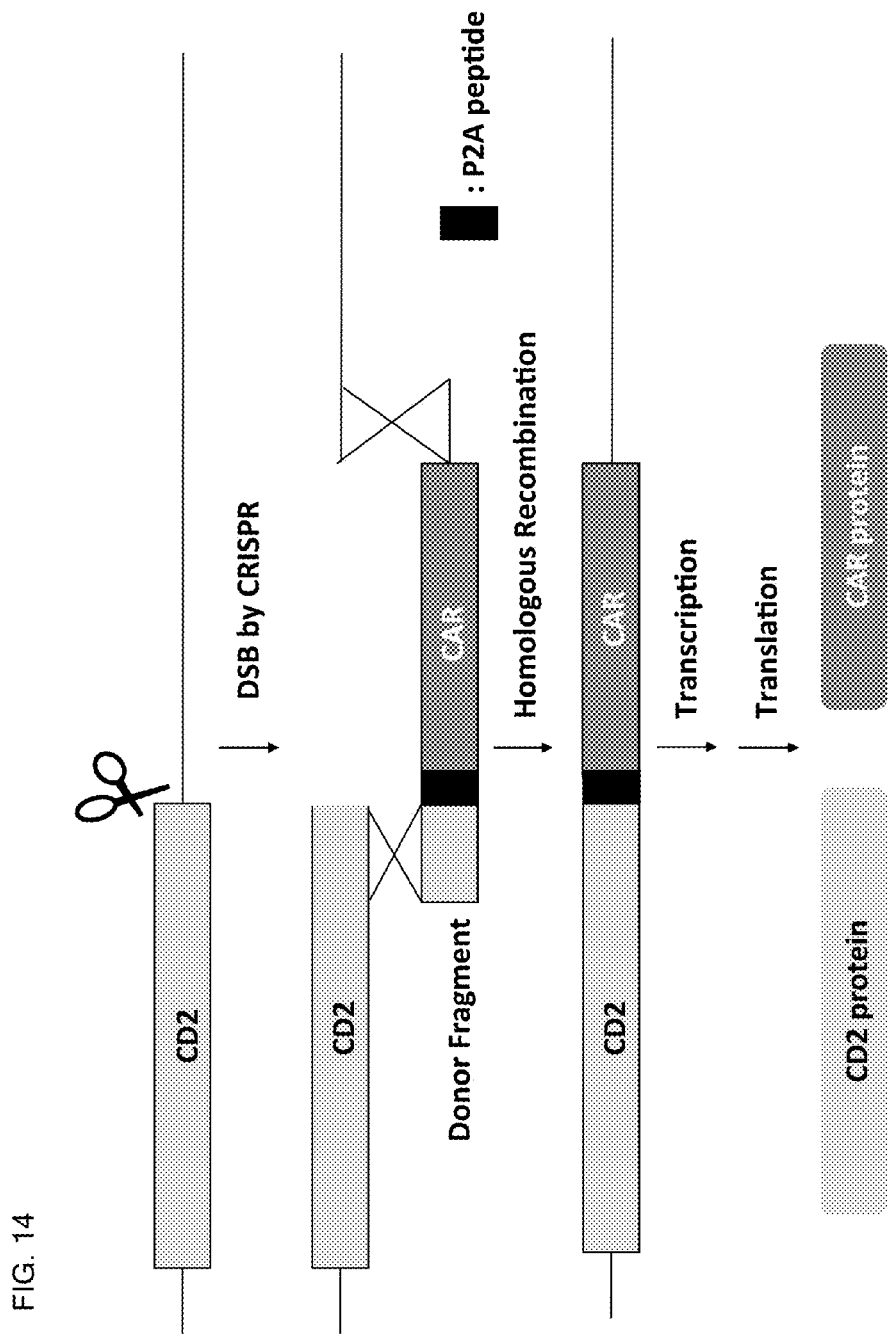
FIG. 14: shows a schematic of a method for introducing a CAR gene into a constitutive CD2 gene of a T cell, in which the CAR is downstream from the CD2. A double strand break is made with a U-Guide molecule of this invention. The gene inserted by homologous recombination can be comprised of a section of CD2, along with P2A and the CAR section. P2A peptide is a self-cleaving peptide that can be used to generate the two separate gene products CD2 protein and CAR protein. The CAR protein receptor can carry the specificity of a mAb against cancer cells of a subject in an adoptive immunotherapy strategy to kill the subject's cancer cells.

FIG. 14 shows a schematic of a method for introducing a CAR gene into a constitutive CD2 gene of a T cell, in which the CAR is downstream from the CD2. A double strand break is made with a U-Guide molecule of this invention. The gene inserted by homologous recombination can be comprised of a section of CD2, along with P2A and the CAR section. P2A peptide is a self-cleaving peptide that can be used to generate the two separate gene products CD2 protein and CAR protein. The CAR protein receptor can carry the specificity of a mAb against cancer cells of a subject in an adoptive immunotherapy strategy to kill the subject's cancer cells.

Figure 15:
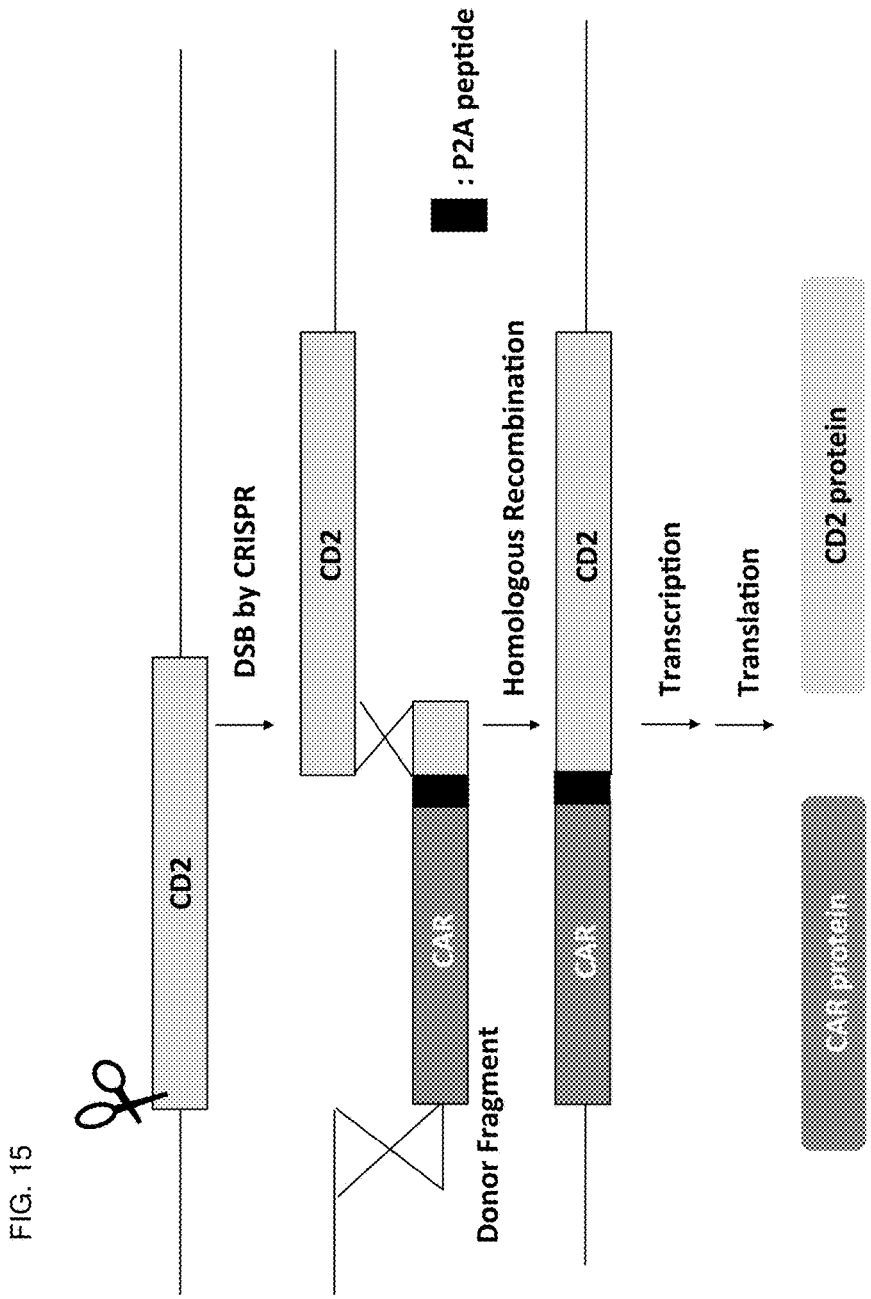
FIG. 15: shows a schematic of a method for introducing a CAR gene into a constitutive CD2 gene of a T cell, in which the CAR is upstream from the CD2.

FIG. 15 shows a schematic of a method for introducing a CAR gene into a constitutive CD2 gene of a T cell, in which the CAR is upstream from the CD2.

Several 20-mer guide sequences for CD2 are shown in Table 22.

TABLE 22

20-mer guide sequences for CD2

| SEQ ID NO. | SEQUENCE |
|---|---|
| 499 | GGGGUACCCCGUCGUCUUUU-5' (U-GUIDE) |
| 500 | 5'-CCT-CCCCATGGGGCAGCAGAAAA-3' (CD2 GENE) |
| 501 | 3'-GGA-GGGGTACCCCGTCGTCTTTT-5' (CD2 GENE) |
| 502 | AAGACGACCACUUGAACACA-5' (U-GUIDE) |
| 503 | 5'-CCT-TTCTGCTGGTGAACTTGTGT-3' (CD2 GENE) |
| 504 | 3'-GGA-AAGACGACCACTTGAACACA-5' (CD2 GENE) |
| 505 | GGGGTCTGGAGCTCAAGTCG-5' (U-GUIDE) |
| 506 | 5'-CCT-CCCCAGACCTCGAGTTCAGC-3' (CD2 GENE) |
| 507 | 3'-GGA-GGGGTCTGGAGCTCAAGTCG-5' (CD2 GENE) |
| 508 | GAUUAAUUUUUUCUAUCUUU-5' (U-GUIDE) |

TABLE 22-continued 20-mer guide sequences for CD2

| SEQ ID NO. | SEQUENCE |
|---|---|
| 509 | 5'-CCT-CTAATTAAAAAAGATAGAAA-3' (CD2 GENE) |
| 510 | 3'-GGA-GATTAATTTTTTCTATCTTT-5' (CD2 GENE) |

Guide sequences of 20-mer length were identified that targeted certain regions of human CD2.

20-mer guide sequences for CD2 are shown in Table 23.

TABLE 23

20-mer guide sequences for CD2

| SEQ ID NO. | TARGET SEQUENCE 5' → 3' |
|---|---|
| 511 | UUUUCUGCUGCCCCAUGGGG |
| 512 | ACACAAGUUCACCAGCAGAA |
| 513 | GCTGAACTCGAGGTCTGGGG |
| 514 | UUUCUAUCUUUUUUAAUUAG |

A U-Guide molecule is synthesized, wherein the molecule contains the 20-mer target sequence and a CRISPR sequence of S. pyogenes.

Examples of 20-mer target length U-Guide molecules for CD2 are shown in Table 24.

TABLE 24

20-mer target length U-Guide molecules for editing CD2

| SEQ ID NO. | U-GUIDE STRUCTURE (1 or 5' to 3') |
|---|---|
| 515 | UUUUCUGCUGCCCCAUGGGGUUUUAGAGCUAUGCUGUCCUU |
| 516 | ŨUUUUCUGCUGCCCCAUGGGGUUUUAGAGCUAUGCUGUCCUŨ |
| 517 | ŨŨUUUCUGCUGCCCCAUGGGGUUUUAGAGCUAUGCUGUCCŨŨ |
| 518 | Ũ*ŨUUUCUGCUGCCCCAUGGGGUUUUAGAGCUAUGCUGUCCŨ*Ũ |
| 519 | mUŨUUUUCUGCUGCCCCAUGGGGUUUUAGAGCUAUGCUGUCCUUŨmU |
| 520 | mU*ŨUUUUCUGCUGCCCCAUGGGGUUUUAGAGCUAUGCUGUCCUUŨ*mU |
| 521 | mU*Ũ*UUUUCUGCUGCCCCAUGGGGUUUUAGAGCUAUGCUGUCCUU*Ũ*mU |
| 522 | mU*Ũ*U*UUUUCUGCUGCCCCAUGGGGUUUUAGAGCUAUGCUGUCCU*U*Ũ*mU |
| 523 | mU*ŨŨUUUUCUGCUGCCCCAUGGGGUUUUAGAGCUAUGCUGUCCUŨŨ*mU |
| 524 | mU*Ũ*ŨUUUUCUGCUGCCCCAUGGGGUUUUAGAGCUAUGCUGUCCUŨ*Ũ*mU |
| 525 | mU*Ũ*Ũ*UUUUCUGCUGCCCCAUGGGGUUUUAGAGCUAUGCUGUCCU*Ũ*Ũ*mU |
| 526 | ACACAAGUUCACCAGCAGAAGUUUUAGAGCUAUGCUGUCCUU |
| 527 | ŨACACAAGUUCACCAGCAGAAGUUUUAGAGCUAUGCUGUCCUŨ |
| 528 | ŨÃCACAAGUUCACCAGCAGAAGUUUUAGAGCUAUGCUGUCCŨŨ |
| 529 | Ũ*ÃCACAAGUUCACCAGCAGAAGUUUUAGAGCUAUGCUGUCCŨ*Ũ |
| 530 | mUŨACACAAGUUCACCAGCAGAAGUUUUAGAGCUAUGCUGUCCUUŨmU |
| 531 | mU*ŨACACAAGUUCACCAGCAGAAGUUUUAGAGCUAUGCUGUCCUUŨ*mU |

TABLE 24-continued 20-mer target length U-Guide molecules for editing CD2

| SEQ ID NO. | U-GUIDE STRUCTURE (1 or 5' to 3') |
|---|---|
| 532 | mU*Ũ*ACACAAGUUCACCAGCAGAAGUUUUAGAGCUAUGCUGUCCUU*Ũ*mU |
| 533 | mU*Ũ*U*ACACAAGUUCACCAGCAGAAGUUUUAGAGCUAUGCUGUCCU*U*Ũ*mU |
| 534 | mU*ŨŨACACAAGUUCACCAGCAGAAGUUUUAGAGCUAUGCUGUCCUŨŨ*mU |
| 535 | mU*Ũ*ŨACACAAGUUCACCAGCAGAAGUUUUAGAGCUAUGCUGUCCUŨ*Ũ*mU |
| 536 | mU*Ũ*Ũ*ACACAAGUUCACCAGCAGAAGUUUUAGAGCUAUGCUGUCCU*Ũ*Ũ*mU |
| 537 | GCTGAACTCGAGGTCTGGGGGUUUUAGAGCUAUGCUGUCCUU |
| 538 | ŨGCTGAACTCGAGGTCTGGGGGUUUUAGAGCUAUGCUGUCCUŨ |
| 539 | ŨĜCTGAACTCGAGGTCTGGGGGUUUUAGAGCUAUGCUGUCCŨŨ |
| 540 | Ũ*ĜCTGAACTCGAGGTCTGGGGGUUUUAGAGCUAUGCUGUCCŨ*Ũ |
| 541 | mUŨGCTGAACTCGAGGTCTGGGGGUUUUAGAGCUAUGCUGUCCUUŨmU |
| 542 | mU*ŨGCTGAACTCGAGGTCTGGGGGUUUUAGAGCUAUGCUGUCCUUŨ*mU |
| 543 | mU*Ũ*UGCTGAACTCGAGGTCTGGGGGUUUUAGAGCUAUGCUGUCCUU*Ũ*mU |
| 544 | mU*Ũ*U*GCTGAACTCGAGGTCTGGGGGUUUUAGAGCUAUGCUGUCCU*U*Ũ*mU |
| 545 | mU*ŨŨGCTGAACTCGAGGTCTGGGGGUUUUAGAGCUAUGCUGUCCUŨŨ*mU |
| 546 | mU*Ũ*ŨGCTGAACTCGAGGTCTGGGGGUUUUAGAGCUAUGCUGUCCUŨ*Ũ*mU |
| 547 | mU*Ũ*Ũ*GCTGAACTCGAGGTCTGGGGGUUUUAGAGCUAUGCUGUCCU*Ũ*Ũ*mU |
| 548 | UUUCUAUCUUUUUUAAUUAGGUUUUAGAGCUAUGCUGUCCUU |
| 549 | ŨUUUCUAUCUUUUUUAAUUAGGUUUUAGAGCUAUGCUGUCCUŨ |
| 550 | ŨŨUUCUAUCUUUUUUAAUUAGGUUUUAGAGCUAUGCUGUCCŨŨ |
| 551 | Ũ*ŨUUCUAUCUUUUUUAAUUAGGUUUUAGAGCUAUGCUGUCCŨ*Ũ |
| 552 | mUŨUUUCUAUCUUUUUUAAUUAGGUUUUAGAGCUAUGCUGUCCUUŨmU |
| 553 | mU*ŨUUUCUAUCUUUUUUAAUUAGGUUUUAGAGCUAUGCUGUCCUUŨ*mU |
| 554 | mU*Ũ*UUUCUAUCUUUUUUAAUUAGGUUUUAGAGCUAUGCUGUCCUU*Ũ*mU |
| 555 | mU*Ũ*U*UUUCUAUCUUUUUUAAUUAGGUUUUAGAGCUAUGCUGUCCU*U*Ũ*mU |
| 556 | mU*ŨŨUUUCUAUCUUUUUUAAUUAGGUUUUAGAGCUAUGCUGUCCUŨŨ*mU |
| 557 | mU*Ũ*ŨUUUCUAUCUUUUUUAAUUAGGUUUUAGAGCUAUGCUGUCCUŨ*Ũ*mU |
| 558 | mU*Ũ*Ũ*UUUCUAUCUUUUUUAAUUAGGUUUUAGAGCUAUGCUGUCCU*Ũ*Ũ*mU |

In Table 24, N designates an RNA monomer, mN designates a 2'-O-methyl-RNA monomer, * designates a 3'-phosphorothioate linkage, Ũ designates a UNA-U monomer, and Ĝ designates a UNA-G monomer.

Example 10

Protocol for Sequence Trace Decomposition (TIDE)

293 cells expressing either V30M or WT human TTR were transfected by LIPOFECTAMINE MESSENGER-MAX reagent with Cas9 mRNA 4 hours prior to transfection with the comparative guide or UNA-Guide (UNA1), each of which were pre-annealed with tracrRNA, and targeting the V30M mutation of hTTR. 48 h following transfection, genomic DNA was isolated and a 1048 by fragment of hTTR was amplified using primers

SEQ ID NO: 559
5' ACAACTGGTAAGAAGGAGTGAC3' and

SEQ ID NO: 560
5' CCTTGGGTTTTGGGTGATCC3'.

The PCR product was purified and then sanger sequenced using either the

SEQ ID NO:561
5' TCGACACTTACGTTCCTGAT3' or

SEQ ID NO:562
5'CATACTTGACCTCTGCCTAC3' primers.

Example 11

Editing a TTR Genomic Site with a U-Guide Molecule for CRISPR/Cas9

Guide sequences of 20-mer length were identified that targeted certain regions of human TTR, accession number NC_000018.10.

20-mer guide sequences for hTTR are shown in Table 25.

TABLE 25

20-mer guide sequences for hTTR

| SEQ ID NO. | TARGET SEQUENCE 5' → 3' | |
|---|---|---|
| 563 | TAAGGTGGTGCCGACAGTAG-5' | (GUIDE - V122I) |
| 564 | 5'-CCT-ATTCCACCACGGCTGTCATC-3' | (V122I TTR GENE) |
| 565 | 3'-GGA-TAAGGTGGTGCCGACAGTAG-5' | (V122I TTR GENE) |

TABLE 25-continued 20-mer guide sequences for hTTR

| SEQ ID NO. | TARGET SEQUENCE 5' → 3' | |
|---|---|---|
| 566 | GTCAACACTCGGGTACGCCG-5' | (GUIDE - L55P) |
| 567 | 5'-CCT-CAGTTGTGAGCCCATGCGGC-3' | (L55P TTR GENE) |
| 568 | 3'-GGA-GTCAACACTCGGGTACGCCG-5' | (L55P TTR GENE) |
| 569 | GTCTGTGTTTATGGTCAGGT-5' | (GUIDE) |
| 570 | 5'-CCT-CAGACACAAATACCAGTCCA-3' | (SP TTR GENE) |
| 571 | 3'-GGA-GTCTGTGTTTATGGTCAGGT-5' | (SP TTR GENE) |

A U-Guide molecule is synthesized, wherein the molecule contains the 20-mer target sequence and a CRISPR sequence of *S. pyogenes*.

Examples of 20-mer target length U-Guide molecules for V122I hTTR are shown in Table 26.

TABLE 26

20-mer target length U-Guide molecules for editing the V122I region of hTTR

| SEQ ID NO. | U-GUIDE STRUCTURE (1 or 5' to 3') |
|---|---|
| 572 | GAUGACAGCCGUGGUGGAAUGUUUUAGAGCUAUGCUGUCCUU |
| 573 | ŨGAUGACAGCCGUGGUGGAAUGUUUUAGAGCUAUGCUGUCCUŨ |
| 574 | ŨĜAUGACAGCCGUGGUGGAAUGUUUUAGAGCUAUGCUGUCCŨŨ |
| 575 | Ũ*ĜAUGACAGCCGUGGUGGAAUGUUUUAGAGCUAUGCUGUCCŨ*Ũ |
| 576 | mUŨUGAUGACAGCCGUGGUGGAAUGUUUUAGAGCUAUGCUGUCCUUŨmU |
| 577 | mU*ŨUGAUGACAGCCGUGGUGGAAUGUUUUAGAGCUAUGCUGUCCUUŨ*mU |
| 578 | mU*Ũ*UGAUGACAGCCGUGGUGGAAUGUUUUAGAGCUAUGCUGUCCUU*Ũ*mU |
| 579 | mU*Ũ*U*GAUGACAGCCGUGGUGGAAUGUUUUAGAGCUAUGCUGUCCU*U*Ũ*mU |
| 580 | mU*ŨŨGGAUGACAGCCGUGGUGGAAUGUUUUAGAGCUAUGCUGUCCUŨŨ*mU |
| 581 | mU*Ũ*ŨGAUGACAGCCGUGGUGGAAUGUUUUAGAGCUAUGCUGUCCUŨ*Ũ*mU |
| 582 | mU*Ũ*Ũ*GAUGACAGCCGUGGUGGAAUGUUUUAGAGCUAUGCUGUCCU*Ũ*Ũ*mU |

Examples of 20-mer target length U-Guide molecules for region L55P of hTTR are shown in Table 27.

TABLE 27

20-mer target length U-Guide molecules for editing the L55P region of hTTR

| SEQ ID NO. | U-GUIDE STRUCTURE (1 or 5' to 3') |
|---|---|
| 583 | GCCGCAUGGGCUCACAACUGGUUUUAGAGCUAUGCUGUCCUU |
| 584 | ŨGCCGCAUGGGCUCACAACUGGUUUUAGAGCUAUGCUGUCCUŨ |
| 585 | ŨĜCCGCAUGGGCUCACAACUGGUUUUAGAGCUAUGCUGUCCŨŨ |
| 586 | Ũ*ĜCCGCAUGGGCUCACAACUGGUUUUAGAGCUAUGCUGUCCŨ*Ũ |
| 587 | mUŨUGCCGCAUGGGCUCACAACUGGUUUUAGAGCUAUGCUGUCCUUŨmU |

TABLE 27-continued 20-mer target length U-Guide molecules for editing the L55P region of hTTR

| SEQ ID NO. | U-GUIDE STRUCTURE (1 or 5' to 3') |
|---|---|
| 588 | mU*ŨUGCCGCAUGGGCUCACAACUGGUUUUAGAGCUAUGCUGUCCUUŨ*mU |
| 589 | mU*Ũ*UGCCGCAUGGGCUCACAACUGGUUUUAGAGCUAUGCUGUCCUU*Ũ*mU |
| 590 | mU*Ũ*U*GCCGCAUGGGCUCACAACUGGUUUUAGAGCUAUGCUGUCCU*U*Ũ*mU |
| 591 | mU*ŨŨGCCGCAUGGGCUCACAACUGGUUUUAGAGCUAUGCUGUCCUŨŨ*mU |
| 592 | mU*Ũ*ŨGCCGCAUGGGCUCACAACUGGUUUUAGAGCUAUGCUGUCCUŨ*Ũ*mU |
| 593 | mU*Ũ*Ũ*GCCGCAUGGGCUCACAACUGGUUUUAGAGCUAUGCUGUCCU*Ũ*Ũ*mU |

Examples of 20-mer target length U-Guide molecules for region SP of hTTR are shown in Table 28.

TABLE 28

20-mer target length U-Guide molecules for editing the SP region of hTTR

| SEQ ID NO. | U-GUIDE STRUCTURE (1 or 5' to 3') |
|---|---|
| 594 | UGGACUGGUAUUUGUGUCUGGUUUUAGAGCUAUGCUGUCCUU |
| 595 | ŨUGGACUGGUAUUUGUGUCUGGUUUUAGAGCUAUGCUGUCCUŨ |
| 596 | ŨŨGGACUGGUAUUUGUGUCUGGUUUUAGAGCUAUGCUGUCCŨŨ |
| 597 | Ũ*ŨGGACUGGUAUUUGUGUCUGGUUUUAGAGCUAUGCUGUCCŨ*Ũ |
| 598 | mUŨUUGGACUGGUAUUUGUGUCUGGUUUUAGAGCUAUGCUGUCCUUŨmU |
| 599 | mU*ŨUUGGACUGGUAUUUGUGUCUGGUUUUAGAGCUAUGCUGUCCUUŨ*mU |
| 600 | mU*Ũ*UUGGACUGGUAUUUGUGUCUGGUUUUAGAGCUAUGCUGUCCUU*Ũ*mU |
| 601 | mU*Ũ*U*UGGACUGGUAUUUGUGUCUGGUUUUAGAGCUAUGCUGUCCU*U*Ũ*mU |
| 602 | mU*ŨŨUGGACUGGUAUUUGUGUCUGGUUUUAGAGCUAUGCUGUCCUŨŨ*mU |
| 603 | mU*Ũ*ŨUGGACUGGUAUUUGUGUCUGGUUUUAGAGCUAUGCUGUCCUŨ*Ũ*mU |
| 604 | mU*Ũ*Ũ*UGGACUGGUAUUUGUGUCUGGUUUUAGAGCUAUGCUGUCCU*Ũ*Ũ*mU |

Example 12

An Example of a crRNA for a U-Guide Molecule for CRISPR/Cas Gene Editing is

SEQ ID NO: 605
5'-GUUUUAGAGCUAUGCU-3'.

Example 13

An Example of a tracrRNA, as Used Above, for a U-Guide System for CRISPR/Cas Gene Editing is SEQ ID NO: 606
5'-mA*mG*mC*mAmUmAmGmCmAAGUUAAAAUAAGGCUAGUCCGUUAUC AAmCmUmUmGmAmAmAmAmGmUmGmGmCmAmCmCmGmAmGmUmCmGmG mUmGmCmU*mU*mU-3'.

It is understood that this invention is not limited to the particular methodology, protocols, materials, and reagents described, as these may vary. It is also to be understood that the terminology used herein is for the purpose of describing particular embodiments only, and is not intended to limit the scope of the present invention, which will be encompassed by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprises," "comprising", "containing," "including", and "having" can be used interchangeably.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

All of the features disclosed in this specification may be combined in any combination. Each feature disclosed in this specification may be replaced by an alternative feature serving the same, equivalent, or similar purpose.

What is claimed is:

1. A guide compound targeted to a genomic DNA, comprising a target guide chain of 14-24 contiguous monomers attached to a crRNA, wherein the guide compound directs CRISPR gene editing of the genomic DNA, wherein the monomers comprise UNA monomers and nucleic acid monomers, and wherein the guide compound comprises a sequence of bases targeted to direct CRISPR gene editing of the genomic DNA.

2. The guide compound of claim 1, wherein the guide compound directs double strand breaks in human gene TTR and the target guide chain comprises 16-20 contiguous monomers of 5'-UGCAUGGCCACAUUGAUGGC-3' (SEQ ID NO:13), wherein the crRNA is attached at the 3' end of the target guide chain.

3. The guide compound of claim 2, wherein the guide compound comprises SEQ ID NO:32.

4. The guide compound of claim 1, wherein the guide compound directs double strand breaks in human gene TTR and the target guide chain comprises 16-20 contiguous monomers of 5'-CACAUGCAUGGCCACAUUGA-3' (SEQ ID NO:40), wherein the crRNA is attached at the 3' end of the target guide chain.

5. The guide compound of claim 4, wherein the guide compound comprises SEQ ID NO:61.

6. The guide compound of claim 1, wherein the crRNA is 5'-GUUUUAGAGCUAUGCU-3' (SEQ ID NO:605).

7. The guide compound of claim 1, wherein the sequence of bases of the target guide chain has up to three mismatches from the genomic DNA.

8. The guide compound of claim 1, wherein the guide compound contains one to five UNA monomers.

9. The guide compound of claim 1, wherein one or more of the nucleic acid monomers is a 2'-O-methyl ribonucleotide, a 2'-O-methyl purine nucleotide, a 2'-deoxy-2'-fluoro ribonucleotide, a 2'-deoxy-2'-fluoro pyrimidine nucleotide, a 2'-deoxy ribonucleotide, a 2'-deoxy purine nucleotide, a universal base nucleotide, a 5-C-methyl-nucleotide, an inverted deoxyabasic monomer residue, a 3'-end stabilized nucleotide, a 3'-glyceryl nucleotide, a 3'-inverted abasic nucleotide, a 3'-inverted thymidine, a locked nucleic acid nucleotide (LNA), a 2'-O,4'-C-methylene-(D-ribofuranosyl) nucleotide, a 2'-methoxyethoxy (MOE) nucleotide, a 2'-methyl-thio-ethyl, 2'-deoxy-2'-fluoro nucleotide, a 2'-O-methyl nucleotide, a 2',4'-Constrained 2'-O-Methoxyethyl (cMOE), a 2'-O-Ethyl (cEt), a 2'-amino nucleotide, a 2'-O-amino nucleotide, a 2'-C-allyl nucleotides, a 2'-O-allyl nucleotide, a N$^6$-methyladenosine nucleotide, a nucleotide with modified base 5-(3-amino)propyluridine, a nucleotide with modified base 5-(2-mercapto)ethyluridine, a nucleotide with modified base 5-bromouridine, a nucleotide with modified base 8-bromoguanosine, a nucleotide with modified base 7-deazaadenosine, a 2'-O-aminopropyl substituted nucleotide, or a nucleotide with a 2'-OH group replaced with a 2'-R, a 2'-OR, a 2'-halogen, a 2'-SR, or a 2'-amino, where R can be H, alkyl, alkenyl, or alkynyl.

10. The guide compound of claim 1, wherein one or more of the last three monomers at each end of the guide compound is connected by a phosphorothioate, a chiral phosphorothioate, or a phosphorodithioate linkage.

11. The guide compound of claim 1, wherein the guide compound directs double strand breaks in a gene selected from TTR, BIRC5, CDK16, STAT3, CFTR, F9, KRAS, and CAR.

12. The guide compound of claim 1, wherein the genomic DNA contains a target disease-related single nucleotide polymorphism.

13. The guide compound of claim 1, wherein the guide compound directs double strand breaks in a disease-related allele.

14. The guide compound of claim 1, wherein the guide compound directs double strand breaks in a disease-related allele selected from V30M TTR, G284R ColA1, L132P Keratin12, R135T Keratin12, G85R SOD1, G272V Tau, P301L Tau, V337M Tau, R406W Tau, Q39STOP beta-Globin, T8993G/C mtDNA, G719S EGFR, and G12C Kras.

15. The guide compound of claim 1, comprising 30-300 contiguous monomers.

16. The guide compound of claim 1, wherein the CRISPR gene editing uses Cas9.

17. The guide compound of claim 1, wherein the guide compound directs more double strand breaks in a disease-related allele than in the same allele as a wild type.

18. A guide compound of claim 1 annealed with a tracrRNA.

19. The guide compound of claim 18, wherein the tracrRNA is derived from *S. pneumonia, S. pyogenes, N. menigiditis,* or *S. thermophiles.*

20. The guide compound of claim 18, wherein the tracrRNA is SEQ ID NO:606.

21. A pharmaceutical composition comprising one or more guide compounds of claim 18 and a pharmaceutically acceptable carrier.

22. The composition of claim 21, wherein the pharmaceutically acceptable carrier comprises a viral vector or a non-viral vector.

23. The composition of claim 21, wherein the pharmaceutically acceptable carrier comprises liposomes.

24. A guide compound of claim 1 annealed with a tracrRNA and complexed with a CRISPR-associated gene editing protein.

25. The guide compound of claim 24, wherein the CRISPR-associated gene editing protein is Cas9.

* * * * *